United States Patent
Tseng et al.

(10) Patent No.: US 10,344,262 B2
(45) Date of Patent: Jul. 9, 2019

(54) DIFFERENTIATION OF PRIMATE PLURIPOTENT STEM CELLS TO HEMATOPOIETIC LINEAGE CELLS

(71) Applicant: Asterias Biotherapeutics, Inc., Fremont, CA (US)

(72) Inventors: Suyi Tseng, San Francisco, CA (US); Anish Sen Majumdar, Mumbai (IN); Kevin Nishimoto, San Mateo, CA (US); Anita Reddy, San Ramon, CA (US); Jane S. Lebkowski, Portola Valley, CA (US)

(73) Assignee: Asterias Biotherapeutics, Inc., Fremont, CA (US)

( * ) Notice: Subject to any disclaimer, the term of this patent is extended or adjusted under 35 U.S.C. 154(b) by 0 days.

(21) Appl. No.: 15/426,030

(22) Filed: Feb. 6, 2017

(65) Prior Publication Data

US 2017/0369842 A1    Dec. 28, 2017

Related U.S. Application Data

(63) Continuation of application No. 13/312,349, filed on Dec. 6, 2011, now abandoned, which is a continuation of application No. 12/412,183, filed on Mar. 26, 2009, now Pat. No. 8,093,049.

(60) Provisional application No. 61/039,835, filed on Mar. 27, 2008, provisional application No. 61/081,242, filed on Jul. 16, 2008.

(51) Int. Cl.
*C12N 5/0784* (2010.01)
*A61K 39/00* (2006.01)

(52) U.S. Cl.
CPC .... *C12N 5/0639* (2013.01); *A61K 2039/5154* (2013.01); *C12N 2501/02* (2013.01); *C12N 2501/125* (2013.01); *C12N 2501/155* (2013.01); *C12N 2501/165* (2013.01); *C12N 2501/22* (2013.01); *C12N 2501/23* (2013.01); *C12N 2501/24* (2013.01); *C12N 2501/52* (2013.01); *C12N 2506/02* (2013.01)

(58) Field of Classification Search
CPC .................................................. C12N 5/0639
See application file for complete search history.

(56) References Cited

U.S. PATENT DOCUMENTS

| | | | |
|---|---|---|---|
| 5,843,780 A | 12/1998 | Thomson | |
| 6,200,806 B1 | 3/2001 | Thomson | |
| 7,029,913 B2 | 4/2006 | Thomson | |
| 7,247,480 B2 | 7/2007 | Waldmann | |
| 2002/0046410 A1 | 4/2002 | Lanza et al. | |
| 2002/0086005 A1 | 7/2002 | Chiu et al. | |
| 2003/0096314 A1 | 5/2003 | Steinman et al. | |
| 2003/0096404 A1 | 5/2003 | Pykett et al. | |
| 2003/0153082 A1 | 8/2003 | Bhatia | |
| 2006/0057120 A1 | 3/2006 | Bosch | |
| 2006/0057129 A1 | 3/2006 | Lebkowski et al. | |
| 2006/0063255 A1 | 3/2006 | Lebkowski et al. | |
| 2006/0147432 A1 | 7/2006 | Moore et al. | |
| 2006/0275901 A1 | 12/2006 | Slukvin et al. | |
| 2007/0072295 A1 | 3/2007 | Slukvin et al. | |
| 2007/0269436 A1 | 11/2007 | Chen | |
| 2008/0050347 A1 | 2/2008 | Ichim | |
| 2008/0058412 A1 | 3/2008 | Caumont-Bertrand et al. | |
| 2008/0069836 A1 | 3/2008 | Nabel et al. | |
| 2011/0151554 A1 | 6/2011 | Yuo et al. | |

FOREIGN PATENT DOCUMENTS

| | | |
|---|---|---|
| EP | 0708336 | 4/1996 |
| WO | 2001/051616 | 7/2000 |
| WO | 2001/051610 | 7/2001 |
| WO | 2006/020889 | 2/2006 |
| WO | 2006/130651 | 12/2006 |

OTHER PUBLICATIONS

Antonchuk, J., "HOXB4-induced expansion of adult hematopoietic stem cells ex vivo", Cell 109(1), 2002, pp. 39-45.
Bandi, S., "Human embryonic stem cell (hES) derived dendritic cells are functionally normal and are susceptible to HIV-1 infection", AIDS Res. Ther. 5, 2008, pp. 1-9.
Cao, M., "Gamma irradiation of human dendritic cells influences proliferation and cytokine profile of T cells in autologous mixed lymphocyte reaction", Cell Biol. Intl. 28, 2004, pp. 223-228.
Celluzzi, C., "Peptide-pulsed dendritic cells induce antigen-specific CTL-mediated protective tumor immunity", J. Exp. Med. 183, 1996, pp. 283-287.
Chadwick, K. et al., "Cytokines and BMP-4 promote hematopoietic differentiation of human embryonic stem cells," Blood 102(3), (2003), pp. 906-915.
Chicha, L., "Clonal type I interferon-producing and dendritic cell precursors are contained in both human lymphoid and myeloid progenitor populations", J. Exp. Med. 200(11), 2004, pp. 1519-1524.
Cools, N., "Balancing between immunity and tolerance: an interplay between dendritic cells, regulatory T cells, and effector T cells", J. Leukoc. Biol. 82(6), 2007, 1365-74.
Denfeld, R., "UVB-irradiated dendritic cells are impaired in their APC function and tolerize primed Th1 cells but not naive CD4+ T cells", J. Leukoc. Biol. 69, 2001, 548-54.
Dudda, J., "UVB-irradiated dendritic cells fail to tolerize murine CD8+ naïve or effector T cells", J. Invest. Dermatol. 122, 2004, 945-52.
Ebner, S., "Production of IL-12 by human monocyte-derived dendritic cells is optimal when the stimulus is given at the onset of maturation, and is further enhanced by IL-4", J. Immunol. 166, 2001, 633-41.

(Continued)

*Primary Examiner* — Scott Long
(74) *Attorney, Agent, or Firm* — Krista P. Kauppinen

(57) ABSTRACT

The invention provides methods of differentiating primate pluripotent stem cells into cells of hematopoietic lineage. The invention further provides hematopoietic lineage cells differentiated from primate pluripotent stem cells, as well as methods of using the same and kits comprising the same.

14 Claims, 19 Drawing Sheets

(56) References Cited

OTHER PUBLICATIONS

Fairchild, P., "Directed differentiation of dendritic cells from mouse embryonic stem cells", Curr. Biol. 10, 2000, 1515-8.
Fairchild, P., "Embryonic stem cells: a novel source of dendritic cells for clinical applications", Intl. Immunopharmacol. 5(1), 2005, 13-21.
Fehling, H., "Tracking mesoderm induction and its specification to the hemangioblast during embryonic stem cell differentiation", Development 130, 2003, 4217-27.
Guerriero, A., "PU.1 is required for myeloid-derived but not lymphoid-derived dendritic cells", Blood 95(3), 2000, 879-85.
Kaufman, D., "Hematopoietic Colony-Forming Cells Derived from Human Embryonic Stem Cells", Proc. Natl. Acad. Sci. USA 98(19), 2001, pp. 10716-10721.
Kennedy, M., "Development of the hemangioblast defines the onset of hematopoiesis in human ES cell differentiation cultures", Blood 109(7), 2007, 2679-87.
Li, F., "Bone morphogenetic protein 4 induces efficient hematopoietic differentiation of rhesus monkey embryonic stem cells in vitro", Blood 98, 2001, pp. 335-342.
Li, Y., "Expansion of human embryonic stem cells in defined serum-free medium devoid of animal-derived products", Biotechnol. Bioeng. 91(6), 2005, pp. 688-698.
Loges, S., "Identification of the adult human hemangioblast", Stem Cells Dev. 13(1), 2004, pp. 229-242.
Lu, S., "CD34+CD38− hematopoietic precursors derived from human embryonic stem cells exhibit an embryonic gene expression pattern", Blood 103(11), 2004, pp. 4134-4141.
Mayordomo, J., "Bone marrow-derived dendritic cells pulsed with synthetic tumour peptides elicit protective and therapeutic antitumour immunity", Nature Med. 1, 1995, pp. 1297-1302.
Merrick, A., "Immunosuppressive effects of radiation on human dendritic cells: reduced IL-12 production on activation and impairment of naive T-cell priming", Br. J. Cancer 92, 2005, pp. 1450-1458.
Ng, E., "Forced aggregation of defined Nos. Of human embryonic stem cells into embryoid bodies fosters robust, reproducible hematopoietic differentiation", Blood 106(5), 2005, pp. 1601-1603.
Nutt, S., "Dynamic regulation of PU.1 expression in multipotent hematopoietic progenitors", J. Exp. Med. 201(2), 2005, pp. 221-231.
Pick, M., "Differentiation of human embryonic stem cells in serum-free medium reveals distinct roles for bone morphogenetic protein 4, vascular endothelial growth factor, stem cell factor, and fibroblast growth factor 2 in hematopoiesis", Stem Cells 25, 2007, pp. 2206-2214.
Reubinoff, B., "Embryonic stem cells lines from human blastocysts: somatic differentiation in vitro", Nature Biotechnol. 18, 2000, pp. 399-404.
Rissoan, M., "Subtractive hybridization reveals the expression of immunoglobulin-like transcript 7, Eph-B1, granzyme B, and 3 novel transcripts in human plasmacytoid dendritic cells", Blood 100(9), 2002, pp. 3295-3303.
Schotte, R., "The ETS transcription factor Spi-B is required for human plasmacytoid dendritic cell development", J. Exp. Med. 200(11), 2004, pp. 1503-1509.
Schotte, R., "The transcription factor Spi-B is expressed in plasmacytoid DC precursors and inhibits T-, B-, and NK-cell development", Blood 101(3), 2003, pp. 1015-1023.
Senju, S., "Genetically manipulated human embryonic stem cell-derived dendritic cells with immune regulatory function", Stem Cells 25(11), 2007, pp. 2720-2729.
Shamblott, M. et al., "Derivation of pluripotent stem cells from cultured human primordial germ cells," Proc. Natl. Acad. Sci. USA 95, (1998), pp. 13726-13731.
Slukvin, I., "Directed differentiation of human embryonic stem cells into functional dendritic cells through the myeloid pathway", J. Immunology 176, 2006, pp. 2924-2932.
Su, H., "Vaccination against chlamydial genital tract infection after immunization with dendritic cells pulsed ex vivo with nonviable Chlamydiae", J. Exp. Med. 188, 1998, 809-18.
Su, Z., "Differentiation of human embryonic stem cells into immunostimulatory dendritic cells under feeder-free culture conditions", Clin. Cancer Res. 14(19), 2008, pp. 6207-6217.
Tacken, P., "Dendritic-cell immunotherapy: from ex vivo loading to in vivo targeting", Nature Rev. Immunol. 7, 2007, pp. 790-802.
Takahashi, K. et al., "Induction of pluripotent stem cells from adult human fibroblasts by defined factors," Cell 131(5), (2007), pp. 861-872.
Thomson, J. et al., "Embryonic stem cell lines derived from human blastocysts," Science 282, (1998), pp. 1145-1147.
Thomson, J. et al., "Isolation of a primate embryonic stem cell line," Proc. Natl. Acad. Sci. USA 92, (1995), pp. 7844-7848.
Thomson, J. et al., "Pluripotent cell lines derived from common marmoset (*Callithrix jacchus*) blastocysts," Biol. Reprod. 55, (1996), pp. 254-259.
Thomson, J., "Primate embryonic stem cells", Curr. Top. Dev. Biol. 38, 1998, pp. 133-165.
Tseng, S-Y., "Generation of immunogenic dendritic cells from human embryonic stem cells without serum and feeder cells", Regen. Med. 4(4), 2009, pp. 513-526.
Vodyanik, M., "Directed differentiation of human embryonic stem cells to dendritic cells", Methods in Molecular Biology, Humana Press, Totowa, NJ, 2007, pp. 275-293.
Xu, C., "Feeder-free growth of undifferentiated human embryonic stem cells", Nature Biotech. 19, 2001, 971-4.
Young, J., "High-dose UV-B radiation alters human dendritic cell costimulatory activity but does not allow dendritic cells to tolerize T lymphocytes to alloantigen in vitro", Blood 81(11), 1993, pp. 2987-2997.
Yu, J. et al., "Induced pluripotent stem cell lines derived from human somatic cells," Science 318, (2007), pp. 1917-1720.
Zambidis, E., "Hematopoietic differentiation of human embryonic stem cells progresses through sequential hematoendothelial, primitive, and cells progresses through sequential hematoendothelial, primitive, an definitive stages resembling human yolk sac development", Blood 106(3), 2005, pp. 860-870.
Zhan, X., "Functional antigen-presenting leucocytes derived from human embryonic stem cells in vitro", Lancet 364, 2004, pp. 163-171.

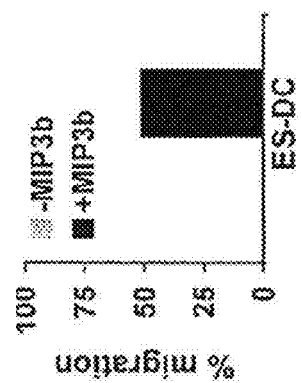
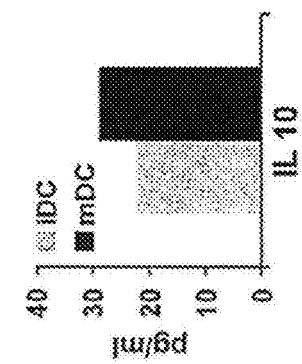
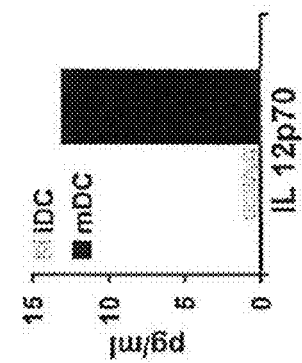
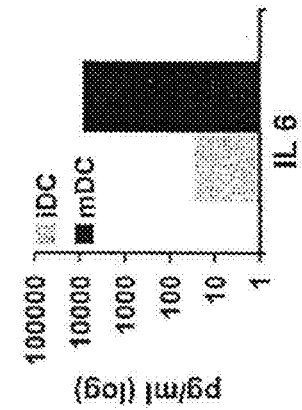

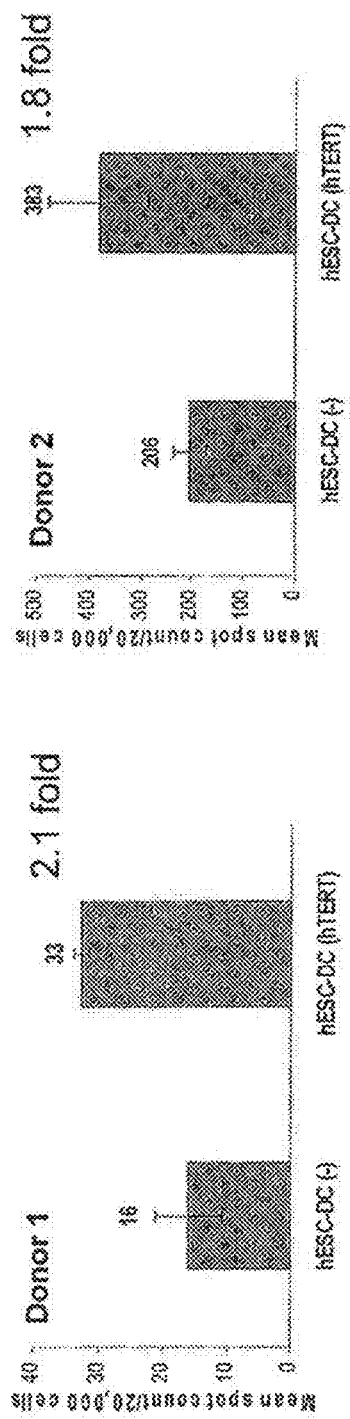
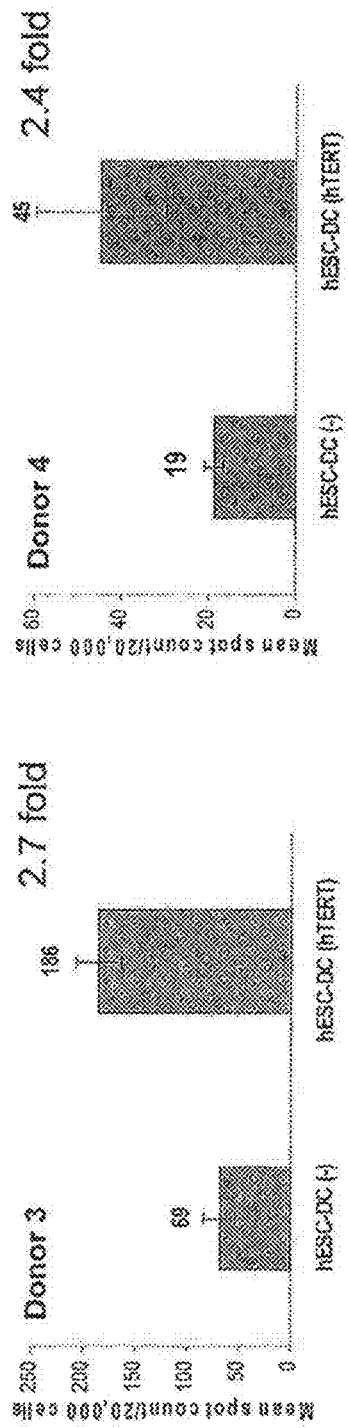
FIG. 8A, FIG. 8B, FIG. 8C, FIG. 8D
Mature hESC-DC present hTERT antigen on HLA-A2 and stimulate IFN-g secretion from T cells

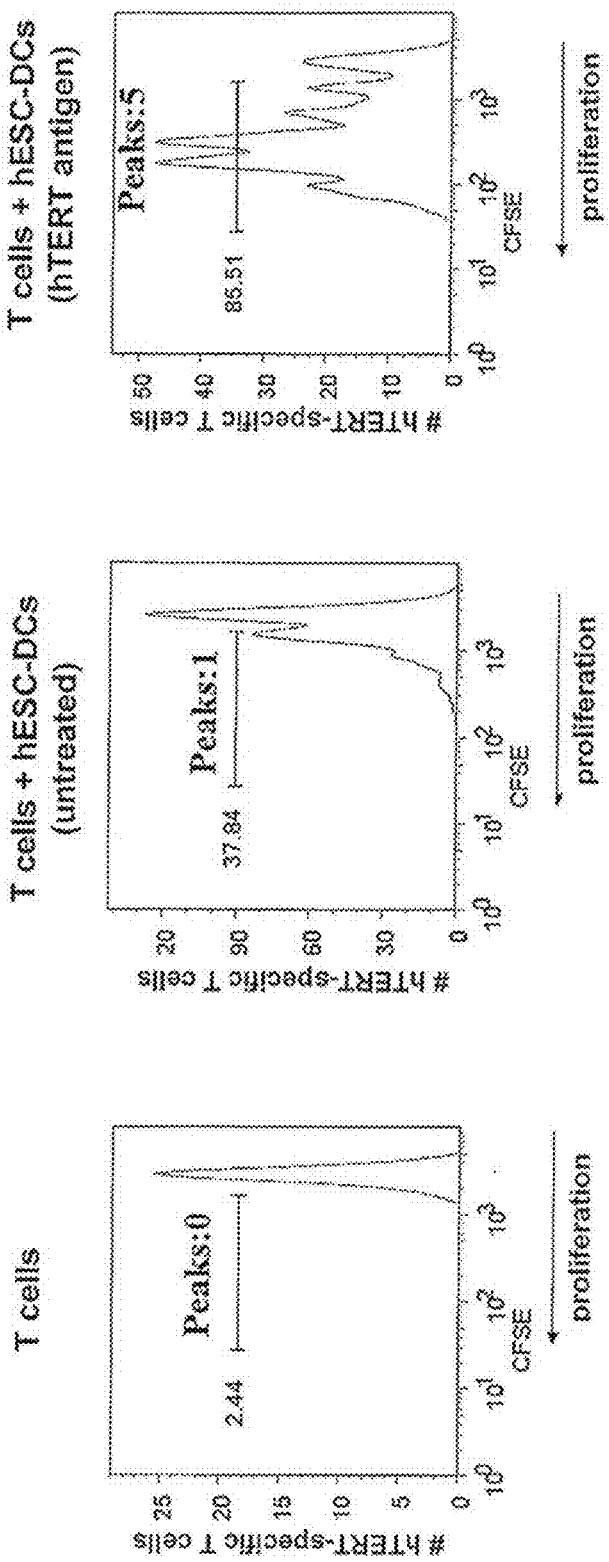

DIFFERENTIATION OF PRIMATE PLURIPOTENT STEM CELLS TO HEMATOPOIETIC LINEAGE CELLS

This application is a continuation of U.S. application Ser. No. 13/312,349, filed Dec. 6, 2011 (now abandoned), which is a continuation of U.S. application Ser. No. 12/412,183, filed Mar. 26, 2009 (now U.S. Pat. No. 8,093,049), which claims benefit of U.S. Provisional Application No. 61/039,835, filed Mar. 27, 2008 and claims benefit of U.S. Provisional Application No. 61/081,242, filed Jul. 16, 2008. All of the above priority applications are hereby incorporated by reference in their entireties.

FIELD OF THE INVENTION

The invention relates to the field of stem cell biology.

BACKGROUND

Pluripotent stem cells have the ability to both proliferate continuously in culture and, under appropriate growth conditions, differentiate into lineage restricted cell types representative of all three primary germ layers: endoderm, mesoderm and ectoderm (U.S. Pat. Nos. 5,843,780; 6,200,806; 7,029,913; Shamblott et al., (1998) *Proc. Natl. Acad. Sci. USA* 95:13726; Takahashi et al., (2007) Cell 131(5):861; Yu et al., (2007) Science 318:5858). Defining appropriate growth conditions for particular lineage restricted cell types will provide virtually an unlimited supply of that cell type for use in research and therapeutic applications.

It would be particularly useful to be able to differentiate pluripotent stem cells into hematopoietic lineage cells. Hematopoietic lineage cells develop from the mesoderm layer and include both white and red blood cells, which constitute the immune and circulatory systems, respectively. An unlimited supply of these cells would provide the tools necessary to more fully understand both the development and functioning of both the immune and circulatory systems. It would also provide insight into strategies for modulating immune responses, both beneficial and harmful.

The immune system provides for an innate or non-specific immune response as well as an adaptive or specific immune response. The adaptive immune response is a long lasting protective response and it is this response most vaccine protocols seek to stimulate. Cellular participants in the adaptive immune response include lymphocytes (T cells and B cells) as well as dendritic cells (DC). T cells and B cells eliminate target pathogens by specifically recognizing antigenic epitopes expressed on the pathogen. T cells have cytotoxic capability that is especially adept at targeting virally infected and tumor cells. B cells secrete antibodies which bind target antigens and activate the complement system facilitating opsonization and lysis of the target. Both responses are characterized as memory responses and thus are protective over a period of time. DC play an important role in initiating the adaptive immune response. They present antigen to the lymphocytes in the context of the appropriate major histocompatibility complex (MHC) and thus provide the initial stimulus for mounting the adaptive immune response. A ready supply of DC could provide a means for generating either a therapeutic or prophylactic immune response in a host.

A number of studies have demonstrated the potential of DC as vehicles for generating an adaptive immune response (see, e.g., Mayordomo et al., (1995) *Nature Med* 1:1297; Celluzi et al., (1996) *J. Exp. Med.* 183:283; Su et al., (1998) *J. Exp. Med.* 188:809) including studies that have investigated the effects of irradiating DC (see, e.g., Cao et al. (2004) *Cell Biology International* 28:223; Merrick et al., (2005) *British Journal Of Cancer* 92:1450; Young et al. (1993) *Blood* 81(11):2987; Denfield et al. (2001) *Journal Of Leukocyte Biology* 69:548; Dudda et al. (2004) *Journal of Investigative Dermatology* 122:945).

The potential of dendritic cells along with the promise of pluripotent stem cells have lead several investigators to attempt to differentiate pluripotent stem cells into DC or their precursors (see, e.g. U.S. Pat. No. 7,247,480; U.S. Patent Publication Nos.: 2002/0086005; 2003/0153082; 2006/0275901; 2006/0147432; 2006/0063255; 2006/0147432; Fairchild et al., (2005) *International Immunopharmacology* 5:13; Tacken et al., (2007) *Nature Reviews Immunology* 7:790; Senju et al., (2007) *Stem Cells* 25(11):2720; Sluvkin et al., (2006) *J of Immunology* 176:2924; Li et al., (2001) *Blood* 98(2):335; Kaufman et al., (2001) *Proc Natl Acad Sci* 98(19):10716; Chadwick et al., (2003) *Blood* 102(3):906; Zhan et al., (2004) *Lancet* 364:163; Fairchild et al., (2000) *Current Biology* 10:1515; Kennedy et al., (2007) *Blood* 109(7):2679; Ng et al., (2005) *Blood* 106(5):1601; Fehling et al., (2003) *Development* 130:4217; Lu et al., (2004) *Blood* 103(11):4134; Zambidis et al., (2005) *Blood* 106(3):860; Bandi et al., (2008) *AIDS Research and Therapy* 5:1; Pick et al., (2007) *Stem Cells* 25:2206).

Many of these investigators relied on stromal cells and/or feeder cells to grow and/or differentiate their stem cells. The use of feeder cells and stromal cells is cumbersome, expensive, time consuming and difficult to scale up. Some of these investigators used animal products such as animal serum in their protocols. Using animal products, however, carries with it the risk of contamination of the cells with zoogenic infectious agents. Still other investigators relied on random or poorly formulated differentiation protocols resulting in unpredictable outcomes and generally low yield of product.

There is a need for hematopoietic lineage cells differentiated from pluripotent stem cells and for methods of producing these cells that is scalable, economical, efficient, reliable, safe, and capable of providing good yield of product. Various embodiments of the invention described herein meet these needs and other needs as well.

SUMMARY OF THE INVENTION

In certain embodiments the invention provides for the in vitro differentiation of primate pluripotent stem cells (pPS) into hematopoietic lineage cells. The pPS cells may be human pluripotent stem cells that are suitable for differentiation into human hematopoietic lineage cells. The hematopoietic lineage cell may include, for example, an immature dendritic cell (imDC), a mature dendritic cell (mDC), a myeloid precursor cell, a monocyte.

In certain other embodiments the invention provides a method for the in vitro differentiation of pPS cells into mesoderm cells.

Differentiation of pPS cells into hematopoietic lineage cells may include contacting cells in vitro, e.g. pPS cells, with a differentiation cocktail comprising a plurality of exogenous cytokines, and/or a plurality of exogenous ligands to proteins expressed on the cell surface (including, for example, exogenous ligands to cytokine receptors such as an antibody which specifically binds to the cytokine receptor), such that the cell population differentiates into a cell having a different phenotype, e.g. the phenotype of a hematopoietic lineage cell, while maintaining essentially the same genotype. Suitable exogenous cytokines may include a plurality of the following: granulocyte-macrophage colony stimulating factor (GM-CSF), bone morphogenic protein 4 (BMP-4), vascular endothelial growth factor (VEGF), stem cell factor (SCF), thrombopoietin (TPO), fetal liver kinase ligand (FLT3L), interleukin 4 (IL-4) and interleukin 3 (IL-3).

Reference to the cells having the same genotype is not intended to imply that the cells cannot be genetically manipulated by the human hand (embodiments encompassing genetically altered cells are described infra), or that very minor changes (e.g., less than a fraction of a percent of the entire genome) might occur spontaneously (e.g. in the non-coding regions), but rather merely to suggest that the act of differentiating the cells from pPS cells into cells of hematopoietic lineage will not, by itself, result in an altered genotype. Typically the genetic identity between a parental (undifferentiated cell) and its differentiated progeny will be similar to the genetic identity found between identical twins.

In certain embodiments the method of in vitro differentiation of pPS cells into hematopoietic lineage cells may be practiced serum free. In some embodiments the method of differentiation of pPS cells into hematopoietic lineage cells may be practiced feeder free. In various embodiments the method of differentiation of pPS cells into hematopoietic lineage cells may be practiced stromal cell free. In certain embodiments the method of differentiation of pPS cells into hematopoietic lineage cells may be practiced without the addition of exogenous IL-3 or the addition of an exogenous ligand to the IL-3 receptor.

In some embodiments the invention provides a method of differentiating pPS cells in vitro into imDC comprising contacting the pPS cells with a plurality of exogenous cytokines comprising GM-CSF and BMP-4. The plurality of exogenous cytokines may further include one or more of the following: VEGF, SCF, TPO, FLT3L, and IL-3. In some embodiments IL-4 may also be included in this differentiation cocktail.

In yet other embodiments the invention provides a method of differentiating pPS cells in vitro into mDC comprising 1) contacting the pPS cells with a differentiation cocktail comprising a plurality of exogenous cytokines, and/or a plurality of exogenous ligands to a protein expressed on the cell surface, e.g., to a cytokine receptor, suitable for differentiating pPS cells to imDC thereby differentiating pPS cells into imDC; and 2) contacting the imDC with a maturation cocktail comprising a plurality of exogenous cytokines, and/or exogenous ligands to a protein expressed on the cell surface, e.g., to a cytokine receptor, suitable for facilitating the maturation of the imDC to mDC thereby differentiating the imDC into mDC. The differentiation cocktail may comprise a plurality of the following: GM-CSF, VEGF, BMP-4, SCF, TPO, FLT3L and IL-3. The maturation cocktail may comprise a plurality of the following: tumor necrosis factor α (TNFα), interleukin 1β (IL1β), interferon γ (IFNγ), prostaglandin E2 (PGE2), polyinosinic: polycytidylic acid (POLY I:C), interferon α (IFNα), CD40L and GM-CSF.

In one embodiment the invention provides a method of differentiating pPS cells in vitro into mDC comprising contacting the pPS cells with a differentiation cocktail comprising BMP-4, GM-CSF, VEGF and SCF and a suitable maturation cocktail, e.g., a maturation cocktail comprising GM-CSF, IFNγ, TNFα, IL1β, and PGE2. In this embodiment IL-4 may also be included in the differentiation cocktail.

In some embodiments the composition of the differentiation cocktail may stay the same over the course of the differentiation of pPS cells to hematopoietic lineage cells. For example the differentiation cocktail may comprise BMP-4, GM-CSF, VEGF and SCF through out the course of differentiating the pPS cells to imDC. In some embodiments IL-4 may also be included in the differentiation cocktail.

In other embodiments the composition of the differentiation cocktail may change over the course of the differentiation protocol. Thus in some embodiments of the invention the differentiation cocktail may comprise 4 exogenous cytokines, or 4 exogenous ligands to cell surface proteins for one or more steps of the protocol while in other steps of the differentiation protocol the differentiation cocktail may comprise 3, 2, or 1 exogenous cytokine(s) or exogenous ligand(s) to a cell surface protein. For example the cells may be contacted first with a differentiation cocktail comprising BMP-4, VEGF and SCF (GM-CSF may optionally be included in this first step), followed by a differentiation cocktail comprising VEGF, SCF and GM-SCF, followed by a differentiation cocktail comprising SCF and GM-CSF, followed by a differentiation cocktail comprising GM-CSF, followed by a differentiation cocktail comprising GM-CSF and interleukin 4 (IL-4), thus differentiating pPS cells into imDC. The imDC may then be contacted with a suitable maturation cocktail, e.g., a maturation cocktail comprising IFNγ, TNFα, IL1β, and PGE2.

In still further embodiments the invention provides a method of differentiating pPS cells in vitro into cells expressing one or more of the following: CD83, CD14, MHC I, MHC II, CD11c and CD11b comprising contacting the pPS cells with a plurality of the following: GM-CSF, BMP-4, VEGF, SCF, FLT3L, TPO, and IL-3 and/or exogenous ligands to a cell surface protein.

In yet further embodiments the invention provides a method of differentiating in vitro a cell expressing stage specific embryonic antigen 3 (SSEA3), stage specific embryonic antigen 4 (SSEA4) and markers detectable using antibodies designated Tra-1-60, and Tra-1-81 into cells expressing one or more of the following: CD83, CD14, MHC I, MHC II, CD11c and CD11b comprising contacting the pPS cells with a plurality of the following: GM-CSF, BMP-4, VEGF, SCF, FLT3L, TPO, and IL-3 and/or exogenous ligands to a cell surface protein.

In still further embodiments the invention provides a method of differentiating pPS cells in vitro into cells expressing CD83 CD14, MHC I, MHC II, CD11c and CD11b comprising contacting the pPS cells with a plurality of exogenous cytokines comprising GM-CSF and BMP-4 and/or an exogenous ligand to a cell surface receptor. The plurality of exogenous cytokines may further include one or more of the following: VEGF, SCF, FLT3L, TPO, and IL-3 and/or exogenous ligands to a cell surface protein. Examples of cell surface proteins may include a receptor for one of the previously mentioned cytokines.

In some embodiments the invention provides a method of differentiating pPS cells in vitro into cells expressing one or more of the following: MHC-I, MHC-II, CD83, CD205, CD11b, CCR7, CD40, CD86, CD123, CD11c comprising contacting the pPS cells with 1) a differentiation cocktail and then contacting the cells of 1) with a maturation cocktail. The differentiation cocktail may comprise a plurality of the following: GM-CSF, BMP-4 VEGF, SCF, FLT3L, TPO, IL-4 and IL-3 and/or exogenous ligands to a cell surface protein. The maturation cocktail may comprise a plurality of the following: GM-CSF, TNFα, IL1β, IFNγ, PGE2, POLY I:C, IFNα and/or exogenous ligands to a cell surface protein. Examples of cell surface proteins may include a receptor for one of the previously mentioned cytokines.

In certain embodiments the invention provides a method of differentiating pPS cells in vitro into cells expressing CD83 comprising contacting the pPS cells with a differentiation cocktail and a maturation cocktail. The differentiation cocktail may comprise GM-CSF and BMP-4 and/or an exogenous ligand to a cell surface receptor. In some embodiments the differentiation cocktail may further include one or more of the following: VEGF, SCF, FLT3L, TPO, IL-4 and IL-3. The maturation cocktail may comprise a plurality of the following: TNFα, IL1β, PGE2, POLY I:C, IFNα, CD40L and GM-CSF. In some embodiments the cell expressing CD83 may also express one or more of the following CD86, CD14, CD11b, CD11c, CD205, MHC I and MHC II. In some embodiments the differentiation cocktail may comprise exogenous ligands to a cell surface protein, such as a cytokine receptor.

In still other embodiments the invention provides a method of differentiating pPS cells in vitro into a population of cells expressing CD45 and CD11c comprising contacting the pPS cells with a plurality of exogenous cytokines comprising GM-CSF and BMP-4 and/or an exogenous ligand to a cell surface receptor. In some embodiments the plurality of exogenous cytokines may further include one or more of the following: VEGF, SCF, FLT3L, TPO, and IL-3 and/or exogenous ligands to a cell surface protein. The CD45 expressing cells maybe $CD45^{hi}$ cells.

In further embodiments the invention provides a method of differentiating in vitro a cell expressing stage specific embryonic antigen 3 (SSEA3), stage specific embryonic antigen 4 (SSEA4) and markers detectable using antibodies designated Tra-1-60, and Tra-1-81 into into a population of cells expressing CD45 and CD11c comprising contacting the cell expressing stage specific embryonic antigen 3 (SSEA3), stage specific embryonic antigen 4 (SSEA4) and markers detectable using antibodies designated Tra-1-60, and Tra-1-81 with a plurality of exogenous cytokines comprising GM-CSF and BMP-4 and/or an exogenous ligand to a cell surface receptor. In some embodiments the plurality of exogenous cytokines may further include one or more of the following: VEGF, SCF, FLT3L, TPO, and IL-3 and/or exogenous ligands to a cell surface protein. The CD45 expressing cells maybe $CD45^{hi}$ cells.

Reference to differentiating cells expressing one or more markers may include embodiments where expression of the referenced marker is increased (e.g. as a result of the differentiation) when compared to a starting cell population (e.g. a precursor cell population with respect to the differentiated cell population).

In further embodiments the invention provides a method of differentiating pPS cells in vitro into mesoderm comprising contacting the pPS cells with a differentiation cocktail comprising a plurality of exogenous cytokines. The differentiation cocktail may include a plurality of the following: BMP-4, VEGF, SCF, FLT3L and GM-CSF and/or exogenous ligands to a cell surface protein. In one embodiment the differentiation cocktail may comprise BMP-4, VEGF, SCF.

In other embodiments the invention provides a cell culture comprising a first population of cells comprising pPS cells and second population of cells comprising a hematopoietic lineage cell. Hematopoietic lineage cells may include one or more of the following: hemangioblasts, hematopoietic stem cells, myeloid progenitor cells, granulomonocytic progenitor cells, monocytes, imDC and mDC. In some embodiments the cell culture may comprise a plurality of exogenous cytokines and/or ligands to cell surface proteins such as cytokine receptors. Suitable exogenous cytokines may include the following: GM-CSF, VEGF, BMP-4, SCF, FLT3L, IL-4, TPO, TNFα, IL1β, IFNγ, PGE2, POLY I:C, IFNα. The cell culture may also comprise exogenous CD40L. In some embodiments the cell culture may optionally not comprise exogenous IL-3 or an exogenous ligand to the IL-3 receptor. In some embodiments the cell culture may be feeder free. In some embodiments the cell culture may be stromal cell free. In some embodiments the cell culture may be serum free.

In yet other embodiments the invention provides a cell culture comprising a first population of cells comprising pPS cells and second population of cells comprising a DC, e.g., an mDC, an imDC. In some embodiments the cell culture may comprise a plurality of exogenous cytokines. Suitable exogenous cytokines may include the following: GM-CSF, VEGF, BMP-4, SCF, TPO, TNFα, FLT3L, IL1β, IL-4, IFNγ, PGE2, POLY I:C, IFNα. The cell culture may also comprise exogenous CD40L. In one embodiment the invention provides a cell culture comprising a first population of cells comprising pPS cells and second population of cells comprising a DC, e.g., an mDC, an imDC and exogenous BMP-4 and GM-CSF. In some embodiments the cell culture may optionally not comprise exogenous IL-3 or an exogenous ligand to the IL-3 receptor. In some embodiments the cell culture may be feeder free. In some embodiments the cell culture may be stromal cell free. In various embodiments the cell culture may be serum free. In certain embodiments the cell culture may be irradiated. For example, an irradiated cell culture may include a cell culture comprising mDC. The irradiated cell culture may also comprise at least one pPS cell. In other embodiments the cells may be contacted with a chemical agent suitable for inhibiting cell division such as a chemotherapeutic, e.g., mitomycin, cisplatin.

In further embodiments the invention provides a method of inhibiting cell division in a cell culture comprising contacting the cell culture with a source of radiation or a chemical agent, wherein the cell culture comprises at least one pPS cell and mDC differentiated in vitro from pPS cells.

In still other embodiments the invention provides a method of making an immuno-modulating preparation comprising 1) differentiating at least a portion of a population of pPS cells into mDC cells thereby obtaining a mixed population of cells comprising mDC and at least one pPS cell and 2) contacting the mixed population of cells of 1) with a radiation source or a chemical agent thereby obtaining an immuno-modulating preparation. The method may further comprise contacting the mixed population of cells comprising mDC with an antigen, e.g. a protein or a peptide. The population of cells may be contacted with an antigen before the cells are contacted with the radiation. The immuno-modulating preparation may stimulate an immune response to an antigen.

In further embodiments the invention provides a method of making an immuno-modulating preparation comprising 1) differentiating at least a portion of a population of pPS cells into a population comprising imDC cells thereby obtaining a mixed population of cells comprising imDC and at least one pPS cell; 2) contacting the population of cells comprising imDC with a nucleic acid encoding an antigen; 3) contacting the population of cells of 2) with a maturation cocktail such that the imDC mature into mDC wherein the population comprises at least one pPS cell and 4) contacting the mixed population of cells of 3) with a radiation source or a chemical agent thereby obtaining an immuno-modulating preparation. The immuno-modulating preparation may stimulate an immune response to antigen.

In yet other embodiments the invention provides a method of making an immuno-modulating preparation comprising 1) differentiating at least a portion of a population of pPS cells into a population comprising imDC cells thereby obtaining a mixed population of cells comprising mDC and at least one pPS cell; 2) contacting the population of cells of 1) with a maturation cocktail such that the imDC mature into mDC, wherein the population of cells comprises at least one pPS cell 3) contacting the population of cells comprising mDC with a nucleic acid encoding an antigen; and 4) contacting the mixed population of cells of 3) with a radiation source or a chemical agent thereby obtaining an immuno-modulating preparation. The immuno-modulating preparation may stimulate an immune response to antigen.

In still other embodiments the invention provides an immuno-modulating composition comprising a mitotically inactivated mDC which is the in vitro progeny of a pPS cell. The composition may be irradiated or treated with a chemical agent suitable for inhibiting cell division such as a chemotherapeutic, e.g. mitomycin, cisplatin in order to mitotically inactivate the cells. In some embodiments the immuno-modulating composition may comprise a DC e.g. an mDC or an imDC contacted with an antigen or a nucleic acid encoding an antigen prior to irradiation. The immuno-modulating response may be one that stimulates an immune response to an antigen.

In other embodiments the invention provides a method of stimulating an immune response to an antigen comprising a) obtaining an mDC differentiated in vitro from a pPS cell; b) contacting the mDC with an antigen or a nucleic acid molecule that encodes an antigen; c) contacting the mDC of b) with a radiation source or a chemical agent suitable for inhibiting cell division, e.g. mitomycin; d) contacting the mDC of c) with an immunologically competent cell thereby stimulating an immune response to the antigen.

In other embodiments the invention provides a method of stimulating an immune response to an antigen comprising a) obtaining an imDC differentiated in vitro from a pPS cell; b) contacting the imDC with a nucleic acid molecule that encodes an antigen; c) contacting the imDC with a maturation cocktail (as described herein) such that the imDC matures into an mDC d) contacting the mDC of c) with a radiation source or a chemical agent suitable for inhibiting cell division, e.g. mitomycin; e) contacting the mDC of d) with an immunologically competent cell thereby stimulating an immune response to the antigen.

In other embodiments the invention provides a method of stimulating an immune response to an antigen comprising a) contacting a pPS cell with a differentiation cocktail and a maturation cocktail such that the pPS differentiates into an mDC; b) contacting the mDC of a) with an antigen or a nucleic acid molecule that encodes an antigen; c) contacting the mDC of b) with an immunologically competent cell thereby stimulating an immune response to the antigen. The differentiation cocktail may comprise a plurality of exogenous cytokines and/or a plurality of exogenous ligands to cell surface proteins. The differentiation cocktail may comprise GM-CSF, BMP-4, VEGF, SCF, FLT3L, TPO, IL-4 and IL-3. The maturation cocktail may comprise one or more of the following: GM-CSF, TNF-α, IL1β, IFNγ, PGE2, POLY I:C, IFNα. In some embodiments the cell culture may optionally not comprise exogenous IL-3 or an exogenous ligand to the IL-3 receptor. In some embodiments the cell culture may be feeder free. In some embodiments the cell culture may be stromal cell free. In some embodiments the cell culture may be serum free.

In still other embodiments the invention provides a kit for stimulating an immune response to an antigen comprising 1) a cell culture comprising pPS cells and DC and 2) one or more containers. The DC may be mDC or imDC. The cell culture may comprise exogenous cytokines and/or or exogenous ligands to cell surface proteins. The exogenous cytokines and/or or exogenous ligands to cell surface proteins may include a plurality of the following: GM-CSF, VEGF, BMP-4, SCF, FLT3L, TPO, IL-4, IL-3, TNFα, IL1β, IFNγ, PGE2, POLYI:C, IFNα, CD40L. In some embodiments the cell culture may optionally not comprise exogenous IL-3 or an exogenous ligand to the IL-3 receptor. In some embodiments the cell culture may be feeder free. In some embodiments the cell culture may be stromal cell free. In some embodiments the cell culture may be serum free.

In yet other embodiments the invention provides a kit for stimulating an immune response to an antigen comprising 1) an irradiated mDC which is the in vitro progeny of a pPS cell and 2) one or more containers.

In still other embodiments the provides a kit for stimulating an immune response to an antigen comprising 1) a mitotically inactivated mDC which is the vitro progeny of a pPS cell; and 2) one or more containers. The mDC may be contacted with a chemical agent suitable for inhibiting cell division to mitotically inactivate the cells. A suitable chemical for inhibiting cell division may include mitomycins such as mitomycin C. Alternatively the mDC may be contacted with a radiation source to mitotically inactivate the cells.

In further embodiments the invention provides a system for the production of mitotically inactive antigen presenting cells comprising a) a first isolated cell population comprising pPS cells and b) a second isolated cell population comprising mitotically inactivated mature dendritic cells which are the in vitro progeny of a portion of the pPS cells. The mature dendritic cells may be mitotically inactivated by irradiation or by contact with a chemical agent. It is contemplated that the first isolated cell population comprising the pPS cells (e.g. the portion not used to make the mDC) may be used to make more of the second isolated population by differentiating the first population of cells in vitro.

It is contemplated that any of the embodiments of the invention may be practiced by substituting one or more of the following sub-groupings of pPS cells: human embryonic stem cells, human embryonic germ cells, rhesus stem cells, marmoset stem cells, nuclear transfer stem cells and/or induced pluripotent stem cells, all of which are described infra.

DESCRIPTION OF THE FIGURES

FIG. 6A, FIG. 6B and FIG. 6C are graphs comparing the cytokine profile of imDC and mDC.

FIG. 6D is a graph showing DC migration in response to MIP3β.

FIG. 8A, FIG. 8B, FIG. 8C and FIG. 8D are graphs showing stimulation of IFNγ secretion by effector T cells in response to an hTERT peptide antigen presented on HLA-A2 by mDC (hES-DC).

FIG. 9A, FIG. 9B, and FIG. 9C show flow cytometry analysis of CFSE labeled T lymphocyte proliferation in response to an hTERT peptide antigen presented on HLA-A2 by mDC.

DEFINITIONS

Figure 1A:
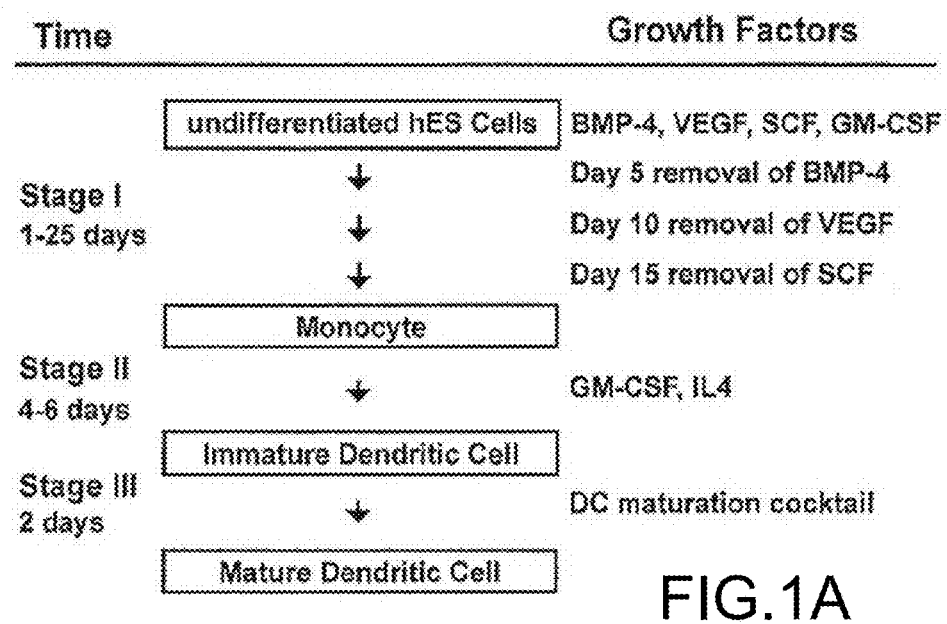
FIG. 1A provides a schematic diagram of one differentiation protocol used for differentiating pPS cells to mDC.

About, as used herein to refer to an amount or a value means + or −5% of stated amount or value.

Cell culture, as used herein, refers to a plurality of cells grown in vitro over time. The cell culture may originate from a plurality of pPS cells or from a single pPS cell and may include all of the progeny of the originating cell or cells, regardless of 1) the number of passages or divisions the cell culture undergoes over the lifetime of the culture; and 2) any changes in phenotype to one or more cells within the culture over the lifetime of the culture (e.g. resulting from differentiation of one or more pPS cells in the culture). Thus, as used herein, a cell culture begins with the initial seeding of one or more suitable vessels with at least one pPS cell and ends when the last surviving progeny of the original founder(s) is harvested or dies. Seeding of one or more additional culture vessels with progeny of the original founder cells is also considered to be a part of the original cell culture.

Cytokine, as used herein, refers to a molecule secreted by a cell that affects the behavior of another cell, or of the same cell, or both.

The term "embryoid bodies," as used herein, refers to heterogeneous clusters comprising undifferentiated, differentiated and partly differentiated cells that appear when primate pluripotent stem cells are allowed to differentiate in a non-specific fashion in suspension cultures or aggregates.

As used herein, "embryonic stem cell" (ES) refers to pluripotent stem cells that are derived from a blastocyst before substantial differentiation of the cells into the three germ layers. Except where explicitly required otherwise, the term includes primary tissue and established lines that bear phenotypic characteristics of ES cells, and progeny of such lines that still have the capacity of producing progeny cells bearing phenotypic traits of each of the three germ layers. The ES cells may be human ES cells (hES). Prototype "human Embryonic Stem cells" (hES cells) are described by Thomson et al. (*Science* 282:1145, 1998; U.S. Pat. No. 6,200,806) and include established cell lines described therein.

Exogenous as used herein refers to agents added to a system, such as a cell culture. The agent may be added to the system by the human hand.

As used herein, "feeder cells" refers to non-pPS cells that are co-cultured with pPS cells and provide support for the pPS cells. Support may include facilitating the growth and maintenance of the pPS cell culture by providing the pPS cell culture with one or more cell factors such that the pPS cells are maintained in a substantially undifferentiated state. Feeder cells may either have a different genome than the pPS cells or the same genome as the pPS cells and may originate from a non-primate species, such as mouse, or may be of primate origin, e.g., human. Examples of feeder cells may include cells having the phenotype of connective tissue such as murine fibroblast cells, human fibroblasts.

As used herein, "feeder-free" refers to a condition where the referenced composition contains no added feeder cells. To clarify, the term feeder-free encompasses, inter alia, situations where primate pluripotent stem cells are passaged from a culture which may comprise some feeders into a culture without added feeders even if some of the feeders from the first culture are present in the second culture.

Hematopoietic lineage cells, as used herein, refers to cells differentiated in vitro from pPS cells and/or their progeny and may include one or more of the following: hemangioblasts, hematopoietic stem cells, common lymphoid progenitor cells, lymphocytes, common myeloid progenitor cells (CMP), granulomonocytic progenitor cells (GMP), monocytes, macrophages, imDC and mDC.

Immunologically competent cell, as used herein, refers to a cell which is capable of responding to an antigen. The responses may include for example cell proliferation in response to antigen, secretion of one or more cytokines in response to an antigen, expression of one or more transcription factors in response to an antigen. Examples of an immunologically competent cell include lymphocytes.

In vitro progeny of a primate pluripotent stem cell, as used herein, refers to a cell that is differentiated in vitro from a pluripotent state to a non-pluripotent state e.g. an immature DC, a mature DC.

As used herein, "primate pluripotent stem cells" (pPS) refers to cells that may be derived from any source and that are capable, under appropriate conditions, of producing primate progeny of different cell types that are derivatives of all of the 3 germinal layers (endoderm, mesoderm, and ectoderm). pPS cells may have the ability to form a teratoma in 8-12 week old SCID mice and/or the ability to form identifiable cells of all three germ layers in tissue culture. Included in the definition of primate pluripotent stem cells are embryonic cells of various types including human embryonic stem (hES) cells, (see, e.g., Thomson et al. (1998) *Science* 282:1145) and human embryonic germ (hEG) cells (see, e.g., Shamblott et al., (1998) *Proc. Natl. Acad. Sci. USA* 95:13726); embryonic stem cells from other primates, such as Rhesus stem cells (see, e.g., Thomson et al., (1995) *Proc. Natl. Acad. Sci. USA* 92:7844), marmoset stem cells (see, e.g., (1996) Thomson et al., *Biol. Reprod.* 55:254), stem cells created by nuclear transfer technology (U.S. Patent Application Publication No. 2002/0046410), as well as induced pluripotent stem cells (see, e.g. Yu et al., (2007) *Science* 318:5858); Takahashi et al., (2007) *Cell* 131(5):861).

As used herein, "undifferentiated primate pluripotent stem cells" refers to a cell culture where a substantial proportion of primate pluripotent stem cells and their derivatives in the population display morphological characteristics of undifferentiated cells. It is understood that colonies of undifferentiated cells within the population may be surrounded by neighboring cells that are partly differentiated.

As used herein, "genetically altered", "transfected", or "genetically transformed" refer to a process where a polynucleotide has been transferred into a cell by any suitable means of artificial manipulation, or where the cell is a progeny of the originally altered cell and has inherited the polynucleotide. The polynucleotide will often comprise a transcribable sequence encoding a protein of interest, which enables the cell to express the protein at an elevated level or may comprise a sequence encoding a molecule such as siRNA or antisense RNA that affects the expression of a protein (either expressed by the unmodified cell or as the result of the introduction of another polynucleotide sequence) without itself encoding a protein. The genetic alteration is said to be "inheritable" if progeny of the altered cell have the same alteration.

Serum free, as used herein, refers tissue culture growth conditions that have no added animal serum such fetal bovine serum, calf serum, horse serum, and no added commercially available serum replacement supplements such as B-27. Serum free includes, for example, media which may comprise human albumin, human transferrin and recombinant human insulin.

Spontaneous differentiated pPS cells, as used herein, refers to pPS cells within a cell culture which randomly and spontaneously differentiate to a non-pPS phenotype, i.e. express one or more markers not expressed on pPS cells and/or fail to express one or more markers expressed on a pPS cell.

Stromal cell, as used herein, refers to a cell which may be co-cultured with another population, e.g. a pPS cell population in order to facilitate the differentiation of the pPS cell population to a desired phenotype, e.g. hematopoietic lineage cells by providing one or more cell factors. Stromal cells may be derived from the bone marrow of a mammal. OP9 and S17 cells are examples of stromal cells.

Stromal cell free, as used herein, means that stromal cells, or media conditioned by stromal cells is not added to either the culture of undifferentiated pPS cells or to a culture of pPS cells that are differentiating to hematopoietic lineage cells.

MHC-I and HLA-I are used interchangeably, as are MHC-II and HLA-II.

DETAILED DESCRIPTION OF THE INVENTION

In certain embodiments the invention provides for improved methods for the in vitro differentiation of pPS cells into hematopoietic lineage cells. Thus certain embodiments of the invention provide for defined conditions requiring a minimal number of exogenous factors (such as cytokines) suitable for differentiating pPS cells into hematopoietic lineage cells such as DC (including imDC and mDC). In some embodiments the invention provides for contacting the pPS cells with a differentiation cocktail comprising a minimal number of exogenous cytokines, e.g. no more 7, no more 6, no more 5, no more 4, no more than 3 exogenous cytokines thereby generating hematopoietic lineage cells. In one embodiment the defined conditions may provide a differentiation cocktail comprising no more than four added exogenous cytokines, e.g. BMP-4, GM-CSF, SCF and VEGF. In other embodiments the defined conditions may provide for a differentiation cocktail comprising no more than three added exogenous cytokines, e.g., a) BMP-4, GM-CSF, SCF; b) BMP-4, GM-CSF, VEGF. In some embodiments a ligand to the respective cytokine receptor may be substituted for the respective cytokine and/or provided in addition to the respective cytokine. In embodiments where the hematopoietic cells are imDC, the differentiation cocktail may further comprise IL-4. The imDC may be further contacted with a maturation cocktail to produce mDC.

In some embodiments the invention provides for simplified culture conditions for differentiating pPS cells to hematopoietic lineage cells such as DC. Simplified culture conditions may include differentiating pPS cells to DC in a tissue culture that is serum free, feeder free, stromal cell free and optionally does not require the addition of exogenous IL-3. Differentiation of pPS to hematopoietic lineage cells may be performed by directly plating the pPS on a suitable solid surface thereby avoiding the necessity of forming an embryo body (EB). These simplified culture conditions eliminate the risk of exposure to infectious agents and also provide a faster and less expensive method of obtaining quantities of imDC cells that are sufficient for therapeutic and research applications.

Methods of Differentiating pPS Cells

Starting material for differentiating pPS cells into hematopoietic lineage cells include pPS cells which have been cultured serum free, feeder free and stromal cell free. Conditions for culturing pPS cells feeder free and serum free have been described see, e.g., Xu et al., (2001) *Nat Biotechnol* 19:971; Li et al., (2005) *Biotechnol Bioeng* 91:688. In some embodiments it may be advantageous to culture the pPS cells under conditions that are suitable for the formation of cellular aggregates, e.g. embryoid bodies (EB). The formation of EBs has been previously described see, e.g., U.S. Patent Publication No. 2006/0063255 and PCT Publication No. WO 01/51616. Briefly undifferentiated pPS cells may be harvested by collagenase treatment, dissociated into clusters or strips of cells, and passaged to non-adherent cell culture plates as aggregates. The harvested pPS cells may include some spontaneously differentiated cells. It is contemplated that the number of spontaneously differentiated cells may diminish over time as the cells form EBs and then differentiate into hematopoietic lineage cells. The aggregates may be fed with a suitable media, e.g. X-VIVO 10; X-VIVO 15. The pPS cells may be grown feeder free, serum free and stromal cell free both prior to and after formation of the EB.

In other embodiments the EB formation step may be skipped. Thus, pPS cells may be directly plated onto a suitable support, such as a tissue culture flask or well, and cultured in a media comprising a differentiation cocktail.

In various embodiments the invention provides methods of differentiating pPS cells into cells of hematopoietic lineage and/or mesoderm cells. The hematopoietic lineage cells may include imDC. In some embodiments the invention provides for a differentiation cocktail comprising a plurality of exogenously added cytokines suitable for differentiating pPS cells to hematopoietic lineage cells, e.g., BMP-4 and GM-CSF. Examples of differentiation cocktails may include any of the following: a) BMP-4, GM-CSF, VEGF, SCF, FLT3L, TPO and IL-3; b) BMP-4, GM-CSF, VEGF, SCF and FLT3L; c) BMP-4, GM-CSF, VEGF, and SCF; d) BMP-4, GM-CSF, SCF; and e) BMP-4, GM-CSF, VEGF. In certain embodiments IL-4 may be used in addition to the cytokines recited above. In some embodiments ligands to one or more cytokine receptors may be used in place of, or in addition to the cytokine.

It has also been discovered that various hematopoietic lineage cells may be obtained by adjusting the amount of time the cells are exposed to the differentiation cocktail. In some embodiments of the invention pPS cells cultured for about 5 days with a differentiation cocktail in order to differentiate the cells into a culture comprising mesoderm cells. In another embodiment of the invention pPS cells cultured for about 10 days with a differentiation cocktail in order to differentiate the cells into a culture comprising hematopoietic stem cells. In still another embodiment of the invention pPS cells cultured for about 15 days with a differentiation cocktail in order to differentiate the cells into a culture comprising a common myeloid progenitor cell. In yet another embodiment of the invention pPS cells cultured for about 20 days with a differentiation cocktail in order to differentiate the cells into a culture comprising granulo-monocytic progenitor cells. In still another embodiment of the invention pPS cells cultured for about 25 days with a differentiation cocktail in order to differentiate the cells into a culture comprising monocytes. In a further embodiment of the invention pPS cells cultured for about 30 days with a differentiation cocktail in order to differentiate the cells into a culture comprising imDC.

Some embodiments of the invention provide for maturing imDC to mDC by contacting the imDC with a suitable maturation cocktail comprising a plurality of exogenous cytokines. The maturation cocktail may comprise GM-CSF. Examples of suitable maturation cocktails include any of the following: a) GM-CSF, TNFα, IL-1β, IFNγ, and PGE2; b) GM-CSF, TNFα, IL-1β, IFNγ, PGE2 and CD40L; c) GM-CSF, TNFα, IL-1β, IFNγ, PGE2, POLY I:C, and IFNα; d) GM-CSF, TNFα, IL-1β, IFNγ, POLY I:C, and IFNα; e) GM-CSF, TNFα, IL-1β, IFNγ, POLY I:C, IFNα, and CD40L; f) TNFα, IL-1β, PGE2 and IL-6; g) GM-CSF, IL-1β, PGE2, and, IFNγ; h) GM-CSF, TNFα, PGE2, and, IFNγ; i) GM-CSF, IL-1β, IFNγ and CD40L. In some embodiments ligands to one or more cytokine receptors may be used in place of, and/or in addition to the cytokine. Other methods, known in the art, may be used to mature imDC to mDC. Examples include contacting imDC with lipopolysaccharide (LPS), contacting the imDC with CpG containing oligonucleotides, injecting the imDC into an area of inflammation within a subject.

The imDC may be cultured in the presence of the maturation cocktail, for at least about 12-15 hours, for at least about 1 day, for at least about 2 days, for at least about 3 days to produce mDC. In some embodiments the imDC may be cultured in the presence of the maturation cocktail for about 24 hours to produce mDC. In other embodiments the imDC may be cultured in the presence of the maturation cocktail for about 48 hours to produce mDC.

mDC may express one or more markers such as CD83, CD86, MHC I and MHC II, but not CD14 and may have functional properties similar to mature DC that are differentiated in vivo. Functional properties may include the capability to process and present antigen to an immunologically competent cell. Processing and presenting antigen may include for example the proteolysis of a target protein, as well as the expression and processing of a nucleic acid encoding a target antigen. The mDC may also have the ability to migrate within peripheral and lymphoid tissue. Thus mDC differentiated from pPS cells according to the invention may be induced to migrate in response to an appropriate stimulus such as MIP3β. The mDC may secrete one or more cytokines such as one or more pro-inflammatory cytokines. Exemplary cytokines secreted by DC according to the invention may include IL-12, IL-10 and IL-6.

Various embodiments of the invention described herein provide methods of differentiating pPS cells into DC. It is contemplated that the methods may further comprise mitotically inactivating various types of cells including unwanted pPS cells in a differentiated population as well as cells made according the methods described infra (e.g. any hematopoietic lineage cells, including mDC and imDC). Thus some embodiments of the invention may comprise contacting the DC cells with a protein or peptide antigen or a nucleic acid encoding an antigen and contacting the DC e.g. an mDC, with a radiation source or a chemical agent suitable for inhibiting cell division. Exposure of the mDC to a radiation source or the chemical agent may be desirable where the mDC are contained in a population of cells comprising at least one pPS cell. Irradiating the cells or treating the cells with the chemical agent will inhibit cell division, while maintaining functionality of the mDC. Moreover, treating the cells with a radiation source or a chemical agent may minimize any undesirable effects stemming from the presence of pPS cells in the population.

In some embodiment the invention provides a method of differentiating pPS cells into mesoderm comprising contacting the pPS cells with a differentiation cocktail comprising a plurality of exogenous cytokines such as BMP-4, VEGF, SCF and optionally GM-CSF and culturing the cells for at least a day thereby differentiating pPS cells into mesoderm. In some embodiments the cells may be cultured for at least about 2 days, at least about 3 days, at least about 4 days, at least about 5 days with the differentiation cocktail thereby differentiating the pPS cells into mesoderm. In certain embodiments the pPS cells may be cultured with a differentiation cocktail for about 5 days in order to differentiate the pPS cells into mesoderm. In some embodiments the differentiation cocktail may optionally further comprise one or more of the following: FLT3L, TPO, IL-4 and IL-3. The mesoderm cells may express one or more factors or markers expressed by mesoderm cells. For example increased expression of the mesoderm associated transcription factor, Brachyury, along with the decreased expression of pPS associated transcription factor Oct4 and Tra-160 may be indicative of the differentiation of pPS cells to mesoderm cells. Allowing the culture to continue to grow in the presence of the differentiation cocktail may facilitate further differentiation of the mesoderm cells, e.g. into cells of hematopoietic lineage. Thus in some embodiments the cell culture may be grown in the presence of the differentiation cocktail for a suitable length of time to differentiate the cells beyond mesoderm cells and into other hematopoietic lineage cells. For example the cells may be grown at least about 6 days, at least about 7 days, at least about 8 days, at least about 9 days, at least about 10 days with the differentiation cocktail described herein thereby differentiating the pPS cells into hematopoietic stem cells. The cells may express one or more markers expressed by hematopoietic stem cells. Suitable markers may include CD45, CD34, and HoxB4. In yet further embodiments the cells may be grown at least about 22 days, at least about 23 days, at least about 24 days, at least about 25 days, at least about 26 days, at least about 27 days, at least about 28 days with the differentiation cocktail described herein thereby differentiating the pPS cells into monocytes. The cells may express one or more markers expressed by monocytes. Suitable markers may include CD14, CD45 and CD11c. In still further embodiments the cells may be grown at least about 20 days, at least about 23, at least about 25 days, at least about 30 days, at least about 31 days, at least about 32 days, at least about 33 days, with the differentiation cocktail described herein thereby differentiating the pPS cells into imDC. The cells may express one or more markers expressed by imDC. Suitable markers may include CD86, CD83, and MHC II.

In certain embodiments the invention provides a method of differentiating pPS cells in hematopoietic lineage cells comprising contacting the pPS cells with one or more differentiation cocktails such that the pPS cells differentiate into one or more hematopoietic lineage cell types. The method may be comprised of multiple steps wherein one or more of the steps results in the differentiation of intermediate cell types of hematopoietic lineage. The invention contemplates not only the execution of all of the steps set forth below, but also the execution of one or more individual steps in order to attain a desired intermediate or precursor cell type of hematopoietic lineage.

In some embodiments the invention provides a method of differentiating pPS cells into mesoderm comprising 1) contacting the pPS cells with a first differentiation cocktail comprising BMP-4, VEGF, SCF and optionally GM-CSF thereby differentiating pPS cells into mesoderm cells. The cells may be cultured with this differentiation cocktail for about 1-5 days. In further embodiments the mesoderm cells from step 1) may then be contacted with a second differentiation cocktail comprising VEGF, SCF, GM-CSF thereby differentiating the mesoderm cells into hematopoietic stem cells. The cells may be cultured with this differentiation cocktail for about 1-5 days. In further embodiments hematopoietic the stem cell may be further differentiated into a common myeloid progenitor (CMP) cell by contacting the hematopoietic stem cell with a differentiation cocktail comprising GM-CSF. For this step the differentiation cocktail may further comprise SCF. The cells may be cultured with this differentiation cocktail for about 1-10 days. In some embodiments the CMP may be further differentiated into a common granulocytic/monocytic progenitor (GMP) cell by contacting the CMP with a third differentiation cocktail comprising GM-CSF. The cells may be cultured with this differentiation cocktail for about 1-5 days. In further embodiments the GMP may be further differentiated into monocytes by contacting the GMP with a differentiation cocktail comprising GM-CSF. The cells may be cultured with this differentiation cocktail for about 1-10 days. In still further embodiments the monocytes may be further differentiated into imDC by contacting the monocytes with a differentiation cocktail comprising GM-CSF and IL-4. The cells may be cultured with this differentiation cocktail for about 1-5 days. In yet further embodiments the imDC may be matured into mDC by contacting the imDC with any of the maturation cocktails described infra. The cells may be cultured with the maturation cocktail from about 12-72 hours. In some embodiments the cells may be cultured with the maturation cocktail for about 24 hours. In other embodiments the cells may be cultured with the maturation cocktail for about 48 hours.

In still other embodiments the invention provides a method of differentiating pPS cells into imDC comprising contacting the pPS cells with a differentiation cocktail comprising the following: 1) BMP-4 ranging from about 10 ng/ml to about 75 ng/ml; and 2) GM-CSF ranging from about 25 ng/ml to about 75 ng/ml.

In still other embodiments the invention provides a method of differentiating pPS cells into imDC comprising contacting the pPS cells with a differentiation cocktail comprising the following: 1) BMP-4 ranging from about 10 ng/ml to about 75 ng/ml; 2) VEGF ranging from about 25 ng/ml to about 75 ng/ml; 3) SCF ranging from about 5 ng/ml to about 50 ng/ml; and 4) GM-CSF ranging from about 25 ng/ml to about 75 ng/ml.

In a further embodiment the invention provides a method of enriching a myeloid progenitor cell population comprising isolating a CD45+ Hi population from a cell culture comprising a CD45+ Hi cell population and a CD45+ low cell population. In a further embodiment the invention provides a method of isolating a granulocyte progenitor cell comprising isolating a CD45+ low population from a cell culture comprising a CD45+ Hi cell population and a CD45+ low cell population. High and low are relative terms. Thus a CD45+ low cell population may refer to a cells having CD45 expression about 1-2 orders of magnitude above background, while the CD45+ Hi cells may refer to cells having CD45 expression greater than 2 orders of magnitude above background as measured using any assay know in the art, e.g. immunofluorescence as measured using a fluorescence detector, e.g. Fluorescent Activated Cell Sorter (FACS). Isolating the target cell population may be done using any means known in the art. For example, the cell populations may be isolated using a commercially available (FACS). In some embodiments the cells may be isolated based on fluorescent intensity of a marker stained with a labeled ligand. The labeled ligand may attach directly to the cell or indirectly to the cell by virtue of another ligand attached to the cell by the human hand. The cell populations may be isolated based on size and density based on forward and side scatter on a cell sorter. As an example CD45+ Hi and CD45+ low populations may be separated using a cell sorter based on size and granularity.

The cytokine combinations useful in carrying out various embodiments of the invention may be, used at any suitable final working concentration to achieve the desired effect. For example, BMP-4 may be used at a concentration ranging from about 1 ng/ml to about 120 ng/ml; from about 5 ng/ml to about 100 ng/ml; from about 10 ng/ml to about 80 ng/ml; from about 25 ng/ml to about 75 ng/ml; from about 30 ng/ml to about 60 ng/ml. In some embodiments of the invention about 50 ng/ml of BMP-4 may be used. VEGF may be used at a concentration ranging from about 1 ng/ml to about 120 ng/ml; from about 5 ng/ml to about 100 ng/ml; from about 20 ng/ml to about 80 ng/ml; from about 25 ng/ml to about 75 ng/ml; from about 30 ng/ml to about 60 ng/ml. In some embodiments of the invention about 50 ng/ml of VEGF may be used. GM-CSF may be used at a concentration ranging from about 1 ng/ml to about 120 ng/ml; from about 5 ng/ml to about 100 ng/ml; from about 20 ng/ml to about 80 ng/ml; from about 25 ng/ml to about 75 ng/ml; from about 30 ng/ml to about 60 ng/ml. In some embodiments of the invention about 50 ng/ml of GM-CSF may be used. SCF may be used at a concentration ranging from about 1 ng/ml to about 350 ng/ml; from about 5 ng/ml to about 300 ng/ml; from about 10 ng/ml to about 250 ng/ml; from about 15 ng/ml to about 200 ng/ml; from about 20 ng/ml to about 150 ng/ml; from about 5 ng/ml to about 50 ng/ml. In some embodiments of the invention about 20 ng/ml of SCF may be used. FLT3L may be used at a concentration ranging from about 1 ng/ml to about 350 ng/ml; from about 5 ng/ml to about 300 ng/ml; from about 10 ng/ml to about 250 ng/ml; from about 15 ng/ml to about 200 ng/ml; from about 20 ng/ml to about 150 ng/ml. In some embodiments of the invention about 20 ng/ml of FLT3L may be used. IL-3 may be used at a concentration ranging from about 1 ng/ml to about 80 ng/ml; from about 5 ng/ml to about 75 ng/ml; from about 10 ng/ml to about 50 ng/ml; from about 20 ng/ml to about 40 ng/ml. In some embodiments of the invention about 25 ng/ml of IL-3 may be used. TPO may be used at concentration ranging from about 1 ng/ml to about 150 ng/ml; from about 5 ng/ml to about 100 ng/ml; from about 10 ng/ml to about 80 ng/ml; from about 20 ng/ml to about 60 ng/ml. In some embodiments of the invention about 20 ng/ml of TPO may be used. IL-4 may be used at a concentration ranging from about 1 ng/ml to about 120 ng/ml; from about 5 ng/ml to about 100 ng/ml; from about 20 ng/ml to about 80 ng/ml; from about 25 ng/ml to about 75 ng/ml; from about 30 ng/ml to about 60 ng/ml. In some embodiments of the invention about 50 ng/ml of IL-4 may be used.

In some embodiments of the invention a maturation cocktail comprising a plurality of cytokines may be used to mature imDC to mDC. Suitable final working concentrations of cytokine components of the maturation cocktail may include any concentration which effectively matures imDC to mDC. For example IFNγ may be used at a concentration ranging from about 1 ng/ml to about 150 ng/ml; from about 5 ng/ml to about 100 ng/ml; from about 10 ng/ml to about 100 ng/ml; from about 15 ng/ml to about 80 ng/ml; from about 20 ng/ml to about 60 ng/ml. In some embodiments of the invention about 25 ng/ml of IFNγ may be used. In other embodiments of the invention about 10 ng/ml of IFNγ may be used. In other embodiments of the invention about 5 ng/ml of IFNγ may be used. TNFα may be used at a concentration ranging from about 1 ng/ml to about 200 ng/ml; from about 10 ng/ml to about 150 ng/ml; from about 20 ng/ml to about 100 ng/ml; from about 30 ng/ml to about 80 ng/ml; from about 40 ng/ml to about 75 ng/ml. In some embodiments of the invention about 10 ng/ml of TNFα may be used. IL-1β may be used at concentration ranging from about 1 ng/ml to about 200 ng/ml, from about 5 ng/ml to about 150 ng/ml; from about 8 ng/ml to about 75 ng/ml; from about 10 ng/ml to about 50 ng/m. In some embodiments of the invention about 10 ng/ml of IL-1β may be used. PGE2 may be used at a concentration ranging from about 0.1 ug/ml to about 150 ug/ml; from about 0.5 ug/ml to about 100 ug/ml; from about 0.8 ug/ml to about 75 ug/ml; from about 1 ug/ml to about 50 ug/ml. In some embodiments of the invention about 1 ug/ml of PGE2 may be used. Poly I:C may be used a concentration ranging from about 1 ug/ml to about 50 ug/ml, from about 5 ug/ml to about 40 ug/ml from about 10 ug/ml to about 30 ug/ml, form about 15 ug/ml to about 25 ug/ml. In some embodiments of the invention about 20 ug/ml of Poly I:C may be used.

In certain embodiments the invention provides for the differentiation of pPS cells in hematopoietic lineage cells wherein at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% of cells express one or more markers or factors that are expressed by cells of hematopoietic lineage.

Cell Cultures Comprising Primate Pluripotent Stem Cells and Their Differentiated Progeny In certain embodiments the invention provides a cell culture comprising a first population of cells comprising pPS cells and a second population of cells comprising hematopoietic lineage cells and/or mesoderm cells. The hematopoietic lineage cells and/or mesoderm cells may arise in the culture as a result of specific growth conditions which favor the differentiation of pPS cells into a target cell type, e.g. mesoderm cells, myeloid precursor cells, monocytes, dendritic cells and the like. The growth conditions may include providing one or more differentiation cocktails (as described infra) and in some embodiments a maturation cocktail (as described infra). The cell culture may be free of one or more of the following: feeder cells, stromal cells, animal serum and/or commercially available serum replacements such as B27, and exogenous IL-3.

In some embodiments the second population of cells may comprise mesoderm cells. In the developing embryo mesoderm is positioned between the ectoderm and endoderm. Connective tissue, bone, cartilage, muscle, hematopoietic lineage cells, blood and blood vessels, lymphatics, lymphoid organs, notochord, pleura, pericardium, peritoneum, kidneys and gonads all originate from the mesoderm. Mesoderm cells may express various markers including expression of the transcription factor brachyury. Expression levels of brachyury may increase about three to six fold when compared to pPS cells prior to differentiation to mesoderm cells. Other markers for mesoderm may include goosecoid. Goosecoid a member of the bicoid subfamily of the paired (PRD) homeobox family of proteins. The encoded protein acts as a transcription factor and may be autoregulatory.

In other embodiments the hematopoietic lineage cells may comprise hemangioblast cells. Hemangioblast cells have the ability to differentiate further into lymphoid cells of various types, myeloid cells of various types, as well as endothelial cells. Hemangioblasts may express CD34 and CD133. Loges et al., (2004). *Stem Cells and Development* 13 (1): 229. Other markers for hemangioblasts include Flk-1 which is a kinase insert domain receptor.

In yet other embodiments the hematopoietic lineage cells may comprise hematopoietic stem cells. Hematopoietic stem cells may be able to differentiate into any cell type found in the blood, including lymphoid cells, (whose progeny includes T cells and B lymphocytes) and myeloid cells (whose progeny includes granulocytes of various types, monocytes, macrophages, DC, megakaryocytes, platelets, erythroblasts, and erythrocytes). Markers for hematopoietic stem cells may include CD34+, CD59+, Thy1/CD90+, $CD38^{lo/-}$, C-kit/$CD117^{-/lo}$. In certain embodiments of the invention the percentage of cells expressing at least one marker associated with hematopoietic stem cells ranges from about 1% to about 20%, from about 5% to about 17%, from about 10% to about 15%. In some embodiments of the invention about 15% of the cells in the cell culture express at least one marker associated with hematopoietic stem cells.

In further embodiments the hematopoietic lineage cells may comprise common myeloid progenitor cells. Myeloid progenitor cells may, under appropriate growth conditions, differentiate into various myeloid cells including granulocytes, monocytes, macrophages, DC, megakaryocyte/erythrocyte progenitor cells. Markers for myeloid progenitor cells may include CD13, CD34, IL-3Rα (CD123), and CD45RA. In certain embodiments of the invention the percentage of cells expressing at least one marker associated with myeloid progenitor cells ranges from about 1% to about 50%, from about 5% to about 45%, from about 6% to about 38%. In some embodiments of the invention about 35% of the cells in the cell culture express at least one marker associated with myeloid progenitor cells.

In still other embodiments the hematopoietic lineage cells may comprise granulomonocytic progenitor cells. Granulomonocytic progenitor cells may, under appropriate conditions differentiate into granulocytes, monocytes, macrophages and DC. Markers for granulomonocytic progenitor cells may include CD64 (EP0708336).

In further embodiments the hematopoietic lineage cells may comprise monocytes. Under appropriate growth conditions monocytes may differentiate into DC, macrophages and granulocytes cells. Markers for monocytes may include CD14, $CD45^{hi}$, CD11a, CD11b, and CD15. The monocyte morphology may include the presence of a large bi-lobed nucleus. In certain embodiments of the invention the percentage of cells expressing at least one marker associated with monocytes ranges from about 1% to about 75%, from about 5% to about 70%, from about 10% to about 65%. In some embodiments of the invention about 65% of the cells in the cell culture express at least one marker associated with monocytes.

In still further embodiments the hematopoietic lineage cells may comprise imDC. imDC have the ability to take up and process antigen. Under appropriate growth conditions imDC may undergo maturation to become mDC suitable for presenting antigens to an immunologically competent cell. Markers for imDC may include $CD11c^{hi}$, CD11b, MHC I, MHC $II^{lo}$, $CD14^{-/lo}$, $CD205^-$, and $CD83^{lo}$. In certain embodiments of the invention the percentage of cells expressing at least one marker associated with imDC ranges from about 10% to about 99%, from about 20% to about 99%. In certain embodiments of the invention at least about 90%, about 80% about 70%, about 60%, about 50% about 40% about 30%, about 20% about 10% of the cells in the cell culture express at least one marker associated with imDC.

In yet other embodiments the hematopoietic lineage cells may comprise mDC. mDC may have the ability to migrate in response to an appropriate stimuli e.g, MIP3β and to present antigen to an immunologically competent cell such as a T lymphocyte. mDC may have a distinctive morphology that include the presence of branched projections or dendrites which emanate out from the cell. Markers for mDC may include CD83, CCR7, $CD11c^{hi}$, CD205, CD86, CD40, MHC I, MFIC II and $CD14^-$. In certain embodiments of the invention the percentage of cells expressing at least one marker associated with mDC ranges from about 10% to about 99%, from about 20% to about 99%. In certain embodiments of the invention at least about 90%, about 80%, about 70%, about 60%, about 50%, about 40%, about 30%, about 20%, about 10%, of the cells in the cell culture express at least one marker associated with mDC.

Tissue-specific markers may be detected using suitable immunological techniques—such as flow immunocytometry or affinity adsorption for cell-surface markers, immunocytochemistry (for example, of fixed cells or tissue sections) for intracellular or cell-surface markers, Western blot analysis of cellular extracts, and enzyme-linked immunoassay, for cellular extracts or products secreted into the medium. Expression of an antigen by a cell is said to be antibody-detectable if a significantly detectable amount of antibody will bind to the antigen in a standard immunocytochemistry or flow cytometry assay, optionally after fixation of the cells, and optionally using a labeled secondary antibody.

The expression of tissue-specific gene products may also be detected at the mRNA level by Northern blot analysis, dot-blot hybridization analysis, or by reverse transcriptase initiated polymerase chain reaction (RT-PCR) using sequence-specific primers in standard amplification methods using publicly available sequence data (GenBank). Expression of tissue-specific markers as detected at the protein or mRNA level is considered positive if the level is at least about 2-fold, more than about 10- or about 50-fold above that of an undifferentiated primate pluripotent stem cell.

The expression of tissue-specific gene products may also be detected at the mRNA level by Northern blot analysis, dot-blot hybridization analysis, or by reverse transcriptase initiated polymerase chain reaction (RT-PCR) using sequence-specific primers in standard amplification methods. See U.S. Pat. No. 5,843,780 for further details. Sequence data for the particular markers listed in this disclosure can be obtained from public databases such as GenBank. Expression at the mRNA level is said to be "detectable" according to one of the assays described in this disclosure if the performance of the assay on cell samples according to standard procedures in a typical controlled experiment results in clearly discernable hybridization or amplification product. Expression of tissue-specific markers as detected at the protein or mRNA level is considered positive if the level is at least about 2-fold, more than about 10- or about 50-fold above that of an undifferentiated primate pluripotent stem cell.

Once markers have been identified on the surface of cells of the desired phenotype, they can be used for immunoselection to further enrich the population by techniques such as immunopanning or antibody-mediated FACS.

Irradiation of DC Differentiated from pPS Cells

The invention contemplates methods of irradiating populations of cells comprising mDC or imDC differentiated in vitro from pPS cells, i.e. are the in vitro progeny of pPS cells, as well as irradiated cell cultures comprising mDC or imDC differentiated in vitro from pPS cells. Other embodiments of the invention contemplate irradiated immunomodulatory preparations and methods of making the same as well as methods of stimulating an immune response using an irradiated cell population comprising mDC. Still other embodiments of the invention contemplate kits comprising irradiated mDC.

Irradiating mDC differentiated from pPS cells inhibits any further cell division thereby diminishing any risk, such as teratomas formation, posed by cells (e.g. pPS cells) which have not fully differentiated into mDC. The irradiated mDC may maintain functional properties associated with non-irradiated DC such as PBMC derived DC, and thus irradiated mDC may be capable of processing and presenting antigen to an immunologically competent cell and causing that cell to respond to the presented antigen. The irradiated mDC may also maintain the ability to migrate in response to chemotactic stimuli. Furthermore, the irradiated mDC may also continue to express markers typically found on mDC, e.g., PBMC derived mDC. These markers may include HLA-II, HLA-I, and CD83. It is further contemplated that mDC according to the invention may be contacted with an antigen or a nucleic acid encoding an antigen prior to exposure to a radiation source.

In some embodiments an mDC may be contacted with antigen, e.g. a protein or a peptide and then irradiated. In other embodiments an mDC may be contacted, e.g. electroporated or contacted using any other suitable transfection means, with a nucleic acid such as an RNA molecule and then irradiated. In some embodiments the cells may be contacted with the nucleic acid and then permitted to rest for about 24 hours (e.g. at 37° C. and 5% $CO_2$). The cells may then be placed in a suitable cryo media (e.g. one comprising DMSO) and then frozen at about −80° C. The frozen cells may then be irradiated (e.g. on dry ice) and then stored frozen (e.g. in liquid nitrogen) until further use is required.

Any suitable source of radiation may be used to irradiate mDC according to the invention. In one embodiment the radiation source may be an ionizing radiation source. As an example an X-ray may provide a suitable source of radiation. Other types of radiation which may be suitable include UV irradiation e.g. gamma irradiation.

The cell population comprising mDC differentiated in vitro from pPS cells may be irradiated for a suitable length of time e.g. such that cell division is inhibited. Parameters such as radiation dosage, cell population size and time of exposure may be optimized empirically and then tested by culturing cells post radiation and determining whether or not the cells continue to divide. Determination of cell division may be accomplished by counting cells manually using a hemacytometer. Alternatively an automated cell counter may be used.

When the radiation source is an X-ray a suitable radiation dose may range from about 300 rad to about 3500 rad; from about 400 rad to about 3000 rad; from about 500 rad to about 2500 rad; from about 500 rad to about 2000 rad; from about 400 rad to about 1500 rad. In one embodiment about 2000 rad are applied to a population of cells comprising mDC. In another embodiment about 1500 rad are applied to a population of cells comprising mDC. In a further embodiment about 1000 rad are applied to a population of cells comprising mDC. In still another embodiment about 500 rad are applied to a population of cells comprising mDC.

Where the radiation source is UV irradiation a suitable dose may range from about 10 $J/m^2$ to about 3,000 $J/m^2$; from about 20 $J/m^2$ to about 2,000 $J/m^2$; from about 25 $J/m^2$ to about 1,500 $J/m^2$; from about 30 $J/m^2$ to about 500 $J/m^2$; from about 50 $J/m^2$ to about 200 $J/m^2$. In some embodiments about 50 $J/m^2$ may be used. In other embodiments about 100 $J/m^2$ may be used. In other embodiments about 200 $J/m^2$ may be used. In still other embodiments about 300 $J/m^2$ may be used. In yet other embodiments about 500 $J/m^2$ may be used.

Where the radiation source is an X-ray, the cells may be suspended in a suitable media or buffer prior to exposure to the radiation source. A suitable media would include any commercially available media for growing or differentiating stem cells. As an example AIM V media (Invitrogen, Carlsbad, Calif.) may be used. A suitable buffer may include any isotonic buffer, e.g. PBS. The volume of media used will depend on the size of the cell population to be irradiated. For a population of cells ranging from about $3.0 \times 10^5$ to about $4.0 \times 10^5$ a suitable volume may range from about 5-20 mls of media or buffer. In one embodiment about 15 mls of media or buffer may be used.

Where the radiation source is a UV light the cells may grown attached to a substrate such as a tissue culture flask and exposed to the radiation source. The cells may be maintained in a suitable buffer or media during exposure to the radiation.

In one embodiment a population of cells ranging from about $3.0 \times 10^5$ cells to about $4.0 \times 10^5$ cells is irradiated with about 2000 rad from an X-ray source. In another embodiment a population of cells ranging from about $3.0 \times 10^5$ cells to about $4.0 \times 10^5$ cells is irradiated with about 1500 rad from an X-ray source. In yet another embodiment a population of cells ranging from about $3.0 \times 10^5$ cells to about $4.0 \times 5$ cells is irradiated with about 1000 rad from an X-ray source. In still another embodiment a population of cells ranging from about $3.0 \times 10^5$ cells to about $4.0 \times 10^5$ cells is irradiated with about 500 rad from an X-ray source. The cells may be comprised of mDC differentiated in vitro from pPS cells.

It is also contemplated that a chemical agent suitable for inhibiting cell division may be substituted for the radiation source. Thus cell populations comprising mDC differentiated in vitro from pPS cells may be contacted with a chemical agent suitable for inhibiting cell division. Examples of suitable chemicals include chemotherapeutics such as mitomycin C and cisplatin. Other suitable chemicals may include one or more of the following: arabinoside, fluoro-deoxyuridine and uridine.

Systems for Producing Dendritic Cells

In certain embodiments the invention contemplates a system for the in vitro production of mature dendritic cells comprising a) a first isolated cell population comprising pPS cells and b) a second isolated cell population comprising mature dendritic cells which are the in vitro progeny of a portion of the first population of cells.

In other embodiments the invention contemplates a system for the production of mitotically inactive antigen presenting cells comprising a) a first isolated cell population comprising pPS cells and b) a second isolated cell population comprising mitotically inactivated mature dendritic cells which are the in vitro progeny of a portion of the first isolated cell population.

The mDC may be differentiated in vitro from a portion of the pPS cells and a portion of the first isolated cell population comprising the pPS cells can be held in reserve, used to make more of the second isolated population by differentiating the first population of cells in vitro. The system contemplates that the first population of cells comprising pPS cells may include a portion of the population that may be differentiated into DC using the methods described herein, and a portion of the population that may be reserved for future use e.g. maintained in culture in an undifferentiated state or frozen (in a suitable media) in aliquots and stored at −80° C. or in liquid nitrogen. Because the pPS cells are capable of replicating in culture in an undifferentiated (pluripotent) state indefinitely, the system provides a means of producing a limitless supply of differentiated DC according to the methods described herein. Moreover, because the DC, e.g. imDC differentiated in vitro from the pPS cells may also replicate in culture the system provides a second population which is capable of producing additional DC. The system thus provides a means of continually producing large quantities of a uniform product such as a DC. The system may also include embodiments in which one or both populations are mitotically inactivated as described infra.

Characteristic markers and morphology of both the first population of cells comprising pPS cells and the second population of cells comprising DC cells are described herein. The DC cells may be mDC loaded with an antigen of interest, e.g. a tumor antigen such as hTERT. The DC cells may be irradiated according to the invention in order to mitotically inactivate the cells and thus diminish any potential risk of pPS cells which may be present in the second population of cells comprising the DC. In certain embodiments at least about 5%, at least about 10%, at least about 20%, at least about 30%, at least about 40%, at least about 50%, at least about 60%, at least about 70%, at least about 80%, at least about 90%, at least about 95% of the mDC may express one or more markers chosen from CD83, CD86, MHC II and CCR7.

Kits

In certain embodiments the invention provides a kit for stimulating an immune response. In one embodiment the kit may comprise a cell culture comprising pPS cells and DC, and one or more containers. Optionally the kit may comprise one or more of the following: a) instructions for stimulating an immune response; b) instructions for culturing the DC; c) a maturation cocktail, where the provided DC are imDC; c) one or more suitable culture vessels; d) one more antigens for stimulating an immune response; e) one or more immunologically competent cells; and f) suitable reagents for measuring the stimulated immune response. The kit may be used to stimulate an immune response in vitro or in vivo. The DC may be imDC or mDC. In some embodiments the DC may be provided frozen. The cells may be frozen in liquid nitrogen and stored at about −140° C. Alternatively, the DC may be packaged and stored under refrigeration, e.g. at about 4° C. The maturation cocktail may be supplied premixed or with each of its components packaged separately. The antigen may be provided as a protein or peptide or as nucleic acid, e.g., DNA, RNA encoding the antigen. The kit may also provide instructions for loading the DC with the antigen. Loading refers to contacting the DC with the antigen such that it is presented to an immunologically competent cell. The kit may further comprise instructions for growing the DC in culture, for contacting the DC with antigen, for contacting the DC with immunologically competent cells. Suitable reagents for detecting a stimulated immune response may include $^3$H thymidine for measuring cell proliferation, antibodies to cytokines secreted during an immune response to an antigen such as IL-2, IFN.

In another embodiment the kit may comprise an irradiated mDC differentiated in vitro from a pPS cell and one or more containers. Optionally the kit may comprise one or more of the following: a) instructions for stimulating an immune response; b) one more preloaded antigens for stimulating an immune response; c) one or more immunologically competent cells; and d) suitable reagents for measuring the stimulated immune response. The kit may be used to stimulate an immune response in vitro or in vivo. The preloaded antigen may be provided as a protein or peptide or as nucleic acid, e.g., DNA, RNA encoding the antigen. Loading refers to contacting the DC with the antigen such that it is presented to an immunologically competent cell. Suitable reagents for detecting a stimulated immune response may include $^3$H thymidine for measuring cell proliferation, antibodies to cytokines secreted during an immune response to an antigen such as IL-2, IFN. In other embodiments the invention provides a kit, as described above where chemically treated mDC may be substituted for the irradiated mDC. The chemically treated mDC may be mDC that have been contacted with a chemical agent suitable for inhibiting cell division. Suitable chemical agents may include mitomycins such as mitomycin C.

Uses of ES-Differentiated Hematopoietic-Lineage Cells

This invention provides a method to produce large numbers of cells of the hematopoietic and/or mesoderm lineage. These cell populations can be used for a number of important research, development, and commercial purposes.

Screening

The cells of this invention can be used commercially to screen for factors (such as solvents, small molecule drugs, peptides, oligonucleotides) or environmental conditions (such as culture conditions or manipulation) that affect the characteristics of such cells and their various progeny. Characteristics may include phenotypic or functional traits of the cells.

In some applications, pPS cells (undifferentiated or differentiated) are used to screen factors that promote maturation into later-stage hematopoietic precursors, or terminally differentiated cells, or to promote proliferation and maintenance of such cells in long-term culture. For example, candidate maturation factors or growth factors are tested by adding them to cells in different wells, and then determining any phenotypic change that results, according to desirable criteria for further culture and use of the cells.

Other screening applications of this invention relate to the testing of pharmaceutical compounds for their effect on hematopoietic lineage cells and/or mesoderm cells. Screening may be done either because the compound is designed to have a pharmacological effect on the cells, or because a compound designed to have effects elsewhere may have unintended side effects on cells of this tissue type. Other screening applications could include screening compounds for carcinogenic or other toxic effects. The screening can be conducted using any of the precursor cells or terminally differentiated cells of the invention in order to determine if the target compound has a beneficial or harmful effect on the target cell.

The reader is referred generally to the standard textbook *In vitro Methods in Pharmaceutical Research*, Academic Press, 1997. Assessment of the activity of candidate pharmaceutical compounds generally involves combining the cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in *In vitro Methods in Pharmaceutical Research*, Academic Press, 1997) for further elaboration.

Where an effect is observed, the concentration of the compound can be titrated to determine the median effective dose ($ED_{50}$).

Modulation of an Immune Response

In certain embodiments the invention provides a method of stimulating an immune response to an antigen comprising contacting a cell according to the invention, e.g., a DC differentiated from pPS cells, with an antigen. The antigen may be comprised of a protein or peptide or alternatively it may be comprised of a nucleic acid e.g. DNA, RNA. Where the antigen is a protein or peptide the dendritic cell will take up the protein or peptide and process it for presentation in the context of the MHC. Typically processing includes proteolysis so that the antigen will fit in the MHC groove. Where the antigen is a protein the DC cell may be an imDC. Where the antigen is a peptide fragment of a full length protein the DC may be a mDC. Where the antigen is a nucleic acid the invention contemplates using any means known in the art for transporting the nucleic acid across the cell membrane for delivery into the cytoplasm. In one embodiment the cells may be electroporated to allow the nucleic acid to cross the cell membrane. In some embodiments where electroporation is used to contact the cell with an antigen a suitable cell may be an imDC. In other embodiments where electroporation is used to contact the cell with an antigen a suitable cell may be an mDC. The cells may be electroporated using Gene Pulse Xcell (Bio-Rad Laboratories, Hercules, Calif.) with the following parameters: 300V, 150 uF, and 100 Ohms. Protein expression levels may be determined by flow cytometry or western blot methods. Where the electroporated cell is an imDC the cells may be contacted with a maturation cocktail as described herein such that the imDC mature into mDC.

In another embodiment a viral vector may be used to transport the nucleic acid encoding the antigen into the cell, e.g., a mDC, an imDC. Where a viral vector is used to contact the cell with an antigen a suitable cell may be imDC. Examples of suitable viral vectors include adenoviral vectors and pox viral vectors. In other embodiments commercially available transfection reagents may be used to transport the nucleic acid encoding the antigen into the cell. Suitable examples include cationic lipid formulations such as Lipofectamine®.

The invention contemplates using antigens from any source. Thus the antigen may be a tumor antigen such as human teleomerase reverse transcriptase (hTERT) or an antigen expressed by infectious agent such as a virus, a bacterium, or a parasite.

The mDC may then be contacted, either in vivo or in vitro, with an immunologically competent cell such as a lymphocyte. The immune response of the lymphocyte may be monitored by measuring cell proliferation of the immunologically competent cell (e.g., by $^3$H thymidine incorporation) and/or cytokine production (e.g. IL-2, IFN, IL-6, IL-12) by either the mDC or the immunologically competent cell. These studies may be useful in tailoring the type and extent of the immune response to the antigen. These studies may also be useful in selecting the best epitope of the antigen for eliciting the most appropriate immune response. The immune response may be stimulated in vitro or in vivo using an appropriate animal model.

To determine the suitability of cell compositions for therapeutic administration, the cells can first be tested in a suitable animal model. Suitable animal models may include a mouse with a humanized immune system. See, e.g., Goldstein (2008) *AIDS Res Ther* 5(1):3. mDC primed with a specific antigen may be administered to an animal to determine whether or not the animal is able to mount a specific immune response to the antigen. The animal and the DC may be matched or partially matched at the MHC I locus. Dosing, administration and formulation of the antigen and of the cells may be studied to tailor the immune response to the antigen and migration of the administered cells within the lymphatic system may be monitored. The extent of the immune response may be characterized in terms of cytokine production as well as lymphocyte proliferation in response to the antigen. The animal may be monitored for an antibody response against the antigen as well as for any atypical immune reaction, e.g. hypersensitivity, autoimmune reaction. The antibody generated may be isolated for use as a research reagent or therapeutic agent.

imDC are known to induce antigen specific tolerance, see, e.g., Cools et al., (2007) *J Leukoc Biol* 82(6):1365. Thus imDC, as described herein, may be used to induce tolerance within a subject. The imDC cells may be contacted with antigen, e.g., a protein or peptide antigen or a nucleic acid encoding an antigen as described above. The cells may then be administered to a subject to induce tolerance in the subject. Alternatively, the imDC may be matured into mDC and used to stimulate an immune response.

Reconstitution of Hematopoietic Cells

Hematopoietic lineage cells made according to the invention may be used to reconstitute one or more hematopoietic cells populations in a subject. As an example myeloid progenitor cells may be used to ameliorate one or more symptoms associated with cytopenia by reconstituting a cell population that is deficient. For example myeloid progenitors may be used improve the condition of a subject with low platelet count, or low erythrocyte count. As another example hematopoietic lineage cells, such as myeloid precursor cells may be used to improve one or more symptoms of a subject with a genetic defect, such as a defect relating to a clotting factor. Thus cells made according to some embodiments of the invention may be used increase the level of a clotting factor such as factor VIII or factor IX. In other embodiments the hematopoietic lineage cells may be used to reconstitute a lymphocyte population, e.g. a CD4 lymphocyte population in a patient with HIV.

Administration to Humans

The mDC produced according to the invention are functionally comparable to mDC isolated from PBMCs. For example the mDC of the invention can take up process and present antigen; stimulate T cell proliferation in response to presentation of a specific antigen and can induce antigen specific T cell mediated cytolysis of target cells. Additionally, functionality of the mDC according to the invention is maintained even after irradiation. The mDC of the invention may thus provide a source of DC for administration to a human subject in order to stimulate an immune response to a specific antigen while minimizing the risk of exposure to undifferentiated cells and pathogenic agents.

mDC according to this invention may be administered to a human subject to stimulate an immune response in the subject. Prior to administration, the imDC may be contacted with an antigen of interest and then matured into mDC. The antigen may be internalized and processed such that it is presented on the cell surface in the context of MHC I and/or MHC II and thus may stimulate a specific immune response to the antigen. In some embodiments the specific immune response may have a therapeutic effect. In other embodiments the immune response may provide a prophylactic effect. In still other embodiments the specific immune response may provide a source of antigen specific cells such as cytotoxic T cells, or B lymphocytes or antibodies which specifically recognize the antigen. Administration of the cells according to the invention may be by intravenous, intradermal or intramuscular injection. In other embodiments the cells may be administered subcutaneously. The cells may be formulated with an appropriate buffer, such as PBS and/or an appropriate excipient. The cells may be formulated with a suitable adjuvant. Examples of suitable pharmaceutical carriers are described in *Remington's Pharmaceutical Sciences* by E. W. Martin 20th Edition. Baltimore, Md.: Lippincott Williams & Wilkins, 2000.

For general principles in medicinal formulation, the reader is referred to *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000. Choice of the cellular excipient and any accompanying elements of the composition will be adapted in accordance with the route and device used for administration.

Pharmaceutical compositions of this invention may optionally be packaged in a suitable container with written instructions for a desired purpose, such as the reconstitution of hematopoietic-lineage cell function to improve a disease condition or to stimulate an immune response.

Other Uses

The cells of this invention may be used to prepare a cDNA library relatively uncontaminated with cDNA preferentially expressed in cells from other lineages. For example, hematopoietic-lineage cells are collected by centrifugation at 1000 rpm for 5 minutes, and then mRNA is prepared and reverse transcribed. Expression patterns of the hematopoietic-lineage cells may be compared with other cell types, e.g., pPS cells, by microarray analysis, reviewed generally by Fritz et al., (2000) *Science* 288:316. Because the cells are virtually genetically identical to the parental pPS cell line from which they differentiated they provide a particularly well suited system for studying genes involved in the differentiation and maturation of hematopoietic lineage cells. For example nucleic acid libraries from the parental cell line and the hematopoietic progeny may be prepared and subtractive hybridization may be employed to isolate genes important in differentiation and maturation of the progeny cells.

The differentiated cells of this invention can also be used to prepare antibodies that are specific for markers of hematopoietic-lineage cells. Polyclonal antibodies can be prepared by injecting a vertebrate animal with cells of this invention in an immunogenic form. Production of monoclonal antibodies is described in such standard references as Harlow & Lane (1988) *Antibodies: A Laboratory Manual*, U.S. Pat. Nos. 4,491,632, 4,472,500 and 4,444,887, and *Methods in Enzymology* 73B:3 (1981).

Primate Pluripotent Stem Cells

The present invention provides methods for differentiating pPS cells into hematopoietic-lineage cells. pPS cells include any primate pluripotent cell. A pluripotent cell will, under appropriate growth conditions, be able to form at least one cell type from each of the three primary germ layers: mesoderm, endoderm and ectoderm. The pPS cells may originate from pre-embryonic, embryonic or fetal tissue or mature differentiated cells. Alternatively, an established pPS cell line may be a suitable source of cells for practicing the invention. Typically, the pPS cells are not derived from a malignant source. pPS cells will form teratomas when implanted in an immuno-deficient mouse, e.g. a SCID mouse.

Under the microscope, primate pluripotent stem cells appear with high nuclear/cytoplasmic ratios, prominent nucleoli, and compact colony formation with poorly discernable cell junctions. Primate pluripotent stem cells typically express the stage-specific embryonic antigens (SSEA) 3 and 4, and markers detectable using antibodies designated Tra-1-60 and Tra-1-81. Undifferentiated human embryonic stem cells also typically express the transcription factor Oct-3/4, Cripto, gastrin-releasing peptide (GRP) receptor, podocalyxin-like protein (PODXL), nanog and telomerase reverse transcriptase, e.g., hTERT (US 2003/0224411 A1), as detected by RT-PCR.

pPS cells that may be used in any of the embodiments of the invention include, but are not limited to, embryonic stem cells such as human embryonic stem cells (hES). Embryonic stem cells can be isolated from blastocysts of a primate species (U.S. Pat. No. 5,843,780; Thomson et al., (1995) *Proc. Natl. Acad. Sci. USA* 92:7844). hES cells can be prepared from human blastocyst cells using, for example, the techniques described in U.S. Pat. No. 6,200,806; Thomson et al., (1998) *Science* 282:1145; Thomson et al. (1998) *Curr. Top. Dev. Biol.* 38:133 ff. and Reubinoff et al., (2000) *Nature Biotech.* 18:399.

Other primate pluripotent stem cell types include, but are not limited to, primitive ectoderm-like (EPL) cells, described in WO 01/51610 and human embryonic germ (hEG) cells (Shamblott et al., (1998) *Proc. Natl. Acad. Sci. USA* 95:13726).

pPS cells suitable for use in any of the embodiments of the invention also include induced primate pluripotent stem (iPS) cells. iPS cells refer to cells that are genetically modified, e.g., by transfection with one or more appropriate vectors, such that they attain the phenotype of a pPS cell. Phenotypic traits attained by these reprogrammed cells include morphology resembling stem cells isolated from a blastocyst, surface antigen expression, gene expression and telomerase activity that are all similar blastocyst derived cells. The iPS cells may have the ability to differentiate into at least one cell type from each of the primary germ layers: ectoderm, endoderm and mesoderm. The iPS cells may also form teratomas when injected into immuno-deficient mice, e.g., SCID mice. (Takahashi et al., (2007) *Cell* 131(5):861; Yu et al., (2007) *Science* 318:1917).

Embryonic stem cells used in the invention may be chosen from established embryonic stem cell lines or may be obtained directly from primary embryonic tissue. A large number of embryonic stem cell lines have been established including, but not limited to, H1, H7, H9, H13 or H14 (reference Thompson); hESBGN-01, hESBGN-02, hES-BGN-03 (BresaGen, Inc., Athens, Ga.); HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., (2005) *Fertil. Steril.* 83(5):1517); lines HUES 1-17 (Cowan et al., (2004) *NEJM* 350(13):1353); and line ACT-14 (Klimanskaya et al., (2005) *Lancet*, 365(9471):1636).

In certain embodiments, pPS cells used in the present invention may have been derived in a feeder-free manner (see, e.g., Klimanskaya et al., (2005) *Lancet*, 365(9471):

1636). In certain embodiments the pPS may be cultured prior to use in a serum free environment.

Culture Conditions for Primate Pluripotent Stem Cells pPS cells may be cultured using a variety of substrates, media, and other supplements and factors known in the art. In some embodiments a suitable substrate may include a matrix comprised of one or more of the following: laminin, collagen, fibronectin, vitronectin, heparin sulfate proteoglycan. In some embodiments the matrix may comprise a soluble extract of the basement membrane from a murine EHS sarcoma which is commercially available as Matrigel™ (BD Biosciences, San Jose, Calif.). In other embodiments the matrix may comprise one more isolated matrix proteins of human, humanized, or murine origin, e.g. CELLstart™ (Invitrogen, Carlsbad, Calif.). Primate pluripotent stem cells can be propagated continuously in culture, using culture conditions that promote proliferation while inhibiting differentiation. Exemplary medium may be made with 80% DMEM (such as Knock-Out DMEM, Gibco), 20% of either defined fetal bovine serum (FBS, Hyclone) or serum replacement (US 2002/0076747 A1, Life Technologies Inc.), 1% non-essential amino acids, 1 mM L-glutamine, and 0.1 mM β-mercaptoethanol. Other suitable media include serum free defined media such as X-VIVO™ 10 (Lonza, Walkersville, Md.).

In certain embodiments, pPS cells may be maintained in an undifferentiated state without added feeder cells (see, e.g., (2004) Rosier et al., *Dev. Dynam.* 229:259). Feeder-free cultures are typically supported by a nutrient medium containing factors that promote proliferation of the cells without differentiation (see, e.g., U.S. Pat. No. 6,800,480). In certain embodiments, conditioned media containing such factors may be used. Conditioned media may be obtained by culturing the media with cells secreting such factors. Suitable cells include irradiated (~4,000 rad) primary mouse embryonic fibroblasts, telomerized mouse fibroblasts, or fibroblast-like cells derived from primate pluripotent stem cells (U.S. Pat. No. 6,642,048). Medium can be conditioned by plating the feeders in a serum free medium such as KO DMEM supplemented with 20% serum replacement and 4 ng/mL bFGF. Medium that has been conditioned for 1-2 days is supplemented with further bFGF, and used to support pPS cell culture for 1-2 days (see e.g., WO 01/51616; Xu et al., (2001) *Nat. Biotechnol.* 19:971, 2001).

Alternatively, fresh or non-conditioned medium can be used, which has been supplemented with added factors (like a fibroblast growth factor or forskolin) that promote proliferation of the cells in an undifferentiated form. Exemplary is a base medium like X-VIVO™ 10 (Lonza, Walkersville, Md.) or QBSF™-60 (Quality Biological Inc. Gaithersburg, Md.), supplemented with bFGF at 40-80 ng/mL, and optionally containing SCF (15 ng/mL), or Flt3 ligand (75 ng/mL) (see, e.g., Xu et al., (2005) *Stem Cells* 23(3):315). These medium formulations have the advantage of supporting cell growth at 2-3 times the rate in other systems (see, e.g., WO 03/020920). In some embodiments pPS cells such as hES cells may be cultured in a media comprising bFGF and TGFβ. Suitable concentrations of bFGF include about 80 ng/ml. Suitable concentrations of TGFβ include about 0.5 ng/ml. Other commercially available media formulations may be used in certain embodiments of the invention. Suitable media formulations may include X-VIVO™ 15 (Lonza, Walkersville, Md.); mTeSR™ (Stem Cell Technologies, Vancouver, CA); hTeSR™ (Stem Cell Technologies, Vancouver, CA), StemPro™ (Invitrogen, Carlsbad, Calif.) and Cellgro™ DC (Mediatech, Inc., Manassas, Va.).

In some embodiments, the primate pluripotent stem cells may be plated at >15,000 cells $cm^{-2}$ (optimally 90,000 $cm^{-2}$ to 170,000 $cm^{-2}$). Typically, enzymatic digestion may be halted before cells become completely dispersed (e.g., about 5 minutes with collagenase IV). Clumps of ~10 to 2,000 cells may then be plated directly onto a suitable substrate without further dispersal. Alternatively, the cells may be harvested without enzymes before the plate reaches confluence by incubating the cells with for about 5 minutes in a solution of 0.5 mM EDTA in PBS or by simply detaching the desired cells from the plate mechanically, such as by scraping or isolation with a fine pipette. After washing from the culture vessel, the cells may be plated into a new culture without further dispersal. In a further illustration, confluent human embryonic stem cells cultured in the absence of feeders may be removed from the plates by incubating with a solution of 0.05% (wt/vol) trypsin (Gibco®, Carlsbad, Calif.) and 0.05 mM EDTA for 5-15 min at 37° C. The remaining cells in the plate may be removed and the cells may be triturated into a suspension comprising single cells and small clusters, and then plated at densities of 50,000-200,000 cells $cm^{-2}$ to promote survival and limit differentiation.

In certain embodiments, pPS cells may be cultured on a layer of feeder cells, typically fibroblasts derived from embryonic or fetal tissue (Thomson et al., (1998) *Science* 282:1145). In certain embodiments, those feeder cells may be derived from human or murine source. Human feeder cells can be isolated from various human tissues or derived by differentiation of human embryonic stem cells into fibroblast cells (see, e.g., WO01/51616) In certain embodiments, human feeder cells that may be used include, but are not limited to, placental fibroblasts (see, e.g., Genbacev et al., (2005) *Fertil. Steril.* 83(5):1517), fallopian tube epithelial cells (see, e.g., Richards et al., 92002) *Nat. Biotechnol.*, 20:933), foreskin fibroblasts (see, e.g., Amit et al., (2003) *Biol. Reprod.* 68:2150), uterine endometrial cells (see, e.g., Lee et al., (2005) *Biol. Reprod.* 72(1):42).

In the practice of the present invention, there are various solid surfaces that may be used in the culturing of cells. Those solid surfaces include, but are not limited to, standard commercially available cell culture plates such as 6-well, 24-well, 96-well, or 144-well plates. Other solid surfaces include, but are not limited to, microcarriers and disks. In certain embodiments, the microcarriers are beads. Those beads come in various forms such as Cytodex Dextran microcarrier beads with positive charge groups to augment cell attachment, gelatin/collagen-coated beads for cell attachment, and macroporous microcarrier beads with different porosities for attachment of cells. The Cytodex dextran, gelatin-coated and the macroporous microcarrier beads are commercially available (Sigma-Aldrich, St. Louis, Mo. or Solohill Engineering Inc., Ann Arbor, Mich.). In certain embodiments, the beads are 90-200 μm in size with an area of 350-500 $cm^2$. Beads may be composed of a variety of materials such as, but not limited to, glass or plastic. In certain embodiments, disks may be used in stirred-tank bioreactors for attachment of the cells. Disks are sold by companies such as New Brunswick Scientific Co, Inc. (Edison, N.J.). In certain embodiments, the disks are Fibracel Disks, which are polyester/polypropylene disks. A gram of these disks provide a surface area of 1200 $cm^2$.

The solid surface suitable for growing pPS cells may be made of a variety of substances including, but not limited to, glass or plastic such as polystyrene, polyvinylchloride, polycarbonate, polytetrafluoroethylene, melinex, or thermanox. In certain embodiments of the invention, the solid surfaces may be three-dimensional in shape. Exemplary three-dimensional solid surfaces are described, e.g., in US20050031598.

In certain embodiments, the cells are in a single-cell suspension during the methods of the invention. The single-cell suspension may be performed in various ways including, but not limited to, culture in a spinner flask, in a shaker flask, or in a fermentors. Fermentors that may be used include, but are not limited to, Celligen Plus (New Brunswick Scientific Co, Inc., Edison, N.J.), and the STR or the Stirred-Tank Reactor (Applikon Inc., Foster City, Calif.). In certain embodiments, the bioreactors may be continuously perfused with media or used in a fed-batch mode. Bioreactors come in different sizes including 2.2 L, 5 L, 7.5 L, 14 L or 20 L.

General Techniques

For further elaboration of general techniques useful in the practice of this invention, the practitioner can refer to standard textbooks and reviews in cell biology, tissue culture, embryology, and immunology.

With respect to tissue and cell culture and embryonic stem cells, the reader may wish to refer to any of numerous publications available in the art, e.g., *Teratocarcinomas and Embryonic Stem cells: A Practical Approach* (E. J. Robertson, ed., IRL Press Ltd. 1987); *Guide to Techniques in Mouse Development* (P. M. Wasserman et al. eds., Academic Press 1993); *Embryonic Stem Cell Differentiation in Vitro* (M. V. Wiles, Meth. Enzymol. 225:900, 1993); *Properties and Uses of Embryonic Stem Cells: Prospects for Application to Human Biology and Gene Therapy* (P. D. Rathjen et al., Reprod. Fertil. Dev. 10:31, 1998; and R. I. Freshney, Culture of Animal Cells, Wiley-Liss, New York, 2000). With respect to the biology of hematopoietic lineage cells the reader may refer to any immunology textbook, e.g., *Immunobiology: The Immune System in Health and Disease* (Janeway et al., 2001 Garland Publishing).

Where derived from an established line of primate pluripotent stem cells, the cell populations and isolated cells of this invention can be characterized as having the same genome as the line from which they are derived. This means that the chromosomal DNA will be essentially identical by RFLP or by SNP analysis between the primate pluripotent stem cells and the differentiated progeny cells (assuming the cells have not been genetically manipulated by the human hand). It is understood that minute alterations, e.g. in non-coding regions are possible; however the genetic identity between the line of pPS cells and the respective progeny will be comparable to that seen in identical twins.

Genetic Alteration of Differentiated Cells

The cells of this invention can be made to contain one or more genetic alterations by genetic engineering of the cells either before or after differentiation (US 2002/0168766 A1). For example in some embodiments, the cells can be processed to increase their replication potential by genetically altering the cells to express telomerase reverse transcriptase, either before or after they progress to restricted developmental lineage cells or terminally differentiated cells (US 2003/0022367 A1).

The cells of this invention can also be genetically altered in order to enhance their ability to be involved in modulating an immune response, or to deliver a therapeutic gene to a site of administration. A vector is designed using the known encoding sequence for the desired gene, operatively linked to a promoter that is either pan-specific or specifically active in the differentiated cell type. Alternatively the promoter may be an inducible promoter that permits for the timed expression of the genetic alteration. For example the cells may be genetically engineered to express a cytokine that modulates an immune response either by enhancing the response or dampening the response.

In the following Examples all experiments utilizing human embryonic cells (hES) cells were performed using established hES cell lines.

EXAMPLES

Example 1

Differentiation of hES Cells to mDC by Varying the Differentiation Cocktail

Figures 1B, 1C:
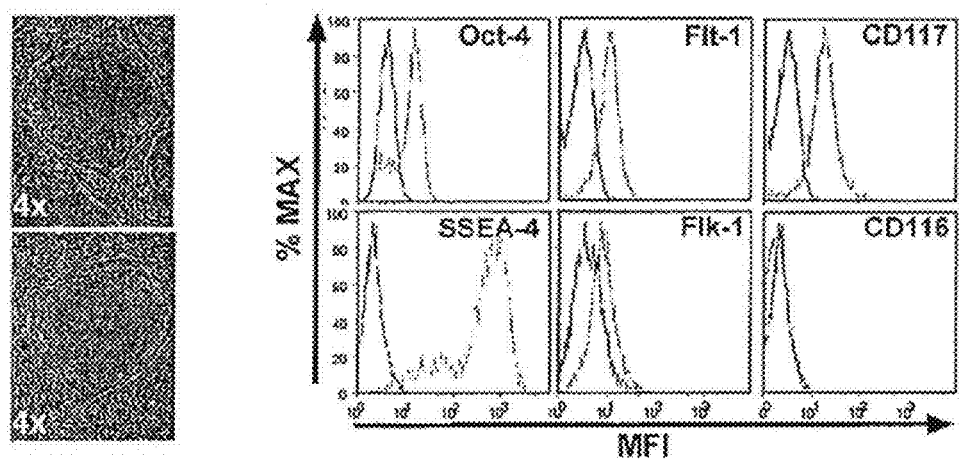
FIG. 1B is a photograph of a light microscopy image of hES cells grown in X-VIVO™ 10 media.
FIG. 1C is a flow cytometric histogram showing the expression level of various markers found on undifferentiated hES.

In this example pPS cells were differentiated into mDC by first culturing the pPS cells with a differentiation cocktail to obtain imDC and then further culturing the imDC with a maturation cocktail. The differentiation cocktail comprised exogenous cytokines which varied over the course of the experiment as the cells were differentiated to the imDC stage. (FIG. 1a). Human ES cell line H1 (Thomson et al., (1998) *Science* 282:1145) were cultured feeder free in defined serum-free media devoid of animal-derived products (Xu et al., (2001) *Nat Biotechnol* 19:971; Li et al., (2005) *Biotechnol Bioeng* 91:688) (FIG. 1b). The cells were also cultured stromal cell free throughout the differentiation and maturation protocol.

The hES cells were cultured under conditions permissive for forming embryoid bodies (EBs). Briefly, H1 cells were treated with collagenase D, (Invitrogen, Carlsbad, Calif.) rinsed once with 1×PBS, and gently scraped off the plate with a cell scraper (Corning Life Sciences, Corning, N.Y.). The cells were then plated in 6 well ultra low attachment plates (Corning Life Sciences, Corning, N.Y.) at 3 million cells/well in X-VIVO 15 media (Lonzo, Walkersville, Md.) supplemented with 1 mM Na-Pyruvate (Invitrogen, Carlsbad, Calif.), 1× non-essential amino acids (Invitrogen, Carlsbad), Calif., 2 mM L-glutamine (Invitrogen, Carlsbad, Calif.), $5 \times 10^{-5}$ M 2-Mercaptoethanol (Sigma, St Louis, Mo.), and 10 mM HEPES (Invitrogen, Carlsbad, Calif.) and allowed to form embryoid bodies. The following growth factors were added to the medium: SCF (20 ng/ml), VEGF (50 ng/ml), BMP-4 (50 ng/ml), and GM-CSF (50 ng/ml). All growth factors were purchased from R&D Systems (R&D Systems, Minneapolis Minn.). Each well contained 4 ml of media. The cells were fed every two to three days with a 1:3 media change.

Figure 2A:
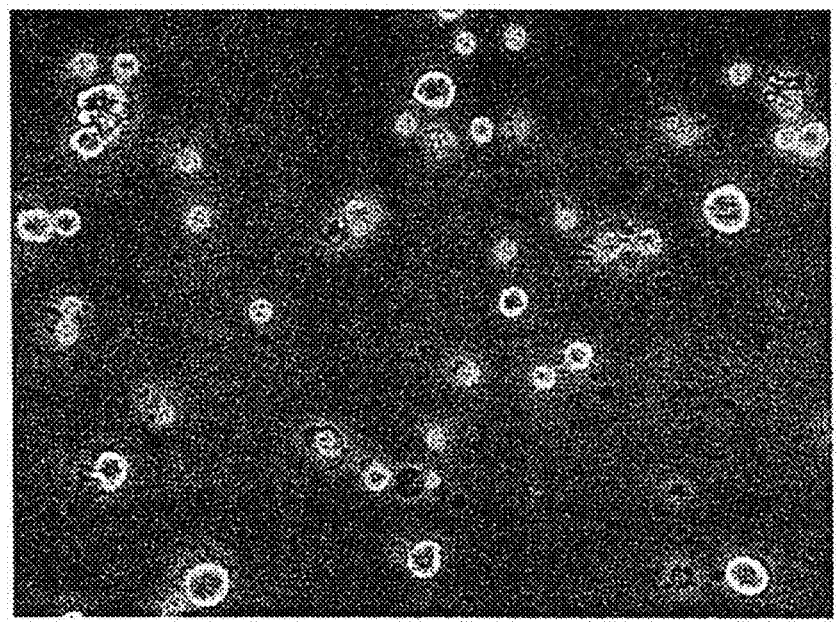
FIG. 2A and FIG. 2B are photomicrographs of embryoid bodies (FIG. 2B) and progenitor cells (FIG. 2A).
Figure 2B:
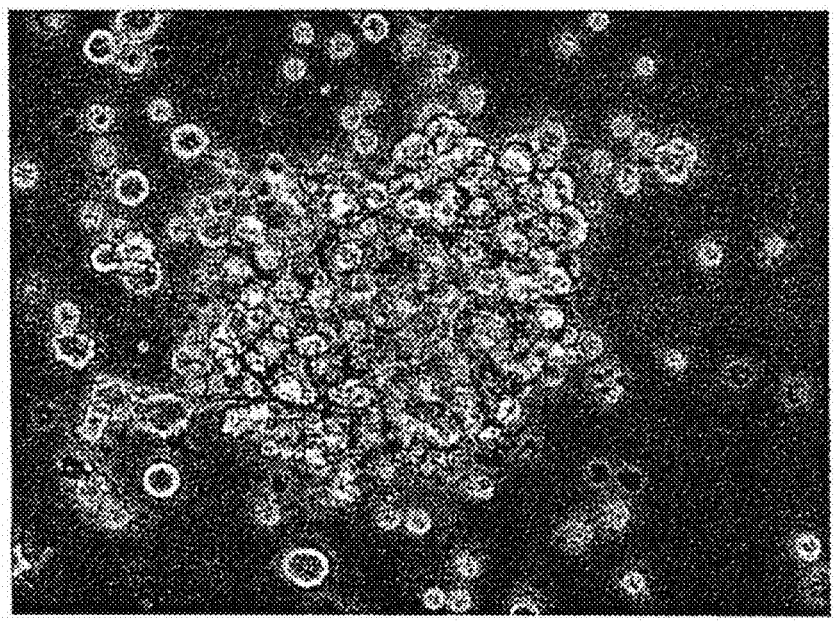

On day 5 BMP-4 was removed from the growth factor cocktail, on day 10 VEGF was removed from the growth factor cocktail, and on day 15 SCF was removed from the growth factor cocktail (FIG. 1A). At around d17-d25 round shining hematopoietic progenitor cells were visible (FIG. 2). When about 100,000 to about 1 million floating shining progenitor cells were visible in the wells, they were harvested, spun down and reseeded in the original 6 well ultra low attachment plates and cultured in X-VIVO 15 (Lonzo, Walkersville, Md.) with GM-CSF (50 ng/ml) and IL-4 (50 ng/ml) (R&D Systems, Minneapolis, Minn.) to generate imDC. The original EBs were moved to new 6 well ultra low attachment plates for about 40-50 days and fed with media comprising GM-CSF (50 ng/ml) every 2-3 days (1:3 media change) and continued to produce shiny hematopoietic cells which were harvested and then further cultured and differentiated with GM-CSF and IL-4 to produce additional imDC.

Flow cytometric analysis on the hES cells was performed as follows: the cells were resuspended in 50 µl of Flow buffer (PBS+0.1% BSA+2 mM EDTA) and blocked using an anti-FC receptor antibody (Miltenyi, Aurburn, Calif.) for 10 minutes at 4° C. and then antibodies to the target marker were added (antibodies are provided below in Table I). After incubation for 20 minutes at 4° C., the cells were washed 2× in Flow buffer, and 5 minutes before sample analysis 2 ul 7AAD (0.25 ug/1×10$^6$ cells) (BD Bioscience, San Jose, Calif.) was added per sample in order to assess cell viability. Sample data were collected using a FACSCalibur™ (Becton Dickinson, San Jose, Calif.), and analyzed using FlowJo® software (Treestar, Ashland, Oreg.). For intracellular Oct-4 staining the cells were fixed using an intracellular fixation buffer (eBioscience, San Diego, Calif.) and made permeable using a permeabilization buffer (eBioscience, San Diego, Calif.) according to the manufacturer's instructions. As expected the cells expressed Oct-4 and SSEA-4 both markers of hES cells. In addition the cells also expressed Flt-1 and Flk-1 both receptors for VEGF, as well as CD117, the receptor for SCF. CD116, the GM-CSF receptor, was not detected (FIG. 1C).

Figure 4A:
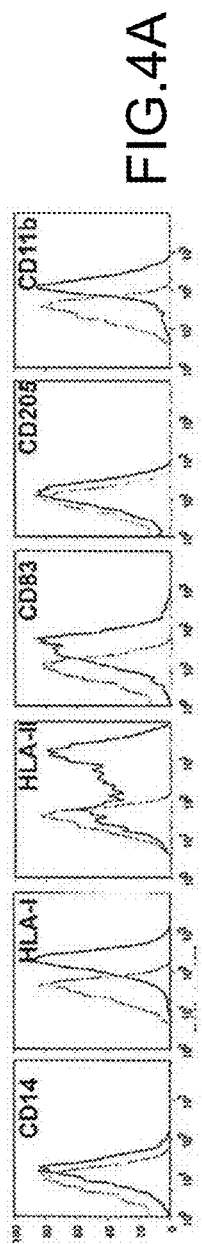
FIG. 4A shows a flow cytometric histogram analysis of markers for imDC.
Figure 4B:
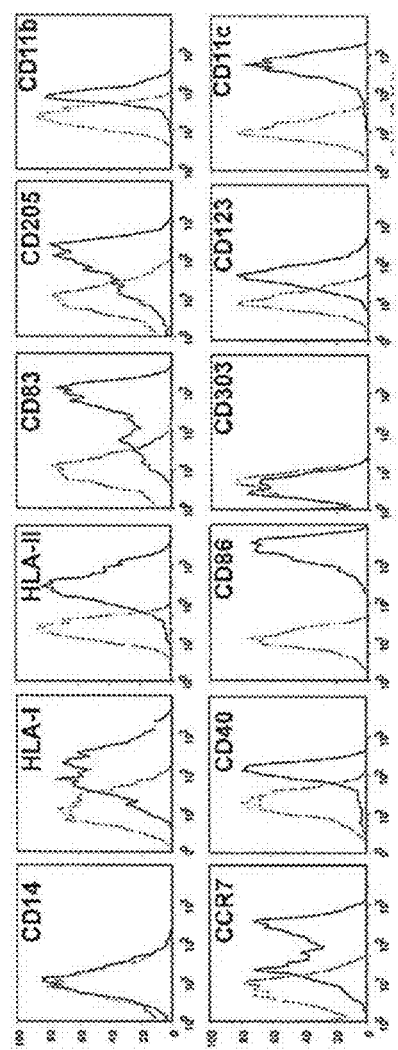
FIG. 4B shows a flow cytometric histogram analysis of markers for mDC.

The imDC were analyzed by flow cytometry (as described above) for the following markers: CD14, HLA-I, HLA-II, CD83, CD205 and CD11b. The cells were found to be positive for HLA-I, HLA-II, CD83, and CD11b (FIG. 4A). After 4-6 days these immature DC were spun down and resuspended in X-VIVO 15 media comprising the following cytokines IFN-γ (25 ng/ml), IL-1-β (10 ng/ml), TNF-α (10 ng/ml), PGE2 (1 µg/ml) and GM-CSF (50 ng/ml) (the maturation cocktail). The cells were maintained in culture for an additional 48 hours to generate matured DC. The mDC were analyzed by FACs (as described above) and found to express the following markers: HLA-I, HLA-II, CD40, CD86, CD83, CD205, CD11c$^{hi}$, and CCR7. The cells were negative for CD14 (FIG. 4B). CD83 is a marker for dendritic cell maturation. CCR7 is a chemokine receptor involved in DC migration. The expression profile was comparable to DC derived from peripheral blood mononuclear cells (PBMC). The cells were also analyzed by real time quantitative PCR for expression of the following transcription factors: NF-κB, CIITA and Spi-B (FIG. 4C). Spi-B has been shown to be expressed in DC derived from PBMCs (Schotte et al., (2003) *Blood* 101(3):1015; Rissoan et al., (2002) *Blood* 100(9):3295; Schotte et al., (2004) *J. Exp. Med.* 200(11):1503; Chicha et al., (2004) *J. Exp. Med.* 200(11):1519. NF-κB is associated with costimulatory molecule expression and is necessary for the DC activation process. CIITA is a master regulator of HLA-II expression.

Figures 4D, 4E:
FIG. 4D is a photomicrograph of a DC cluster.
FIG. 4E is a photomicrograph of DC stained with May Grunwald stain.
Figure 4C:
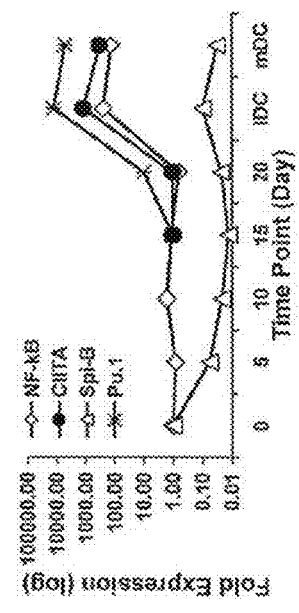
FIG. 4C is a graph showing transcription factor expression in differentiating cell cultures over time.

The cells were analyzed morphologically and were found to have a morphology typical of DC (FIG. 4D). To further study the morphology of the mDC the cells were stained with May-Grunwald stain. The cells were washed with 1×PBS, resuspended in 50 ul of 1×PBS, added onto glass slides prepared with the cytospin apparatus. Ten ul of the cell suspension was applied to the slide. The slides were spun at 1200 rpm for 5 minutes using a ShandonCytospin3 (Thermo Scientific, Waltham Mass.). The cells were then stained with May Grunwald Staining solution (Sigma, St Louis, Mo.) for 5 minutes at 25° C., washed 3× with dH$_2$O, and air dried overnight. The sample area was coated with Permount® (Sigma, St Louis, Mo.), a glass cover slip was applied, and the slide was allowed to dry overnight. Images were taken with an upright microscope with 100× planar objective and 40× Plan-Neofluar objective (Zeiss, Peabody, Mass.). The results shown in FIG. 4E demonstrated that the mDC had morphology typical of a dendritic cell isolated from PBMCs that included branched projections or dendrites emanating out from the cell. The cells were also analyzed by flow cytometry (as described above) for CD19, CD3, CD235a and CD41 (indicative of B cells, T cells, erythrocytes, and platelets, megakaryocytes, respectively), but were found to be undetectable for all of these markers. The preparation was found to have 5-20% granulocytes and 5-20% progenitor cells. The population of cells ranged from about 50% to about 90% DC.

Example 2

Time Course Analysis of Differentiating Cell Cultures

In order to characterize precursor cell populations arising during the process of differentiating pPS to imDC, the cell culture described in Example 1 was evaluated over time for transcription factor expression using RT PCR and real time quantitative PCR (as described below) and by flow cytometry (as described above) over time for expression of cell surface markers.

Figure 3B:
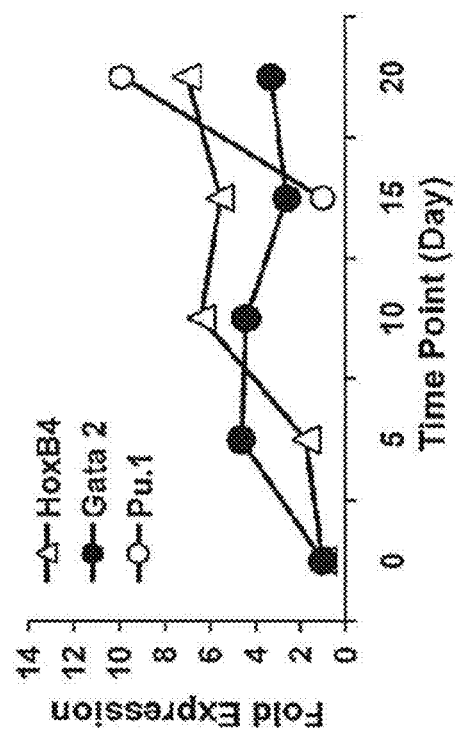
FIGS. 3A and 3B are graphs showing expression of various transcription factors over time in a cell culture undergoing differentiation.
Figure 3A:
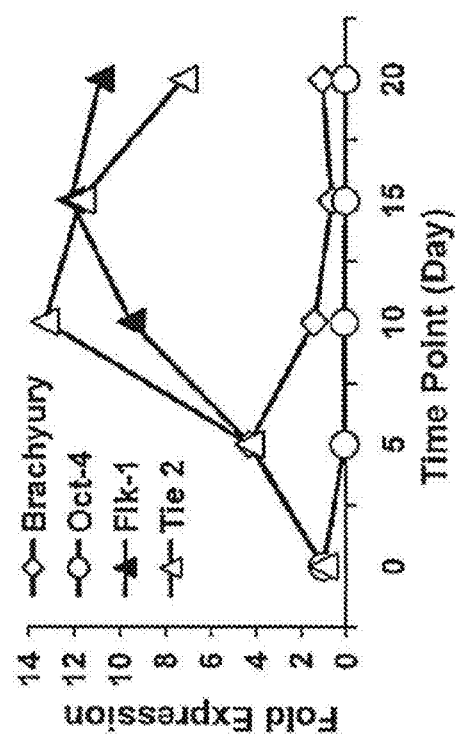

For real time quantitative PCR target cells were harvested and total RNA was isolated following the standard Qiagen RNeasy® Mini Prep protocol (Qiagen, Valencia, Calif.). Qiagen QiaShredder (Qiagen, Valencia, Calif.) was used to homogenize the lysate. Isolated RNAs were stored at −80° C. For cDNA synthesis, 1 µg RNA samples were treated with DNase (Ambion, Austin Tex.) to remove any genomic DNA impurities from the RNA prep. Reverse Transcriptase PCR (RT-PCR) was performed using Superscript II™ (Invitrogen, Carlsbad, Calif.) first strand synthesis system to make cDNA. The cDNA product was diluted 1:5 in water and used as a template for the Taqman® PCR Cycle Threshold (CT) Real Time Quantitation (Applied Biosystems, Foster City, Calif.). Samples were run on Applied BioSystems 7900HT Sequence Detection System (Applied Biosystems, Foster City, Calif.). The data were analyzed for relative expression level by normalizing the target signal against the target signal at day 0. FIGS. 3a and 3b provide the results. By day 5 expression of Oct-4 decreased 20 fold. The five fold increase of brachyury by day 5 indicated the cells had differentiated into mesoderm. Flk-1 is found on hematopoietic stem cells. The increased expression of Flk-1 suggested the differentiation of a hemogenic cell population. The expression of Tie-2 suggested the differentiation of hemangioblasts. Hemangioblasts are comprised of cells with both hematopoietic and endothelial potential.

FIG. 3b shows expression levels of additional transcription factors over time. Increased expression levels of both HoxB4 and Gata2 suggested that the cells have differentiated into a hematopoietic cell population. HoxB4 plays a role in hematopoietic stem cell renewal and survival (Antonchuk et al., (2002) *Cell* 109(1):39. Gata2 is an early hematopoietic transcription factor that is also expressed in GMP.

Flow cytometry was performed as described in Example 1. Antibodies used in all flow cytometry experiments are listed below in Table I.

TABLE I

| | |
|---|---|
| SSEA-4 | R&D Systems |
| 4-Oct | Santa Cruz Biotechnology |
| CD117 | BD Bioscience |
| Flt-1 | R&D Systems |
| RD-KDR | R&D Systems |
| CD116 | BD Bioscience |
| CD19 | BD Bioscience |
| CD3 | eBioscience |
| CD11b | BD Bioscience |

TABLE I-continued

| | |
|---|---|
| CD11c | BD Bioscience |
| CD13 | BD Bioscience |
| CD15 | BD Bioscience |
| CD34 | BD Bioscience |
| CD38 | BD Bioscience |
| CD40 | BD Bioscience |
| CD44 | BD Bioscience |
| CD45 | BD Bioscience |
| CD80 | BD Bioscience |
| CD86 | BD Bioscience |
| CD83 | BD Bioscience |
| HLA-I | BD Bioscience |
| HLA-II | BD Bioscience |
| CD205 | BD Bioscience |
| CD303 | Miltenyi |
| CD123 | BD Bioscience |
| CCR7 | BD Bioscience |

Figure 3D:
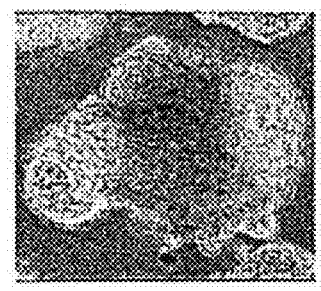
FIG. 3D is a photomicrograph of a cystic embryoid body.
Figure 3C:
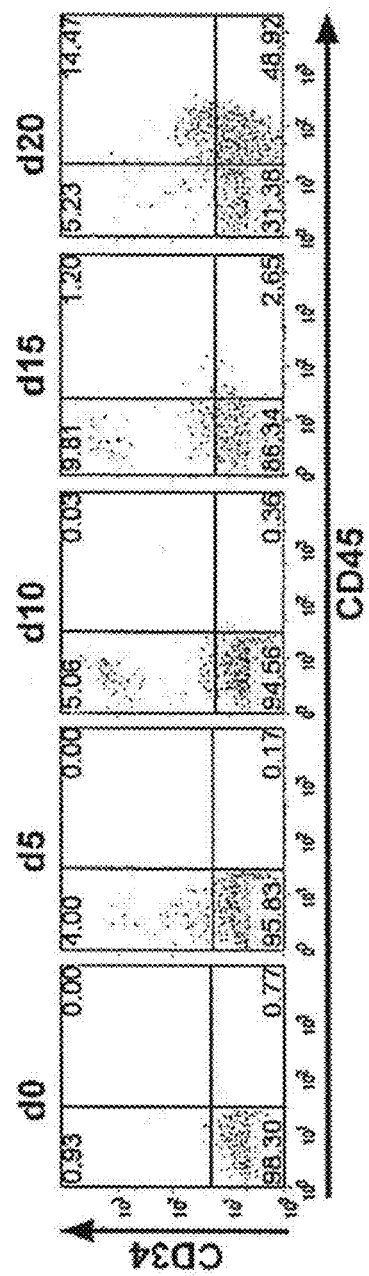
FIG. 3C shows expression of CD34 and CD45 over time as measured by flow cytometry in a cell culture undergoing differentiation.
Figure 3E:
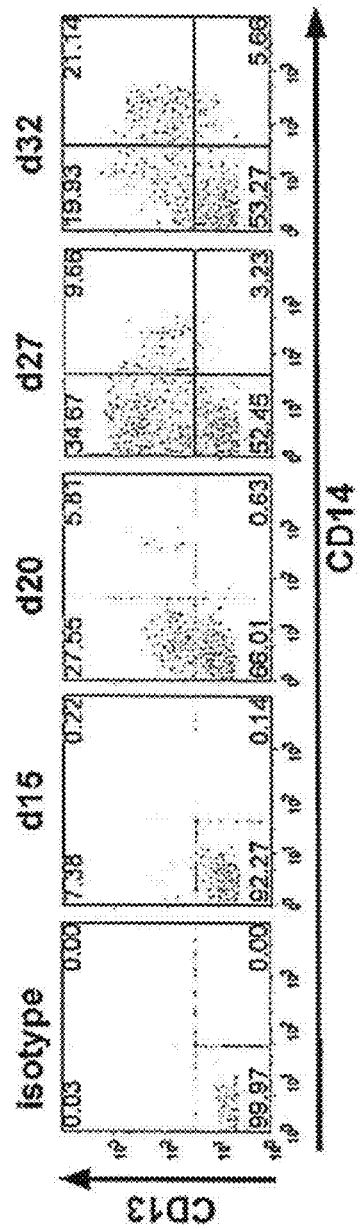
FIG. 3E shows expression of CD13 and CD14 over time as measured by flow cytometry in a cell culture undergoing differentiation.
Figure 3G:
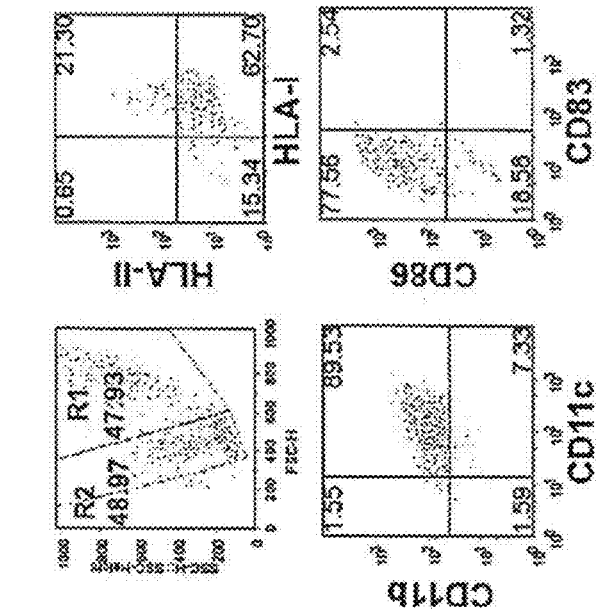
FIG. 3G shows expression of CD11c, CD11b, CD83, CD86 (bottom two panels), HLA-I and HLA-II (top right panel) in a $CD45^{hi}$ population as measured by flow cytometry. The top left panel shows gating of the CD45hi and lo populations.
Figure 3F:
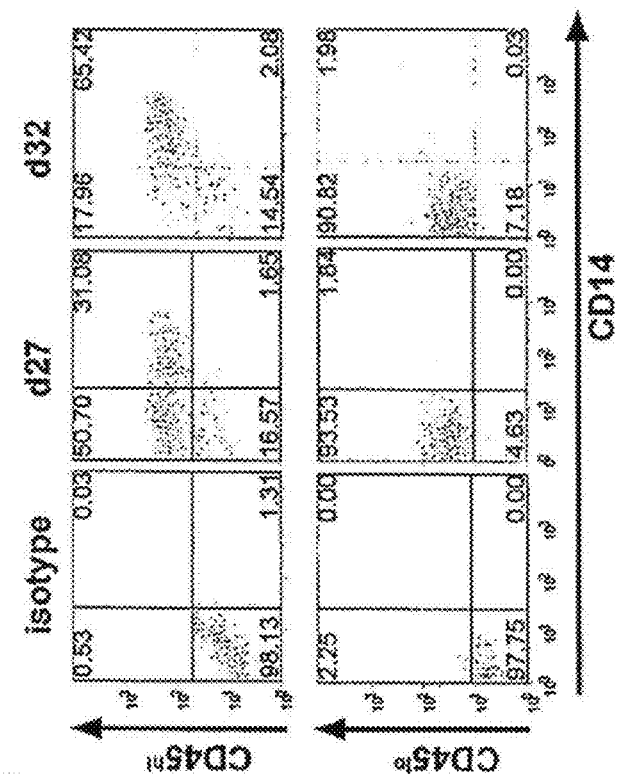
FIG. 3F shows expression of CD14 in both $CD45^{hi}$ population (top 2 panels) and $CD45^{lo}$ population (lower two panels) as measured by flow cytometry.

FIGS. 3c and 3d shows the results of the flow cytometric study for expression of CD45 and CD34 over time. The expression of CD34 by day 5 was indicative of early hematopoiesis. By day 5 the morphology of the culture had taken on the appearance of a cystic embryoid body (FIG. 3e). By day 15 expression of CD45, a pan-hematopoietic cell marker, was apparent. At the same time transcription factor PU.1 was detected by real time quantitative PCR (FIG. 3b). PU.1 expression is found in early hematopoietic cells and its expression level increases as the cells differentiate to dendritic cells (Guerriero et al., (2000) *Blood* 95(3): 879; Nutt et al., (2005 *J Exp. Med.* 201(2):221). Myeloid lineage marker CD13 expression became apparent by day 15 (FIG. 3F). This suggested that by the time SCF was removed from the differentiation cocktail the cells had already entered the hematopoietic and myeloid lineage. Monocyte marker CD14 was expressed by day 20 (FIG. 3F). Expression of both CD13 and CD14 increased with time (FIG. 3F).

By day 20 it became apparent that there were two CD45+ populations in the culture: $CD45^{hi}$ and $CD45^{lo}$ (FIG. 3G). The expression of CD14 increased over time in the $CD45^{hi}$ population. By day 32 65% of the cells expressed CD14 and CD45. CD14 expression was not seen in the $CD45^{lo}$ population (FIG. 3G). The $CD45^{hi}$ population correlated with cells in the monocyte/dendritic cell gate named (R1) while the $CD45^{lo}$ population correlated with the granulocyte progenitor cell gate named (R2) in the forward scatter versus side scatter plot (FIG. 3G). The $CD45^{hi}$ population was characterized further at day 32 of the differentiation protocol and found to be positive for CD11c, CD11b, HLA-I, HLA-$II^{lo/neg}$ and CD86 (FIG. 3H) all suggesting the cells were imDC. CD86 is a costimulatory molecule involved in T cell activation, while CD83 is mDC marker. Lack of CD83 expression indicated the cells were not mDC.

Example 3

Antigen Processing and Presentation

Figure 5A:
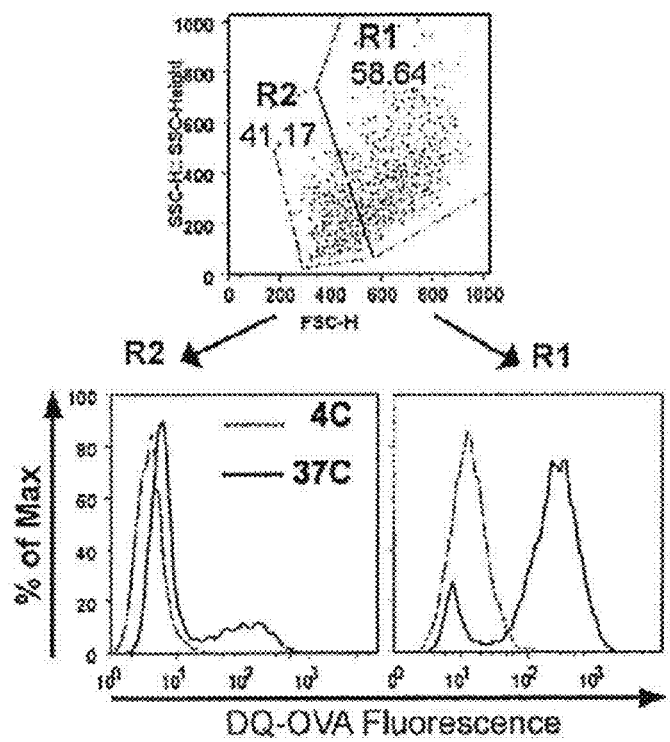
FIG. 5A shows gating of cells by flow cytometry for dendritic cells (R1) (top panel) and demonstrates that the cell population gated for dendritic cells can take up and proteolytically process the model antigen DQ-OVA (lower panel).

To test the ability of the hES derived imDC to process antigen, the fluorescent dye, DQ-OVA (Invitrogen, Carlsbad, Calif.), was dissolved at 1 mg/ml in PBS and added at 100 μg/ml to imDC derived from hES as described in Example 1. The protein was labeled with a pH insensitive BODIPY-F1 dye. The dye is self quenching when the protein is intact, but fluoresces bright green when the protein is denatured or undergoes proteolysis. The cells were incubated either at 37° C. or at 4° C. (as a control for background fluorescence) and washed 2× with flow buffer. Data was collected with FACSCalibur™ (Becton Dickinson, San Jose, Calif.) in FL1. The treated cells were found to fluoresce indicating that the protein had been proteolyzed by the imDC, while the control cells did not (FIG. 5a).

Figure 5B:
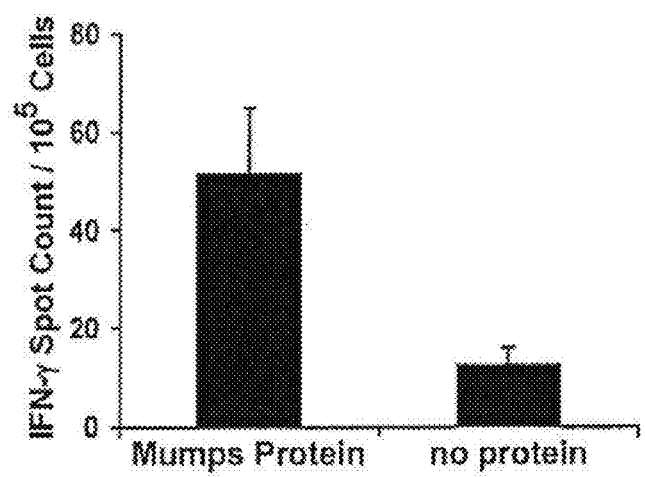
FIG. 5B is a graph showing that DC can process and present mumps antigen to induce IFNγ production by T lymphocytes.

A functional assay was performed next to determine if DC made according to the method of Example 1 were able to stimulate antigen specific lymphocyte secretion of IFNγ, one hallmark of the adaptive immune response. Mumps protein was used as the stimulatory antigen (Biodesign, Saco, Me.). The protein was added at 100 ug/ml for 1 hour to imDC derived from hES as described in Example 1. The maturation cocktail described earlier IFN-γ (25 ng/ml), IL-1-β (10 ng/ml), TNF-α (10 ng/ml), PGE2 (1 μg/ml) and GM-CSF (50 ng/ml) was added next. After 24 hours, matured DC, either untreated or treated with mumps protein, were collected, and washed 2× with AIM-V media (Invitrogen, Carlsbad, Calif.). The DC were plated at $1\times10^4$ cells/well together with $1\times10^5$ PBMCs/well (Cellular Technologies LTD, Shaker Heights, Ohio) IFNγ ELISPOT plates were used for the read out (Millipore Corp. Bedford, Mass.). ELISPOT plates were coated with anti-IFNγ Ab (Mabtech, Mariemont, Ohio) at 10 ug/ml overnight (16-24 hours). The assay plate was placed at 37° C. and 5% $CO_2$ for 16-24 hours, and developed following the instructions provided by Mabtech. Spots were counted using a CTL Analyzer (Cellular Technology Limited, Decatur, Ill.). The results presented in FIG. 5B demonstrate a 3 fold difference in IFNγ production by mDC of the invention over the non-treated control.

Example 4

Cytokine Production

A qualitative cytokine array analysis was performed using the Human Cytokine Array III and V kit (Raybiotech, Norcross, Ga.) on both imDC and mDC obtained according to the method described in Example 1. The assay was performed according to the manufacturer's instructions. The mDC were found to produce the following pro-inflammatory cytokines: IL-6, IL-7, IL-8, and Il-10. IL-7 is believed to be important for T cell survival. IL-8 is believed to be a chemotactic stimulus. Cytokines IL-6, IL-10, and IL-12 were quantified using the BD Cytometric Bead Array (BD Biosciences, San Jose, Calif.) following the manufacturers instructions. Supernatants from immature and mature DC derived from hES were collected and concentrated using Amicon Ultra-15 10,000 NMWL (Millipore, Bedford, Mass.) centrifuge tubes. The supernatants were added to human IL-6, IL-10, and IL-12 bead flex sets (BD Biosciences, San Jose, Calif.), and incubated for 1 hour at 25° C. Antibody detection reagent conjugated to PE (BD Biosciences, San Jose, Calif.) was added and incubated for an additional 2 hours at room temperature. Samples were washed 1×, re-suspended in wash buffer (BD Biosciences, San Jose, Calif.), and collected by flow cytometry with a FACSCaliber™ (Becton Dickinson, San Jose, Calif.). Cytokine concentrations were determined using FCAP Array Software (BD Biosciences, San Jose Calif.). The results presented in FIG. 6A demonstrate significant levels of all three cytokines were produced by the mDC.

Example 5

Chemotactic Analysis of mDC

AIM-V media (Invitrogen, Carlsbad, Calif.) was added to the upper and lower chambers of Transwell 24 well plates containing 8.0 uM pore size inserts (Corning, Corning, N.Y.), and incubated overnight at 37° C., 5% $CO_2$. After removal of the media from each well, 0.6 ml of AIM-V with or without the chemokine MIP3β (100 ng/ml) was added to the lower chamber. Mature DC derived from hES (as described in Example 1) were harvested and washed 2× in AIM-V media. The cells were resuspended in AIM-V media at $2.0 \times 10^6$ cells/ml, and 0.1 ml was added to the top chamber. The transwell plate was incubated for 2 hours at 37° C., 5% $CO_2$. The number of cells that migrated to the bottom chamber was determined using a hemacytometer. The results presented in FIG. 6D demonstrated that mDC according to the invention migrate in response to MIP3β.

Example 6

Immunostimulatory Capacity of Dendritic Cells

Several assays were performed to characterize the ability of mDC produced according to the method of Example 1 to stimulate an immune response. First a mixed lymphocyte reaction (MLR) assay was done to demonstrate that the mDC had the ability to stimulate a strong naïve alloresponse.

PBMC derived DC were prepared by isolating peripheral blood mononuclear cells (PBMCs) from fresh healthy donor buffy coat preps. PBMCs were adhered to tissue culture flasks in AIM-V media for 2 hours then washed with warm PBS to remove non-adherent cells. The remaining adherent cells, comprised mostly of monocytes, were incubated at 37° C. and 5% $CO_2$ for 6 days with recombinant human interleukin 4 (rhIL-4) (R&D Systems, Minneapolis Minn.) and recombinant human GM-CSF (rhGM-CSF) (R&D Systems, Minneapolis Minn.) at 1000 U/ml to generate imDC. imDC were then matured for 24 hours in AIM-V media (Invitrogen, Carlsbad, Calif.) with 800 U/ml rhGM-CSF, 10 ng/ml TNFα, 10 ng/ml IL1-β, and 10 ng/ml IL-6 and 1.0 ug/ml PGE2 (R&D Systems, Minneapolis Minn.).

Figure 7A:
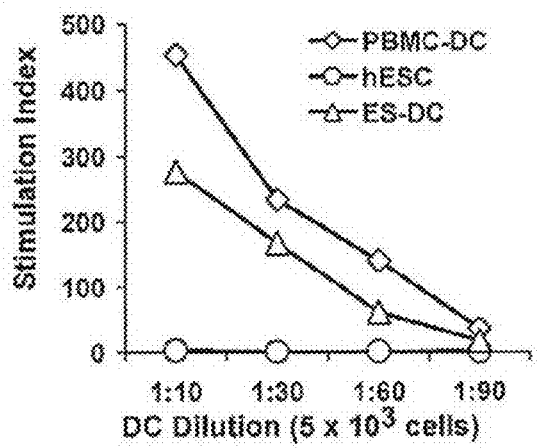
FIG. 7A is a graph showing that mDC can stimulate allogeneic cells in a mixed lymphocyte reaction (MLR).

For MLR assay PBMCs were isolated from buffy coats obtained from healthy volunteers (Stanford Blood Bank) by centrifuging the cells over a Ficoll-Paque gradient (Amersham Pharmacia Biotech AB, Buckinghamshire, UK). Isolated cells were washed and resuspended in complete RPMI 1640 medium (Invitrogen, Carlsbad, Calif.) with 10% FBS (Clonetech, Mountain View, Calif.) and 1% penicillin/streptomycin (Invitrogen, Carlsbad, Calif.). In a 96-well U-bottom plate (Becton Dickinson, San Jose, Calif.), $5 \times 10^4$ PBMCs and different numbers of irradiated stimulator cells (2000 rads for hESCs, monocyte derived DC and hES derived DC) were mixed in a 96-well U-bottom plate (Becton Dickinson, San Jose, Calif.) and incubated at 5% $CO_2$ and 37° C. for five days. The cells were then pulsed with 1 uCi $^3$H thymidine per well for 18 hours at 5% $CO_2$ and 37° C. The cells were harvested onto a UniFilter-96 GF/C (PerkinElmer, Waltham, Mass.) using a Filtermate Harvester (Perkin Elmer, Waltham, Mass.) and $^3$H thymidine incorporation was counted using a TopCount scintillation counter (Perkin Elmer, Waltham, Mass.). The results demonstrated that the mDC produced according to Example 1 had good allogeneic stimulating activity (FIG. 7A).

Next the ability of the mDC to stimulate antigen specific effector T cells was investigated. CMV peptide pp65 (amino acid sequence 495-503) was used to demonstrate DC antigen presentation to CD8+ lymphocytes. Characterized PBMC responders comprising CD8 lymphocytes, which specifically recognize the pp65 peptide were used. The CD8 T-lymphocytes and the DC shared a common HLA-A2 allele. For CMV specific antigen presentation, matured PBMC-DC and hES derived DC were resuspended in 150 ul of serum free AIM-V medium (Invitrogen, Carlsbad, Calif.) either supplemented with 10 µg/ml CMV pp65 peptide or unsupplemented. The cells were incubated at 37° C. and 5% $CO_2$ for 2 hours, and then washed 2× with AIM-V media (Invitrogen, Carlsbad, Calif.). DC were plated onto an ELISPOT plate at $1 \times 10^4$ cells/100 ul/well at a 10:1 responder to stimulator ratio. Characterized PBMC responders, specific for CMV, (Cellular Technologies Limited, Decatur, Ill.) were thawed in 37° C. water bath, washed two times, resuspended in AIM-V media (Invitrogen, Carlsbad, Calif.), and plated at $1 \times 10^5$ cells/100 ul/well on ELISPOT plates (Millipore, Bedford Mass.). ELISPOT plates were coated with anti-IFNγ Ab (Mabtech, Mariemont, Ohio) at 10 ug/ml overnight (16-24 hours). The assay plate was placed at 37° C. and 5% $CO_2$ for 16-24 hours, and developed following the instructions provided by Mabtech. Spots were counted using a CTL Analyzer (Cellular Technology Limited, Decatur, Ill.). The results, shown in FIG. 7b, demonstrated that mDC (labeled ES-DC in the figure) were able to stimulate IFNγ production that was comparable to PBMC-DC.

Next the ability of mDC to stimulate T cell expansion in vitro was examined. A CMV T cell line (67% specificity) (ProImmune, Bradenton, Fla.) was thaw at 37° C. and washed 2× with 1640 RPMI medium (Invitrogen, Carlsbad, Calif.)+5% FBS (Invitrogen, Carlsbad, Calif.) supplemented with 1 mM Na-Pyruvate, non-essential amino acids, 2 mM L-glutamine, $5 \times 10^{-5}$ M 2-Mercaptoethanol, and HEPES. The T cells were then incubated at 37° C. and 5% $CO_2$ for 2 hours. 5 mM CellTrace CFSE stock solution (Invitrogen, Carlsbad, Calif.) was dissolved immediately prior to use in DMSO (Invitrogen, Carlsbad, Calif.). The T cells were resuspended in pre-warmed PBS/0.1% BSA at $1 \times 10^6$/ml. The dye was added to the cells at a final concentration of 2 uM and incubated at 37° C. for 10 minutes. The Celltrace dye was quenched by the addition of 5× ice-cold culture media. The cells were washed 2× before setting up the assay.

Figure 7C:
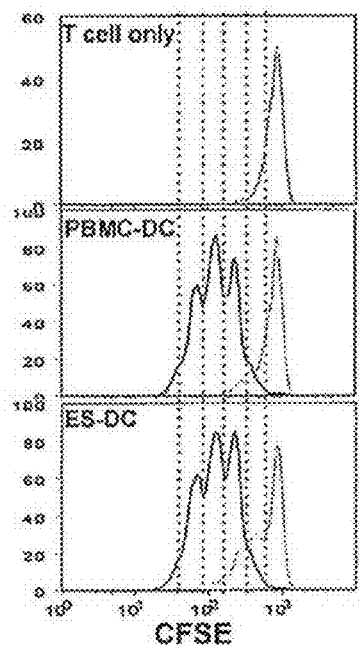
FIG. 7C shows a flow cytometry analysis of CFSE labeled T lymphocyte proliferation in response to a CMV peptide presented on HLA-A2 by mDC (ES-DC).
Figure 7B:
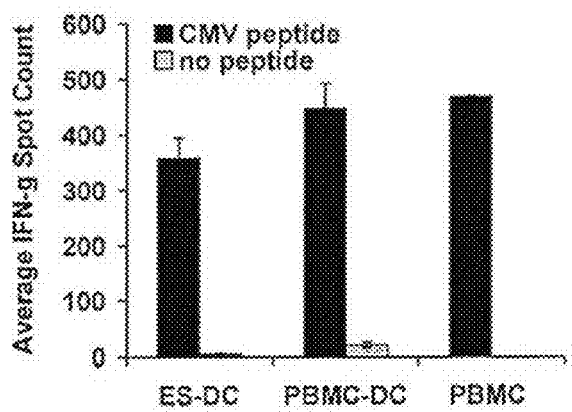
FIG. 7B is a graph showing stimulation of IFN-y secretion by effector T cells m response to a CMV peptide antigen presented on HLA-A2 by mDC (ES-DC).

DC derived from hES were prepulsed with 10 µg/ml of CMV495-503 pp65 peptide (Anaspec, San Jose, Calif.) (>95% pure by HPLC) for 2 hours at 37° C. and washed 2× before plating at $2 \times 10^4$/well in 96 well U bottom Falcon™ plate (BD, San Jose, Calif.). CFSE labeled T cells were plated at $2 \times 10^5$ cells/well. On day 5, cells were harvested and stained with 5 µl of CMV495-503 specific pentamer labeled with APC (ProImmune, Bradenton, Fla.) per million cells at 25° C. for 10 minutes. This recognized T cells specific for the CMV peptide 495-503. This permitted gating the FACS on this specific population of cells for the CFSE analysis. The cells were washed 2× with flow buffer, stained with 7AAD for 5 minutes before running the samples on the FACSCalibur™ (Becton Dickinson, San Jose, Calif.). Dead cells were excluded from analysis by 7AAD. Dilution of the dye label (multiple peaks) is indicative of T cell proliferation. As shown in FIG. 7C the DC made according to Example 1 (ES-DC in the figure) caused T cell proliferation comparable to PBMC-DC. The CD8 T lymphocytes and the dendritic cells shared a common HLA-A2 allele.

Example 7

Comparison of Differentiation Cocktails

The culture conditions for growing and differentiating hES cells to imDC and mDC was performed as described in Example 1 except that the differentiation cocktail used was changed to compare differentiation cocktails comprising a variety of exogenous cytokines. Various combinations of 7, 5, 4 and 3 cytokines (growth factors) were tested for their ability to differentiate hES cells to imDC. Table II provides details regarding experiments in which the differentiation cocktail comprised 7, 5, and 4 exogenous cytokines (plus signs indicate the presence of the factor/minus signs indicate the factor was not used) The numbers in the bottom half of the table indicate the percentages of each cell marker obtained with the corresponding cocktail indicated directly above the percentages. Table III provides details in which the differentiation cocktail comprised 4 and 3 exogenous cytokines (plus signs indicate the presence of the factor/minus signs indicate the factor was not used). The setup regarding percentages of markers obtained relative to the corresponding cocktails is indicated in the bottom half of the table where the percentages correspond to the cocktail shown above the numerical data. Tables IV-VI provide details regarding the composition of the differentiation cocktail (as described in Tables II and III) over the time course of the experiment ("X"s indicate the factor was present for the specified period) ("d" is used in these tables as an abbreviation for "day").

imDC were matured to mDC using two different maturation cocktails. In the experiments described in Table II a maturation cocktail comprising GM-CSF, Il-1β, IFN-γ, CD40L and IFNα was used. In the experiments described in Table III a maturation cocktail comprising TNFα, IL1β, IFNγ and PGE2 was used. Table VII provides the concentration and source of each of the cytokines (growth factors) tested.

TABLE II-continued

|     |       |              |              |              |
|-----|-------|--------------|--------------|--------------|
| d 30 | CD14  | 23.1 ± 8.15  | 23.7 ± 8.4   | 25.3 ± 8.7   |
|     | CD45  | 89.6 ± 1.29  | 91.7 ± 0.73  | 86.5 ± 2.94  |
|     | CD11c | 82.7 ± 1.67  | 83.1 ± 1.39  | 72.5 ± 4.61  |
| iDC | CD14  | 22.2 ± 3.74  | 25.4 ± 4.56  | 26.8 ± 4.15  |
|     | CD86  | 65.5 ± 3.9   | 67.4 ± 4.29  | 71.7 ± 3.02  |
|     | CD83  | 37.8 ± 1.74  | 47.6 ± 2.55  | 45.3 ± 3.51  |
|     | MHC II| 34.2 ± 7.5   | 31 ± 4.78    | 25.6 ± 6.03  |
| mDC | CD86  | 63.9 ± 4.51  | 73.4 ± 4.48  | 74.9 ± 2.58  |
|     | CD83  | 63.3 ± 3.8   | 69.8 ± 5.09  | 71 ± 3.83    |
|     | MHC II| 43.3 ± 5.23  | 46.6 ± 6.08  | 34.5 ± 7.26  |
|     | CCR7  | 44.7 ± 5.32  | 56.7 ± 6.41  | 57 ± 4.79    |

| yield[#] | | | |
|---|---|---|---|
| $10^3$ cells/well* | 335 ± 92 | 385 ± 7.1 | 666 ± 182 |

% cells positive of total population.
Average is n = 4 with mean standard error.
*Differentiations were done in ultra low attachment 6 well plates.
[#]average of n = 2.

TABLE III

Growth Factor Reduction Experiment

| BMP-4  | + | − | + | + | + |
|--------|---|---|---|---|---|
| GM-CSF | + | + | − | + | + |
| VEGF   | + | + | + | − | + |
| SCF    | + | + | + | + | − |

| Time | Marker | | | % positive | | |
|------|--------|------|------|------------|------|------|
| d 20 | CD34   | 26.5 | 11.3 | 1.3 ± 0.17 | 14 ± 9.5   | 20.8 ± 16.5 | 18.4 ± 11.4 |
|      | CD45   | 76.4 | 10.9 | 1.2 ± 0.54 | 7.6 ± 6.4  | 30.1 ± 27.2 | 54.2 ± 25.7 |
|      | CD11c  | 42.1 | 20.8 | 1.5 ± 0.74 | 1.9 ± 0.4  | 4.2 ± 2.7   | 27.8 ± 23.4 |
| d 30 | CD45   | 70.7 | 10.8 | 0.7 ± 0.4  | 12 ± 7.1   | 51 ± 23     | 77.3 ± 6    |
|      | CD11c  | 69.6 | 5.9  | 0.7 ± 0.4  | 9 ± 4.5    | 46.7 ± 21.4 | 65.4 ± 5.9  |
|      | CD14   | 23   | 5.8  | 0.8 ± 0.6  | 8.3 ± 5    | 20.8 ± 11   | 27.6 ± 7.9  |

% cells positive of total population.
*Differentiations were done in ultra low attachment 6 well plates
Average is n = 3 with mean standard error

TABLE II

Growth Factor Reduction Experiment

| BMP-4  | + | + | + |
|--------|---|---|---|
| GM-CSF | + | + | + |
| VEGF   | + | + | + |
| SCF    | + | + | + |
| Flt3-L | + | + | − |
| TPO    | + | − | − |
| IL-3   | + | − | − |

| Time | Marker | % positive | | |
|------|--------|-------------|-------------|-------------|
| d 20 | CD45   | 67.2 ± 6.71 | 72.1 ± 5.2  | 71.2 ± 7.46 |
|      | CD11c  | 39.2 ± 6.49 | 42.9 ± 6.33 | 36.7 ± 7.23 |

TABLE IV

| 7 growth factors | | | | | | |
|---|---|---|---|---|---|---|
| BMP-4 | IL-3 | VEGF | TPO | SCF | flt3L | GM-CSF |
| d 0-5 | x | x | x | x | x | x | x |
| d 6-10 |   | x | x | x | x | x |
| d 11-15 |   |   |   |   | x | x | x |
| d 16 on |   |   |   |   |   | x | x |

TABLE V

| | 5 growth factors | | | | | 4 growth factors | | | |
|---|---|---|---|---|---|---|---|---|---|
| | BMP-4 | VEGF | SCF | flt3L | GM-CSF | BMP-4 | VEGF | SCF | GM-CSF |
| d 0-5 | x | x | x | x | x | x | x | x | x |
| d 6-10 | | x | x | x | x | | x | x | X |
| d 11-15 | | | x | x | x | | | x | x |
| d 16 on | | | | x | x | | | | x |

TABLE VI

| | 3 growth factors | | | 3 growth factors | | | 3 growth factors | | | 3 growth factors | | |
|---|---|---|---|---|---|---|---|---|---|---|---|---|
| | BMP-4 | VEGF | GM-CSF | BMP-4 | SCF | GM-CSF | BMP-4 | VEGF | SCF | VEGF | SCF | GM-CSF |
| d 0-5 | x | x | x | x | x | x | x | x | x | x | x | x |
| d 6-10 | | x | x | | x | x | | x | x | x | x | x |
| d 11-15 | | | x | | x | x | | x | | | x | x |
| d 16 on | | | x | | | x | | | | | | x |

TABLE VII

Reagents

| Growth Factors | Manufacture | Catalogue | Concentration Used |
|---|---|---|---|
| rhBMP-4 | R&D Systems | 314-BP | 50 ng/ml |
| rhSCF | R&D Systems | 255-SC-050 | 20 ng/ml |
| rhGM-CSF | R&D Systems | 215-GM-050 | 50 ng/ml |
| rhFLT3L | R&D Systems | 308-FKN-025 | 20 ng/ml |
| rhVEGF | R&D Systems | 293-VE-050 | 50 ng/ml |
| rhIL-4 | R&D Systems | 204-IL-010 | 50 ng/ml |
| rhTNF-alpha | R&D Systems | 210-TA-010 | 10 ng/ml |
| rhIFN-gamma | R&D Systems | 285-IF-100 | 20 ng/ml |
| rhIL-3 | R&D Systems | 203-IL-050 | 25 ng/ml |
| MIP-3B | Pepro Tech | 300-29B | 100 ng/ml |
| rhCD40L | R&D Systems | 617-CL-050/CF | 100 ng/ml |

TABLE VII-continued

Reagents

| Growth Factors | Manufacture | Catalogue | Concentration Used |
|---|---|---|---|
| rhIFN-alpha | R&D Systems | 11101-2 | 10 ng/ml |
| IL-1beta | R&D Systems | 201-LB-005 | 10 ng/ml |

Example 8

Comparison of Maturation Cocktail pPS cells differentiated to imDC according to various embodiments of the invention were matured to mDC using different combinations of cytokines/factors. A cell concentration of $0.05 \times 10^6$ cells/well were plated in 96 well plates and cultured for 24 hrs in X VIVO-15 media supplemented with various combinations of cytokines/factors as set forth in Table VIII. Concentrations of the factors used were as set forth above in Table VII. For Poly I:C 10 ug/ml was used; for PGE2 1 ug/ml was used; for iL-6 10 ng/ml was used. All tested maturation cocktails contained 50 ng/ml of GM-CSF. IL-12 and IL-10 levels from supernatants at 24 hours was measured using the BD™ Cytometric Bead Array (BD Biosciences, Franklin Lakes, N.J.) as indicative of maturation of imDC to mDC. The results suggested that as few as four exogenous cytokines could stimulate the maturation of imDC to mDC.

TABLE VIII

| | Maturation cocktail | | | | | | | pg/ml | |
|---|---|---|---|---|---|---|---|---|---|
| | TNFα | IL1β | IFNγ | PGE2 | POLY I:C | IFNα | CD40L | IL-12 | IL-10 |
| 1 | − | − | − | − | − | − | − | 0.0 | 35.8 |
| 2 | + | + | + | + | − | − | − | 1.9 | 118.4 |
| 3 | + | + | + | + | − | − | + | 2.6 | 104.8 |
| 4 | + | + | + | + | + | + | − | 1.4 | 219.8 |
| 5 | + | + | + | + | + | + | + | 1.9 | 206.3 |
| 6 | + | + | + | − | + | + | − | 0.0 | 155.6 |
| 7 | + | + | + | − | + | + | + | 1.9 | 202.8 |

The experiment was repeated using a cell concentration of $0.2 \times 10^6$ cells/well in 6 well plates, but this time a different panel of cytokines was tested. The cytokine concentrations were as follows: TNFα 10 ng/ml; IL-1β 10 ng/ml; IFN γ 20 ng/ml PGE2 1 ug/ml; IL-6 10 ng/ml. The supernatants were concentrated using Amicon Ultra-15 10,000 NMWL centrifuge tubes (Millipore Corp, Bedford, Mass.) and analyzed after 48 hour exposure to the various maturation cocktails for IL-12 and IL-6 production as indicative of DC maturation. As in the previous experiment all maturation cocktails also contained 50 ng/ml of GM-CSF. Also included as a positive control were monocyte-derived DC generated from human PBMCs. The results are presented in Table IX below.

TABLE IX

| Maturation Cocktail | | | | | Cytokine (pg/ml) | | |
|---|---|---|---|---|---|---|---|
| IFN-γ | TNF-α | IL-1β | PGE2 | IL-6 | IL-12 | IL-6 | Cell type |
| − | − | − | − | − | 2.0 | 96.3 | es-iDCs |
| + | + | + | + | − | 11.6 | 38,729.2 | es-mDCs |
| − | + | + | + | + | 2.2 | 53,438.0 | es-mDCs |
| + | − | + | + | − | 3.4 | 9,796.6 | es-mDCs |
| + | + | − | + | − | 1.7 | 195.3 | es-mDCs |
| − | + | + | + | + | 16.5 | 64,856.8 | Mo-mDCs |

Example 9

Generation of hTERT T Cell Lines

PBMCs were isolated from HLA-A2+ buffy coats of healthy human donors using Ficoll Plaque-Plus (GE Healthcare Bioscience AB, Piscataway, N.J.) separation methods. To generate imDC, monocytes from HLA-A2+ PBMCs were isolated using CD14+ microbeads (Miltenyi, Auburn, Calif.), and transferred into serum free AIM-V media (Invitrogen, Carlsbad, Calif.) containing rhGM-CSF (1000 U/ml) (Berlex, Richmond, Calif.) and rhIL-4 (1000 U/ml) (R&D systems, Minneapolis, Minn.), and incubated at 37° C. 5% $CO_2$ for 5 days. DC were matured for 24 hours by adding a cytokine cocktail comprising TNFα (10 ng/ml) (R&D systems), IL1β (10 ng/ml) (R&D systems), IL-6 (10 ng/ml) (R&D systems), and PGE2 (1 ug/ml) (R&D systems). mDC were harvested, washed 2× in AIM-V media, resuspended in 200 ul of AIM-V media, and pulsed with 540 hTERT peptide, a 9mer beginning with amino acid 540 of the hTERT protein (100 ug/ml) (AnaSpec Inc, San Jose, Calif.) for 2 hours at 37° C. 5% $CO_2$.

Autologous CD8+ T cells were isolated from PBMCs by depleting non-CD8+ cells using a CD8+ T cell magnetic separation kit (Miltenyi, Auburn, Calif.). CD8+ cells were resuspended in AIM-V media containing 10% human AB serum (Valley Biomedical, Winchester, Va.) and transferred to 24 wells plates at a concentration of 1.0-2.0×10⁶ cells/ml. 540 hTERT pulsed DC were added to the wells at a stimulator to responder ratio of 1:10 and incubated at 37° C. 5% $CO_2$. The following day, recombinant human IL-7 (10 ng/ml) (R&D systems) and IL-2 (10 U/ml) (R&D systems) were added to the culture.

Peptide hTERT 540 restimulations were performed every 7-10 days. For restimulation autologous PBMC were used to present the antigen. Autologous PBMCs were transferred to 24 well plates at a concentration of 2.0-3.0×10⁶ cells/well containing serum free AIM-V media and hTERT 540 peptide (10 ug/ml). PBMCs were kept at 37° C. 5% $CO_2$ for 2 hours to promote attachment of cells to the plate. Non-adherent cells were removed with 2× washes with AIM-V media. Adherent PBMCs were pulsed for an additional 2 hours with 540 hTERT peptide (10 ug/ml) and then irradiated at 2000 rads.

CD8+ T cells from the initial priming with 540 hTERT pulsed DC were harvested, washed 1×, and transferred into wells containing 540 hTERT pulsed irradiated adherent PBMCs. IL-12 (10 ng/ml) (R&D systems) was added to the culture. The following day, recombinant human IL-7 (10 ng/ml) and/or IL-2 (10 U/ml) were added to the culture. Every 3-4 days, half the medium was removed and fresh medium was added containing IL-7 and/or IL-2 when appropriate. At least 3 restimulations using 540 hTERT pulsed irradiated autologous adherent PBMCs were performed.

The percent positive 540 hTERT specific CD8+ T cells were determined by staining cells with 540 pentamer labeled with APC (ProImmune, Bradenton, Fla.) and anti-human CD8 FITC conjugated Ab (Proimmune, Bradenton, Fla.) using FlowJo software (Tree Star, Ashland, Oreg.). The TERT specific CD8+ cells were collected by flow cytometry using a FACSCaliber™ (Becton Dickinson, San Jose, Calif.) and used in subsequent experiments.

Example 10

ELISpot IFNγ Assay of 540 hTERT T Cell Lines hES derived mDC (Example 1) were resuspended in 200 ul of serum free AIM-V media (Invitrogen, Carlsbad, Calif.) and pulsed with 540 hTERT peptide (100 ug/ml) for 2 hours at 37° C. 5% $CO_2$. Non-pulsed mDC served as a control. Non-pulsed hES derived mDC served as a control. The mDC were washed 2× in AIM-V media, resuspended in AIM-V media, and plated with 540 hTERT T cell lines at a stimulator to responder ratio of 1:10 in ELISpot plates coated with anti-IFN-γ Ab (10 ug/ml) (Mabtech, Mariemont, Ohio). The assay plate was placed at 37° C. 5% $CO_2$ for 16-24 hours, and developed following the instructions provided by the manufacturer. Spots were counted using a CTL Analyzer (Cellular Technology Limited, Decatur, Ill.). The results are shown in FIG. 8 and demonstrate that mDC differentiated from hES stimulate a specific T cell response to a hTERT antigen.

Example 11

Proliferation of 540 hTERT T Cell Lines

The 540 hTERT T cell lines were resuspended in prewarmed PBS/0.1% BSA at 1.0×10⁶/ml. CFSE (Invitrogen, Carlsbad, Calif.) was added to the cells at a final concentration of 2 uM and incubated at 37° C. for 10 minutes. The stain was quenched by the addition of prechilled AIM-V media containing 10% PBS (Clonetech, Mountain View, Calif.). The cells were washed 2× before setting up the assay. Mature hES derived DC (Example 1) were pulsed with 10 μg/ml of 540 hTERT peptide (Anaspec, San Jose, Calif.) for 2 hours at 37° C. 5% $CO_2$ and washed 2× in AIM-V media before plating at 2×10⁴/well in 96 well U bottom Falcon™ plate (BD, San Jose, Calif.). CFSE labeled 540 hTERT T cell lines were plated at 2×10⁵ cells/well. Non-pulsed hES derived mDC served as a control. On day 4, cells were harvested and stained with 540 pentamer reagent conjugated to APC (ProImmune, Bradenton, Fla.). The cells were washed 2× with FACS buffer, and stained with 7AAD prior to collection using a FACSCaliber™ (Becton Dickinson, San Jose, Calif.). The analysis was performed using FlowJo software (Tree Star, Ashland, Oreg.). The results are presented in FIG. 9 and demonstrate that mDC differentiated from hES cells can present hTERT antigen in the context of HLA-A2 and stimulate antigen specific T cell proliferation.

Example 12

Immunostimulatory Capacity of Irradiated mDC

Mature dendritic cells were differentiated in vitro from pPS cells according to the method described in Example 1.

Figure 10:
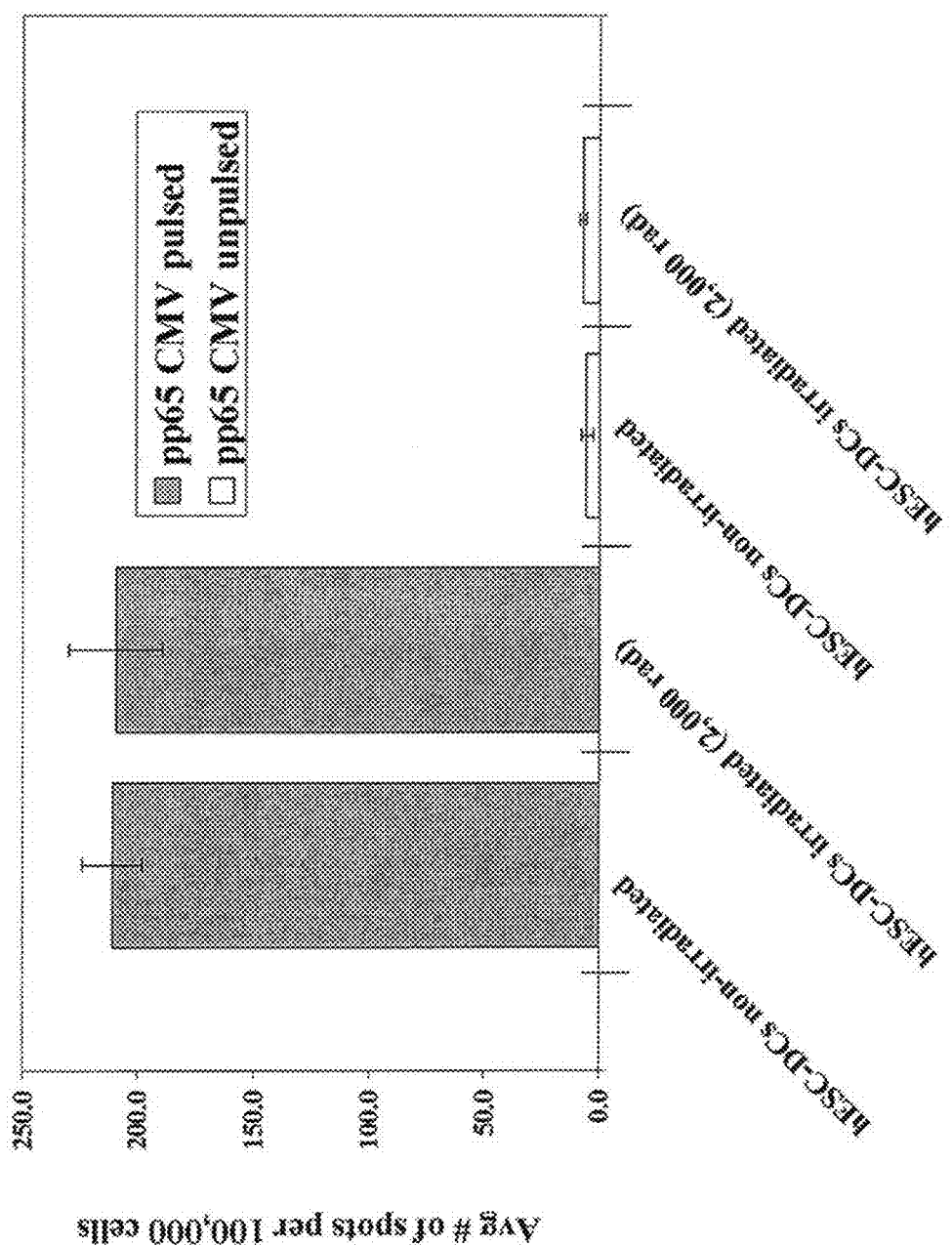
FIG. 10 is a graph comparing the stimulation of an antigen specific T cell response by irradiated mDC (hES-DC) versus non-irradiated mDC (hES-DC) either pulsed or unpulsed with peptide antigen.

To address the effects of irradiation on dendritic cells differentiated in vitro from hES cells (hESC-DCs), the ability of irradiated and non-irradiated hESC-DCs to stimulate antigen specific effector responses of T cells was compared. CMV peptide pp65 (amino acid sequence 495-503) was used to demonstrate hESC-DC antigen presentation to CD8+ lymphocytes. Characterized PBMC responders (Cellular Technology Limited, Decatur, Ill.), which contain CD8+ T cells that recognize pp65 complexed to HLA-A2 were used as the responder cells. For the pp65 specific antigen presentation, matured hESC-DC were resuspended in 150 ul of serum free AIM-V medium (Invitrogen, Carlsbad, Calif.) either supplemented with 10 µg/ml pp65 peptide or unsupplemented. The cells were incubated at 37° C. in 5% $CO_2$ for 2 hours, and then washed 2 times with AIM-V media (Invitrogen, Carlsbad, Calif.). A portion of the pp65 pulsed and unpulsed hESC-DCs were X-ray irradiated at 2,000 rad for 4 minutes and 14 seconds using the Torrex 150D X-ray inspection system (EG&G Astrophysics Research Corporation, Long Beach, Calif.). The irradiated and non-irradiated hESC-DCs were plated onto an ELISPOT plate at $1 \times 10^4$ cells/100 ul/well at a 10:1 responder to stimulator ratio. The characterized PBMC responders were thawed in 37° C. water bath, washed two times, resuspended in AIM-V media (Invitrogen, Carlsbad, Calif.), and plated at $1 \times 10^5$ cells/100 ul/well on ELISPOT plates (Millipore, Bedford Mass.). ELISPOT plates were coated with anti-IFNγ Ab (Mabtech, Mariemont, Ohio) at 10 ug/ml overnight (16-24 hours). The assay plates were placed at 37° C. and 5% $CO_2$ for 16-24 hours, and developed following the instructions provided by Mabtech. Spots were counted using a CTL Analyzer (Cellular Technology Limited, Decatur, Ill.). The results, shown in FIG. 10, demonstrate irradiated hESC-DCs maintained the capacity to stimulate IFNγ production in an antigen specific manner.

Example 13

Chemotactic Migration of Irradiated mDC

Figure 11:
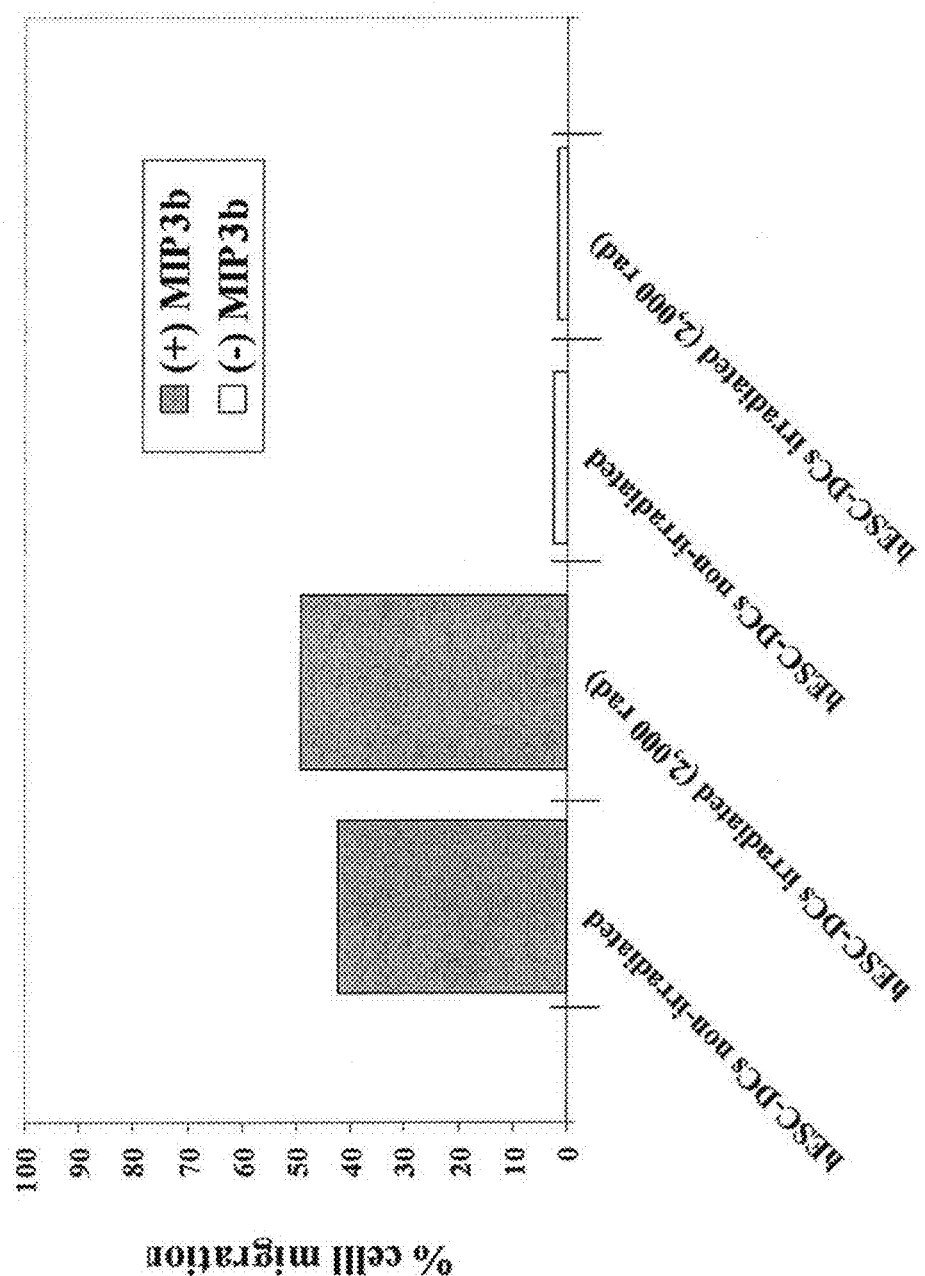
FIG. 11 is a graph comparing DC migration in response to chemotactic ligand MIP3 of irradiated mDC (hES-DC) versus non-irradiated mDC (hES-DC).

Mature dendritic cells were differentiated according to the same protocol used in Example 12. The capacity of irradiated and non-irradiated mDC (hESC-DCs) to migrate in the presence of the chemotactic ligand MIP3β (MIP3b in FIG. 11) using an in vitro transwell assay was investigated. AIM-V media (Invitrogen, Carlsbad, Calif.) was added to the upper and lower chambers of Transwell 24 well plates containing 8.0 uM pore size inserts (Corning, Corning, N.Y.), and incubated overnight at 37° C., 5% $CO_2$ to equilibrate the membrane. mDCs were harvested and washed 2 times in AIM-V media. The cells were resuspended in AIM-V media at $1.5 \times 10^6$ cells/ml, and a portion of these cells were X-ray irradiated at 2,000 rad using the Torrex 150D X-ray inspection system (EG&G Astrophysics Research Corporation, Long Beach, Calif.). After removal of the media from the transwell, 0.6 ml of AIM-V with or without the chemokine MIP3β (100 ng/ml) was added to the lower chamber. A volume of 0.1 ml of irradiated or non-irradiated mDCs ($0.15 \times 10^6$ cells) was added to the top chamber. The transwell plate was incubated for 2 hours at 37° C., 5% $CO_2$. The number of cells that migrated to the bottom chamber was determined using a hemacytometer. The results presented in FIG. 11 demonstrated irradiation did not affect the ability of mDCs to migrate in response to MIP3β.

Example 14

Comparison of Cell Yield from Commercially Available Media

Figure 12:
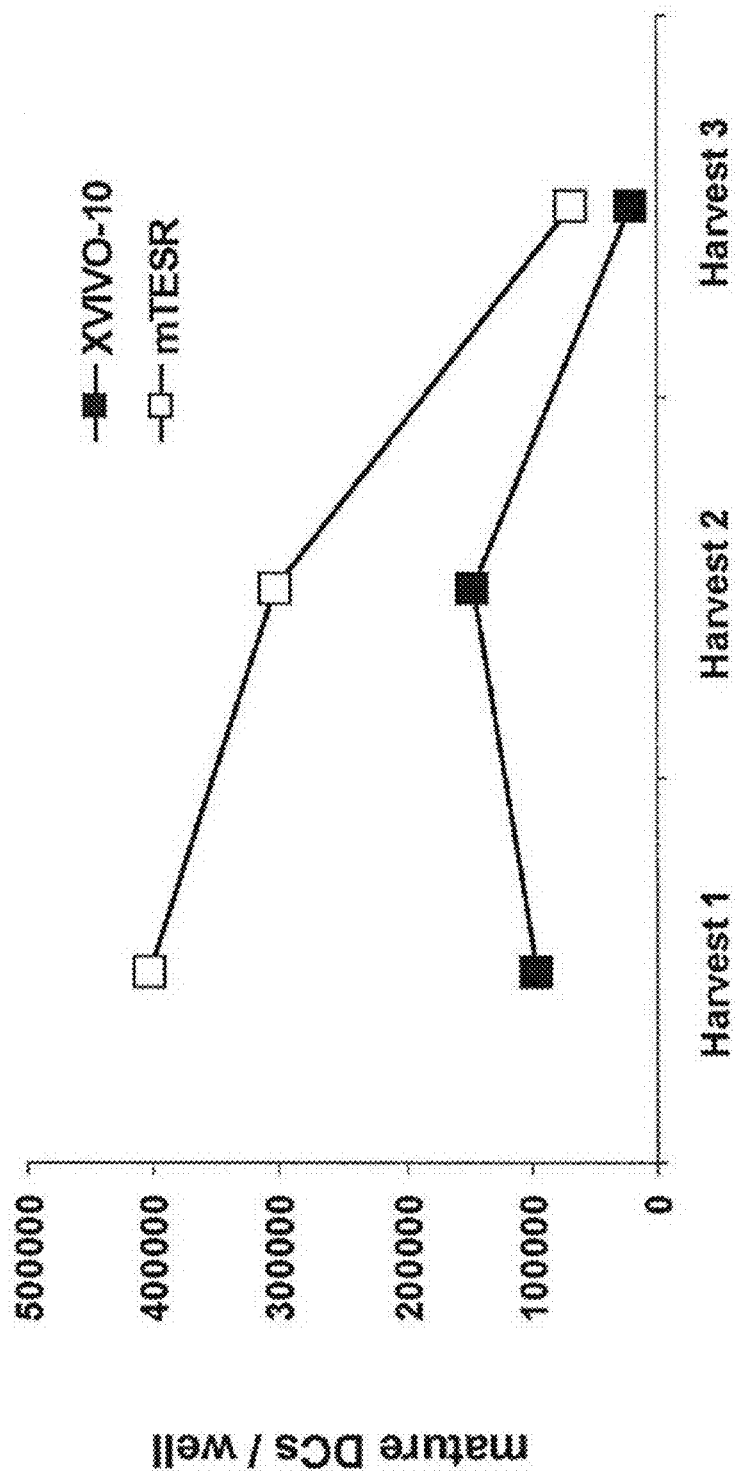
FIG. 12 is graph comparing mDC yields in hES cells grown in either XVivo10™ or mTeSR™ media.
Figure 13A:
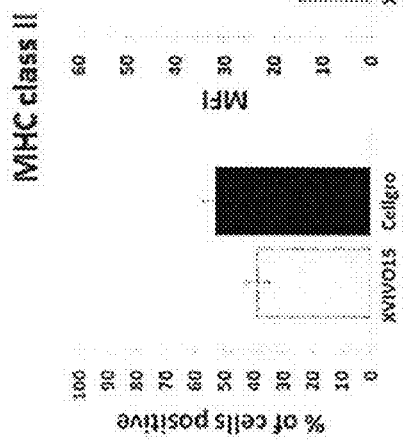
FIG. 13A, FIG. 13B, FIG. 13C and FIG. 13D are graphs comparing surface marker expression of DC differentiated in vitro from hES cells and matured in either Cellgro™ or X Vivo-15™ media.
Figure 13B:
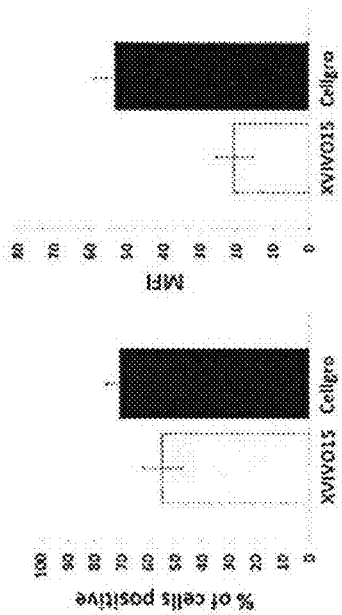
Figure 13C:
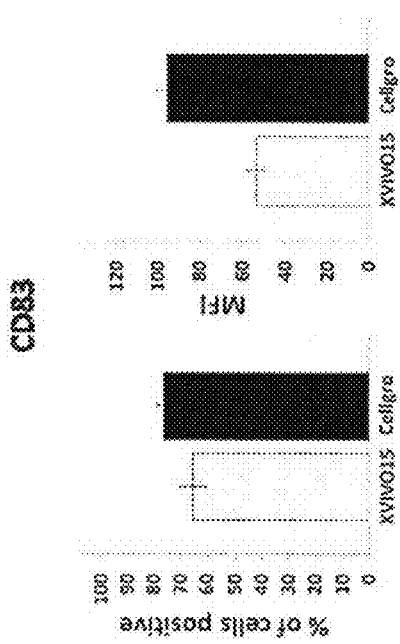
Figure 13D:
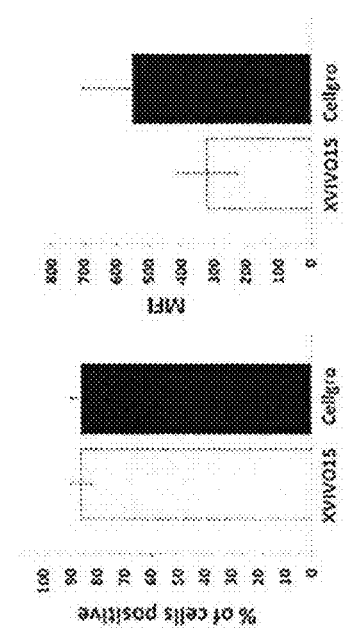

The effect on mDC cell yield of two commercially available media, mTeSR™ serum free media (Stem Cell Technologies, Vancouver, BC, Canada) and XVIVO-10™ (Lonza, Walkersville, Md.) was investigated. H1 hESCs culture and differentiation methods were performed as described in Example 1. The number of mature DCs at each harvest was compared between hESCs that originated from XVIVO-10 or mTeSR cultures, FIG. 12. A total of 3 harvests were performed from the initial differentiation. While both media successfully produced mDC differentiated in vitro from hES, the results suggest hESCs cultured in mTeSR provide better cell yields than XVIVO-10.

Example 15

Maturation of hESC-Derived DCs Cultured in Commercially Available Media

Mature DCs possess the capacity to stimulate T cell responses; therefore it is desirable to optimize the maturation process for hESC-derived DCs. (See, e.g. Chiara et al, 2007 We differentiated H1 hESCs as described in Example 1 but used Cellgro DC media during the steps to generate immature and mature hESC-derived DC. After 24 hrs of maturation, cells were harvested and evaluated for the presence of a mature DC phenotype based on: 1) cell surface marker expression, 2) migration, and 3) IL-12 expression.

Flow cytometry as described in Example 2 was used to analyze the cell surface expression of DC associated markers: MHC class II, CD83, CD86, and CCR7. Mature hESC-derived DCs cultured in Cellgro™ DC media had both elevated cell percent positive (%) and expression levels (MFI) of MHC class II, CD83, and CCR7 compared to XVIVO-15™ cultured DCs, FIG. 13. The % of cells expressing CD86 levels remained unchanged, but the mean fluorescent intensity (MFI) was higher using Cellgro™ DC medium. This data suggests Cellgro™ DC media promotes the generation of a more robust mature DC surface phenotype.

Figure 14:
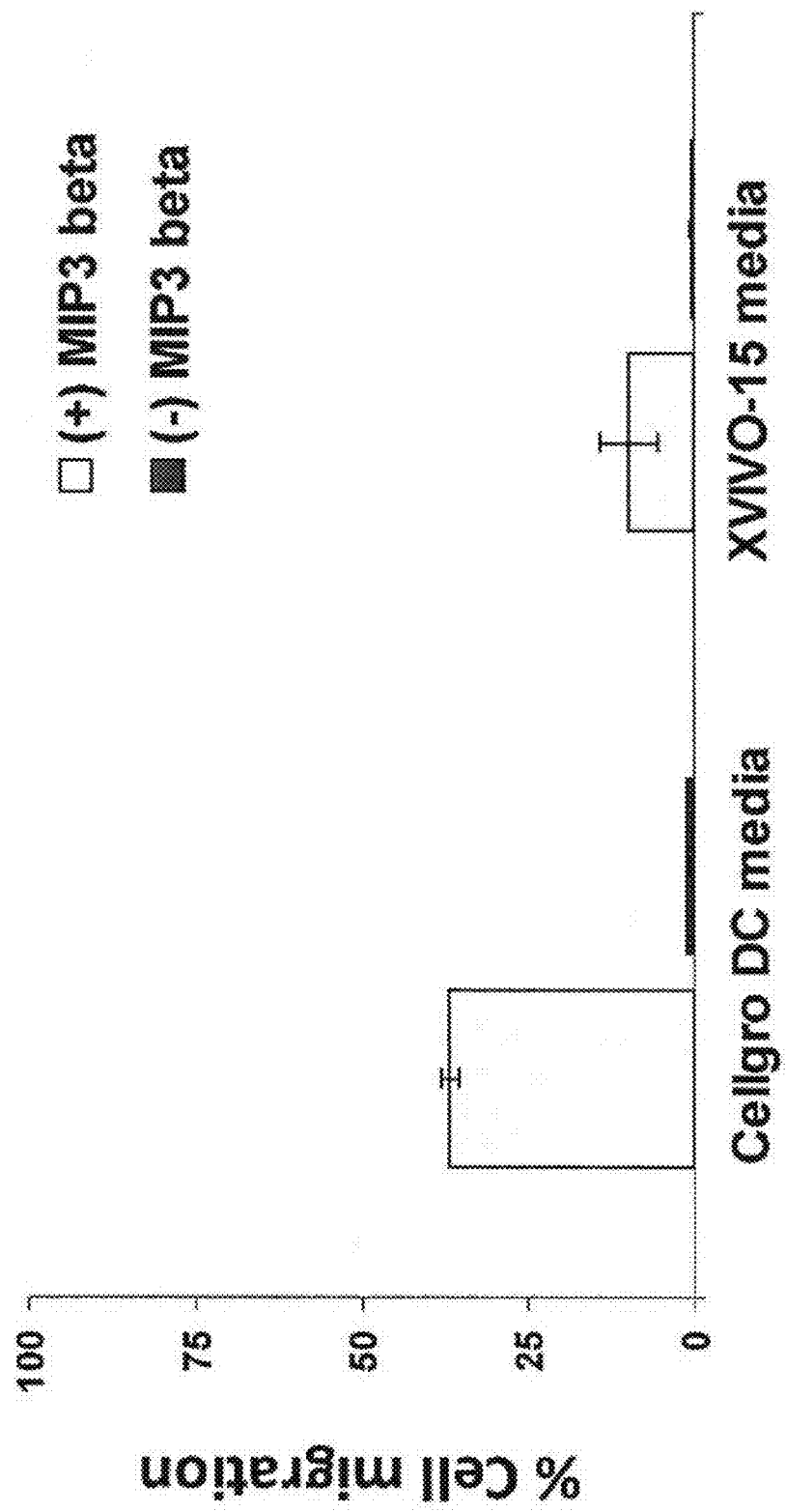
FIG. 14 is a graph comparing cell migration of hES derived mDC cultured in Cellgro™ or X-Vivo-15™.

Next the migration efficiency of hESC-derived mature DCs cultured in Cellgro™ DC and XVIVO-15™ media was studied using a Transwell assay as described in Example 5. hESC-derived DCs cultured in XVIVO-15™ required to be matured for at least 48 hrs of maturation for effective migration. In contrast hESC-derived mature DCs cultured and matured in Cellgro™ DC media have an increased capacity to migrate in response to MIP3 beta compared to XVIVO-15™ at 24 hrs (FIG. 14). These data suggest that hESC-derived DCS cultured in Cellgro™ DC media have improved migration at 24 hrs post maturation.

Figure 15:
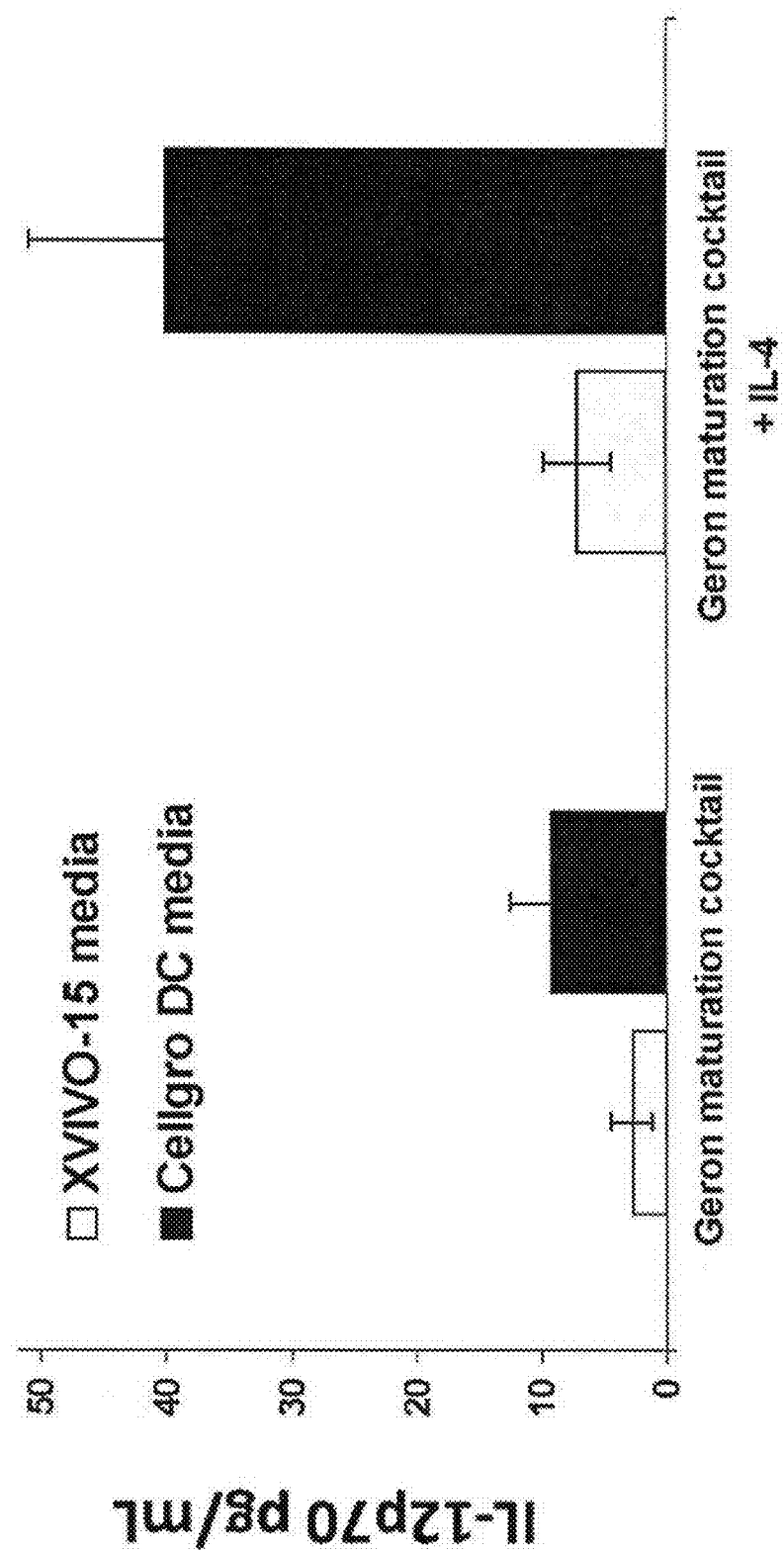
FIG. 15 is a graph comparing IL-12 production from hESC derived DC cultured in either Cellgro™ or X-Vivo-15™ media either with or without the addition of exogenous IL-4 to the maturation cocktail.

IL-12 helps promote a Th1 type immune response; therefore it would be useful to optimize the expression of IL-12 from mature hESC-derived DCs. IL-12 expression levels were detected as described in Example 4. hESC-derived mature DCs cultured in Cellgro™ DC had higher IL-12 expression levels (3.4 fold) compared to XVIVO-15™ cultured DCs, (FIG. 15). The addition of IL-4 to the maturation cocktail can enhance IL-12 expression from DCs (see, e.g. Ebner et al, (2001) *J. Immunology* 166:633). IL-4 increased the expression of IL-12 from both medium conditions, but hESC-derived mature DCs cultured in Cellgro™ DC media had markedly higher levels of IL-12 production (5.6 fold), (FIG. 15). Taken together, these data suggest hESC-derived mature DCs cultured in Cellgro™ DC media have the capacity to express IL-12 at higher levels than DCs cultured in XVIVO-15™.

Example 16

Figure 16:
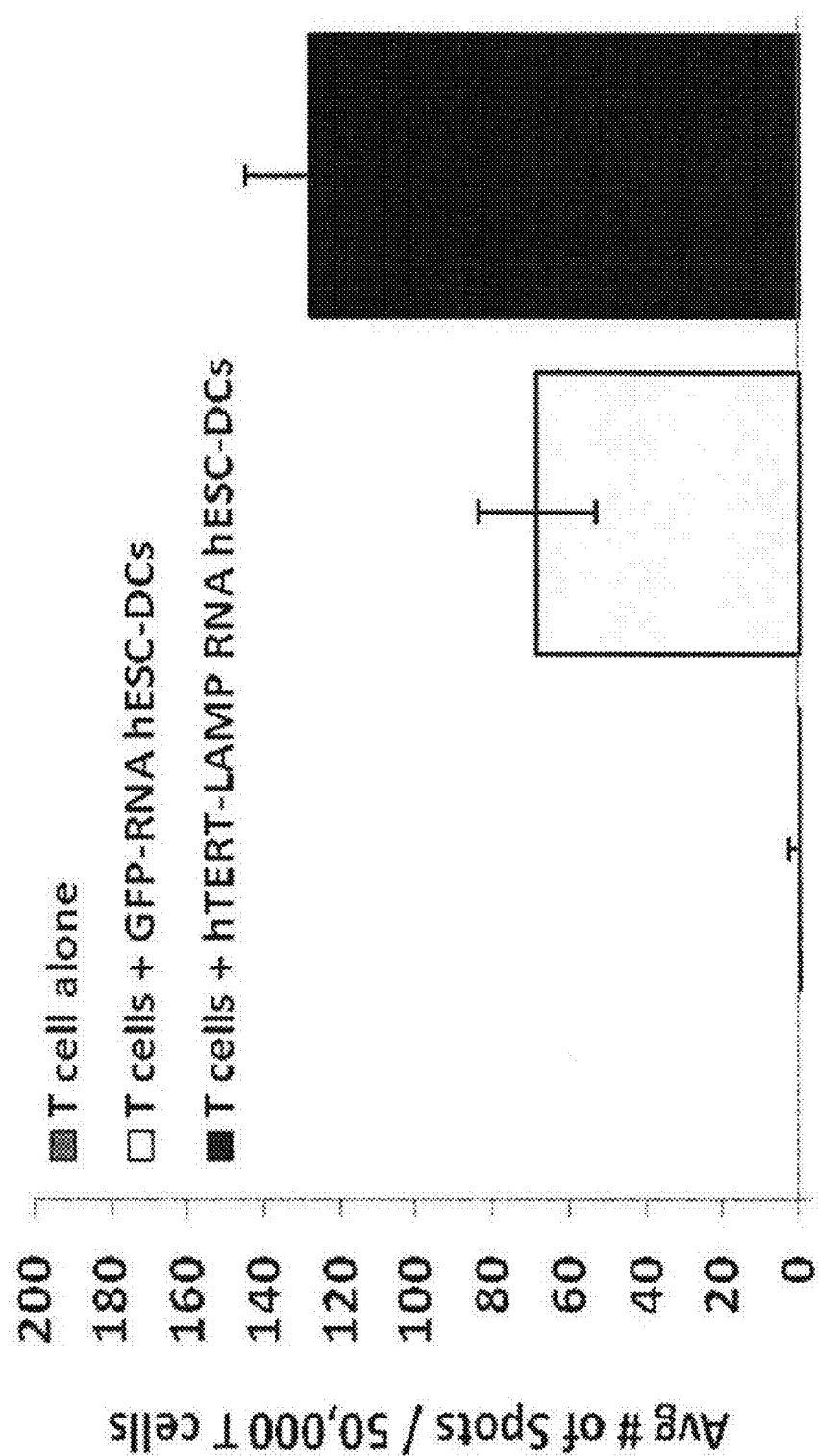
FIG. 16 is graph comparing IFNγ production from TERT specific T cells co-incubated with mDCs transfected with GFP; mDCs transfected with hTERT-LAMP and T cells alone (without co-incubation with mDC cells).

Stimulation of 540 hTERT T Cell Lines by hESC-Derived DCs Transfected with RNA Encoding hTERT-LAMP H1 hESCs were differentiated according to methods described in Example 1 except mTeSR™ was used to culture hESCs and Cellgro™ DCs to generate hESC-derived immature and mature DCs. Between 2.0-4.0e6 hESC-derived mature DCs were electroporated with RNA encoding hTERT-LAMP or GFP in 0.4 cm cuvettes (Biorad, Hercules, Calif.) using a Biorad Gene Pulser Xcell (Biorad, Hercules, Calif.) using the following parameters: 300V, 150 uF, and 100Ω. Electroporated cells were washed 1× in Cellgro™ DC media, and cells were transferred into maturation medium for an additional 6 hrs. GFP- and hTERT-LAMP RNA electroporated hESC-derived mature DCs were harvested and co-incubated with 540 hTERT T cell lines to detect the expression IFNγ as described in Examples 9 and 10. Results demonstrated that hESC-derived mature DCs electroporated with hTERT-LAMP RNA stimulated increased levels of IFNγ from 540 hTERT specific T cell lines compared to GFP-RNA transfected hESC-derived DCs, (FIG. 16). This data suggests hESC-derived DCs have the capacity to process and present hTERT antigen.

Many modifications and variations of this invention can be made without departing from its scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

The invention claimed is:

1. A system for the production of antigen presenting cells comprising: a) a first isolated cell population comprising human pluripotent stem cells in a cell culture medium comprising granulocyte-macrophage colony stimulating factor (GM-CSF) and bone morphogenic protein 4 (BMP-4); and b) a second isolated cell population comprising mature dendritic cells which are the in vitro progeny of a portion of the first isolated cell population, wherein the system is stromal cell and interleukin 3 (IL-3) free.

2. The system of claim 1, wherein at least 5% of the mature dendritic cells express one or more markers chosen from CD86 and CD83.

3. The system of claim 2, wherein the mature dendritic cells expressing one or more markers chosen from CD86 and CD83 further express one or more of the following MHCII and CCR7.

4. The system of claim 1, wherein the human pluripotent stem cells are human embryonic stem cells.

5. The system of claim 1, wherein the system is serum free.

6. The system of claim 1, wherein the cell culture medium comprising GM-CSF and BMP-4 further comprises one or more factors selected from vascular endothelial growth factor (VEGF), stem cell factor (SCF), and interleukin 4 (IL-4).

7. A cell culture, comprising: a) a first isolated cell population comprising human pluripotent stem cells in a cell culture medium comprising granulocyte-macrophage colony stimulating factor (GM-CSF) and bone morphogenic protein 4 (BMP-4) and b) a second isolated cell population comprising dendritic cells which are the in vitro differentiated progeny of a portion of the first isolated cell population, wherein the cell culture is stromal cell and interleukin 3 (IL-3) free.

8. The cell culture of claim 7, wherein the human pluripotent stem cells are human embryonic stem cells.

9. The cell culture of claim 7, wherein the cell culture is serum free.

10. The cell culture of claim 7, wherein the cell culture medium comprising GM-CSF and BMP-4 further comprises one or more factors selected from vascular endothelial growth factor (VEGF), stem cell factor (SCF), and interleukin 4 (IL-4).

11. A first and a second population of cells, comprising: a) a first isolated cell population comprising human pluripotent stem cells in a cell culture medium comprising granulocyte-macrophage colony stimulating factor (GM-CSF) and bone morphogenic protein 4 (BMP-4) and b) a second isolated cell population comprising dendritic cells which are the in vitro progeny of a portion of the first isolated cell population, wherein the first and the second population of cells are stromal cell and interleukin 3 (IL-3) free.

12. The first and the second population of cells of claim 11, wherein the human pluripotent stem cells in the first isolated cell population are human embryonic stem cells.

13. The first and the second population of cells of claim 11, wherein the first and the second populations are cultured in a serum free medium.

14. The first and the second population of cells of claim 11, wherein the cell culture medium comprising GM-CSF and BMP-4 further comprises one or more factors selected from vascular endothelial growth factor (VEGF), stem cell factor (SCF), and interleukin 4 (IL-4).

* * * * *